(12) United States Patent
Khosravi et al.

(10) Patent No.: US 11,808,722 B2
(45) Date of Patent: *Nov. 7, 2023

(54) SENSOR SYSTEM AND ELECTRODES

(71) Applicant: NanoDX, Inc., Southborough, MA (US)

(72) Inventors: Farhad Khosravi, Santa Fe, NM (US); David Bastable, Santa Fe, NM (US); Sergey A. Dryga, Rio Rancho, NM (US)

(73) Assignee: NanoDX, Inc., Southborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/897,408

(22) Filed: Aug. 29, 2022

(65) Prior Publication Data

US 2022/0412907 A1  Dec. 29, 2022

Related U.S. Application Data

(60) Continuation of application No. 17/330,206, filed on May 25, 2021, now Pat. No. 11,493,466, which is a
(Continued)

(51) Int. Cl.
*G01N 27/04* (2006.01)
*G01N 33/487* (2006.01)
(Continued)

(52) U.S. Cl.
CPC .......... *G01N 27/04* (2013.01); *A61B 5/1477* (2013.01); *G01N 27/327* (2013.01);
(Continued)

(58) Field of Classification Search
CPC ........ G01N 27/00; G01N 27/02; G01N 27/04; G01N 27/26; G01N 27/28; G01N 27/30; G01N 27/327; G01N 27/3275; G01N 27/3278; G01N 27/403; G01N 27/41; G01N 33/00; G01N 33/48; G01N 33/483;
(Continued)

(56) References Cited

U.S. PATENT DOCUMENTS 5,407,554 A  4/1995  Saurer
7,875,194 B2  1/2011  Lee et al.
(Continued)

FOREIGN PATENT DOCUMENTS

JP    2016159776 A  *  9/2016  ............. H01H 13/70
WO   WO-2015068974 A1  *  5/2015  ............. H01L 43/06

OTHER PUBLICATIONS

U.S. Appl. No. 17/556,930, filed Dec. 20, 2021, Khosravi et al.
(Continued)

*Primary Examiner* — Hoai-An D. Nguyen
(74) *Attorney, Agent, or Firm* — Wolf, Greenfield & Sacks, P.C.

(57) ABSTRACT

Sensors having an advantageous design and methods for fabricating such sensors are generally provided. Some sensors described herein comprise pairs of electrodes having radial symmetry, pairs of nested electrodes, and/or nanowires. Some embodiments relate to fabricating electrodes by methods in which nanowires are deposited from a fluid contacted with a substrate in a manner such that it evaporates and is replenished.

26 Claims, 28 Drawing Sheets

Related U.S. Application Data division of application No. 17/131,657, filed on Dec. 22, 2020, now Pat. No. 11,486,842.

(60) Provisional application No. 62/953,143, filed on Dec. 23, 2019, provisional application No. 62/953,140, filed on Dec. 23, 2019, provisional application No. 62/953,148, filed on Dec. 23, 2019.

(51) Int. Cl.
*G01N 27/403* (2006.01)
*G01N 27/414* (2006.01)
*H01L 29/06* (2006.01)
*G01N 27/327* (2006.01)
*A61B 5/1477* (2006.01)

(52) U.S. Cl.
CPC ....... *G01N 27/3278* (2013.01); *G01N 27/403* (2013.01); *G01N 27/414* (2013.01); *G01N 33/48707* (2013.01); *H01L 29/0676* (2013.01)

(58) Field of Classification Search
CPC .. G01N 33/487; G01N 33/48707; A61B 5/00; A61B 5/145; A61B 5/1468; A61B 5/1477; H01L 29/00; H01L 29/02; H01L 29/06; H01L 29/0657; H01L 29/0665; H01L 29/0676
USPC .......... 324/600, 649, 691, 500, 537, 750.01, 324/750.03, 750.08, 754.12, 754.15, 324/76.11, 92
See application file for complete search history.

(56) References Cited

U.S. PATENT DOCUMENTS

| | | | |
|---|---|---|---|
| 9,366,643 B2* | 6/2016 | Albuschies | B82Y 40/00 |
| 9,972,649 B2 | 5/2018 | Spanoudaki et al. | |
| 11,054,384 B1 | 7/2021 | Khosravi et al. | |
| 11,255,805 B2 | 2/2022 | Khosravi et al. | |
| 11,486,842 B2 | 11/2022 | Khosravi et al. | |
| 11,493,466 B2 | 11/2022 | Khosravi et al. | |
| 2004/0023253 A1 | 2/2004 | Kunwar et al. | |
| 2009/0084686 A1 | 4/2009 | Yun et al. | |
| 2010/0112546 A1* | 5/2010 | Lieber | G01N 33/6854 |
| | | | 530/391.1 |
| 2010/0253184 A1 | 10/2010 | Choi et al. | |
| 2011/0148286 A1* | 6/2011 | Ju | H05B 33/145 |
| | | | 313/503 |
| 2012/0036919 A1* | 2/2012 | Kamins | G01N 27/127 |
| | | | 438/49 |
| 2014/0057283 A1 | 2/2014 | Wang et al. | |
| 2014/0216506 A1 | 8/2014 | Inatomi | |
| 2015/0323490 A1 | 11/2015 | Luan et al. | |
| 2017/0160227 A1 | 6/2017 | Savoy et al. | |
| 2018/0363043 A1 | 12/2018 | Hashimoto et al. | |
| 2019/0017981 A1 | 1/2019 | Dutta et al. | |
| 2020/0118623 A1* | 4/2020 | Meredith | G11C 11/5664 |
| 2021/0190711 A1 | 6/2021 | Khosravi et al. | |
| 2021/0190723 A1 | 6/2021 | Khosravi et al. | |
| 2021/0262968 A1 | 8/2021 | Khosravi et al. | |
| 2021/0278364 A1 | 9/2021 | Khosravi et al. | |
| 2021/0285906 A1 | 9/2021 | Khosravi et al. | |
| 2022/0113269 A1 | 4/2022 | Khosravi et al. | |
| 2022/0390402 A1 | 12/2022 | Khosravi et al. | |

OTHER PUBLICATIONS

U.S. Appl. No. 17/330,216, filed May 25, 2021, Khosravi et al.
U.S. Appl. No. 17/856,438, filed Jul. 1, 2022, Khosravi et al.
International Search Report and Written Opinion for International Application No. PCT/US2020/066765 dated Apr. 6, 2021.
[No Author Listed], Circle formula. MATH net. 2022. https://www.math.net/circle-formula [last accessed Nov. 15, 2022].
Alali et al., Economic Evaluations in the Diagnosis and Management of Traumatic Brain Injury: A Systematic Review and Analysis of Quality. Value Health. Jul. 2015; 18(5):721-34. doi: 10.1016/j.jval.2015.04.012. Epub Jul. 26, 2015.
Ambhorkar et al., Nanowire-Based Biosensors: From Growth to Applications. Micromachines (Basel). Dec. 19, 2018;9(12):679. doi: 10.3390/mi9120679.
Bazarian et al., Classification accuracy of serum Apo A-I and S100B for the diagnosis of mild traumatic brain injury and prediction of abnormal initial head computed tomography scan. J Neurotrauma. Oct. 15, 2013;30(20):1747-54. doi: 10.1089/neu.2013.2853. Epub Aug. 24, 2013.
Bazarian et al., Serum GFAP and UCH-L1 for prediction of absence of intracranial injuries on head CT (ALERT-TBI): a multicentre observational study. Lancet Neurol. Sep. 2018;17(9):782-789. doi: 10.1016/S1474-4422(18)30231-X. Epub Jul. 24, 2018.
Calcagnile et al., Clinical validation of S100B use in management of mild head injury. BMC Emerg Med. Oct. 27, 2012;12:13. doi: 10.1186/1471-227X-12-13.
Ercole et al., Kinetic modelling of serum S100b after traumatic brain injury. BMC Neurol. Jun. 17, 2016;16:93. doi: 10.1186/s12883-016-0614-3.
Gao et al., Silicon nanowire arrays for label-free detection of DNA. Anal Chem. May 1, 2007;79(9):3291-7. doi: 10.1021/ac061808q. Epub Apr. 4, 2007.
Gardner et al., Age-Related Differences in Diagnostic Accuracy of Plasma Glial Fibrillary Acidic Protein and Tau for Identifying Acute Intracranial Trauma on Computed Tomography: A TRACK-TBI Study. J Neurotrauma. Oct. 15, 2018;35(20):2341-2350. doi: 10.1089/neu.2018.5694. Epub Jun. 29, 2018.
Gill et al., Glial fibrillary acidic protein elevations relate to neuroimaging abnormalities after mild TBI. Neurology. Oct. 9, 2018;91(15):e1385-e1389. doi: 10.1212/WNL.0000000000006321. Epub Sep. 12, 2018.
Giza et al., Summary of evidence-based guideline update: evaluation and management of concussion in sports: report of the Guideline Development Subcommittee of the American Academy of Neurology. Neurology. Jun. 11, 2013;80(24):2250-7. doi: 10.1212/WNL.0b013e31828d57dd. Epub Mar. 18, 2013.
Goyal et al., S100b as a prognostic biomarker in outcome prediction for patients with severe traumatic brain injury. J Neurotrauma. Jun. 1, 2013;30(11):946-57. doi: 10.1089/neu.2012.2579.
Haydel, Management of mild traumatic brain injury in the emergency department. Emerg Med Pract. Sep. 2012; 14(9):1-24. Epub Jul. 20, 2012.
Jagoda et al., Clinical policy: neuroimaging and decisionmaking in adult mild traumatic brain injury in the acute setting. Ann Emerg Med. Dec. 2008;52(6):714-48. doi: 10.1016/j.annemergmed.2008.08.021.
Kilbaugh et al., Peripheral Blood Mitochondrial DNA as a Biomarker of Cerebral Mitochondrial Dysfunction following Traumatic Brain Injury in a Porcine Model. PLOS One. Jun. 22, 2015;10(6):e0130927. doi: 10.1371/journal.pone.0130927.
Lange et al., Clinical utility of the protein S100B to evaluate traumatic brain injury in the presence of acute alcohol intoxication. J Head Trauma Rehabil. Mar.-Apr. 2012;27(2):123-34. doi: 10.1097/HTR.0b013e31820e6840.
Lee et al., Flash-induced nanowelding of silver nanowire networks for transparent stretchable electrochromic devices. Sci Rep. Feb. 9, 2018;8(1):2763. doi: 10.1038/s41598-018-20368-3.
Luoto et al., A Systematic Review of the Usefulness of Glial Fibrillary Acidic Protein for Predicting Acute Intracranial Lesions following Head Trauma. Front Neurol. Dec. 4, 2017;8:652. doi: 10.3389/fneur.2017.00652.
Mathews et al., Cancer risk in 680,000 people exposed to computed tomography scans in childhood or adolescence: data linkage study of 11 million Australians. BMJ. May 21, 2013;346:f2360. doi: 10.1136/bmj.f2360.
Mayeux, Biomarkers: potential uses and limitations. NeuroRx. Apr. 2004;1(2):182-8. doi: 10.1602/neurorx.1.2.182.
Minkkinen et al., Prospective Validation of the Scandinavian Guidelines for Initial Management of Minimal, Mild, and Moderate Head

(56) References Cited

OTHER PUBLICATIONS

Injuries in Adults. J Neurotrauma. Oct. 15, 2019;36(20):2904-2912. doi: 10.1089/neu.2018.6351. Epub Jul. 10, 2019.

Mu et al., Silicon Nanowire Field-Effect Transistors—A Versatile Class of Potentiometric Nanobiosensors. IEEE Access. Apr. 2015;3:287-302.

Mukhtar et al., Emerging mutations in spike and other structural proteins of SARS-COV-2. Authorea. Mar. 13, 2021:23 pages.

Nagy et al., The utility of head computed tomography after minimal head injury. J Trauma. Feb. 1999;46(2):268-70. doi: 10.1097/00005373-199902000-00012.

Nishijima et al., Immediate and delayed traumatic intracranial hemorrhage in patients with head trauma and preinjury warfarin or clopidogrel use. Ann Emerg Med. Jun. 2012;59(6):460-8.e1-7. doi: 10.1016/j.annemergmed.2012.04.007.

Oris et al., The Biomarker S100B and Mild Traumatic Brain Injury: A Meta-analysis. Pediatrics. Jun. 2018;141(6):e20180037. doi: 10.1542/peds.2018-0037. Epub May 1, 2018.

Patolsky et al., Detection, Stimulation, and Inhibition of Neuronal Signals with High-Density Nanowire Transistor Arrays. Science. Aug. 2006;313(5790):1100-4. Erratum in: Science. Jul. 20, 2007;317(5836):320.

Pitera et al., Dielectric Properties of Proteins from Simulation: The Effects of Solvent, Ligands, pH, and Temperature. Biophysical Journal. Jun. 2001;80:2546-55.

Power et al., Computed tomography and patient risk: Facts, perceptions and uncertainties. World J Radiol. Dec. 28, 2016;8(12):902-915. doi: 10.4329/wjr.v8.i12.902.

Smith-Bindman et al., Radiation dose associated with common computed tomography examinations and the associated lifetime attributable risk of cancer. Arch Intern Med. Dec. 14, 2009;169(22):2078-86. doi: 10.1001/archinternmed.2009.427.

Stein, Indications for computed tomography after minor head injury. N Engl J Med. Nov. 23, 2000;343(21):1570.

Tran et al., CMOS-Compatible Silicon Nanowire Field-Effect Transistor Biosensor: Technology Development toward Commercialization. Materials (Basel). May 11, 2018;11(5):785. doi: 10.3390/ma11050785.

Unden et al., Scandinavian guidelines for initial management of minimal, mild and moderate head injuries in adults: an evidence and consensus-based update. BMC Med. Feb. 25, 2013;11:50. doi: 10.1186/1741-7015-11-50.

Wallentin et al., Hard X-ray detection using a single 100 nm diameter nanowire. Nano Lett. Dec. 10, 2014;14(12):7071-6. doi: 10.1021/nl5040545. Epub Dec. 1, 2014.

Zheng et al., Nanowire biosensors for label-free, real-time, ultrasensitive protein detection. Methods Mol Biol. Aug. 2011;790:223-37. Author manuscript provided. 15 pages.

\* cited by examiner

SENSOR SYSTEM AND ELECTRODES

RELATED APPLICATIONS

This application is a continuation of Ser. No. 17/330,206, filed May 25, 2021, entitled "SENSOR SYSTEM AND ELECTRODES", which is a divisional of U.S. application Ser. No. 17/131,657, filed Dec. 22, 2020, entitled "Sensor System and Electrodes", which claims priority under 35 U.S.C. § 119(e) to U.S. Provisional Application No. 62/953,140, filed Dec. 23, 2019, and entitled "Sensor System and Methods", to U.S. Provisional Application No. 62/953,143, filed Dec. 23, 2019, and entitled "Sensor System and Electrodes", and to U.S. Provisional Application No. 62/953,148, filed Dec. 23, 2019, and entitled "Sensor System and Methods of Making", each of which is incorporated herein by reference in its entirety.

FIELD

The present invention relates generally to sensors, and, more particularly, to sensors suitable for sensing bodily fluids.

BACKGROUND

Sensors may be employed to detect one or more features of bodily fluids. However, some sensors have undesirably low sensitivity to analytes of interest. Accordingly, improved sensors are needed.

SUMMARY

Sensors, related components, and related methods are generally described.

Some embodiments relate to sensors. In some embodiments, a sensor comprises a plurality of pairs of electrodes arranged to have radial symmetry around a center point. The plurality of pairs of electrodes comprises at least ten pairs of electrodes.

In some embodiments, a sensor comprises a plurality of nanowires arranged to form a circular structure about a center point and a plurality of electrodes disposed on the plurality of nanowires. The plurality of nanowires comprises at least 30 nanowires.

In some embodiments, a sensor comprises a pair of electrodes. The pair of electrodes comprises a first electrode comprising a first portion, a second portion, and a third portion connecting the first and second portion. The pair of electrodes also comprises a second electrode comprising a first portion substantially parallel to the first portion of the first electrode, a second portion substantially parallel to the second portion of the first electrode, and a third portion connecting the first and second portions. The first and second portions of the second electrode are positioned between the first and second portions of the first electrode.

In some embodiments, a sensor comprises a first electrode, a second electrode, and a nanowire. The nanowire is in electrical communication with the first electrode and the second electrode. A distance between the first electrode and the second electrode is greater than or equal to 5 microns and less than or equal to 15 microns. A ratio of a length of the nanowire to the distance between the first electrode and the second electrode is greater than or equal to 1 and less than or equal to 5.

In some embodiments, a sensor comprises a plurality of pairs of electrodes and a plurality of nanowires. For greater than or equal to 10% of the pairs of electrodes, the two electrodes making up the pair are in electrical communication by exactly one nanowire.

Some embodiments relate to methods. In some embodiments, a method comprises expelling a fluid comprising the plurality of nanowires from a nozzle onto the substrate, allowing at least a portion of the fluid to evaporate, replenishing at least a portion of the evaporated fluid by expelling a further amount of the fluid from the nozzle, and holding the fluid comprising the plurality of nanowires in contact with the substrate for a time period of greater than or equal to 0.2 sec. The fluid is in contact with both the substrate and the nozzle during the holding, replenishing and evaporation steps.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
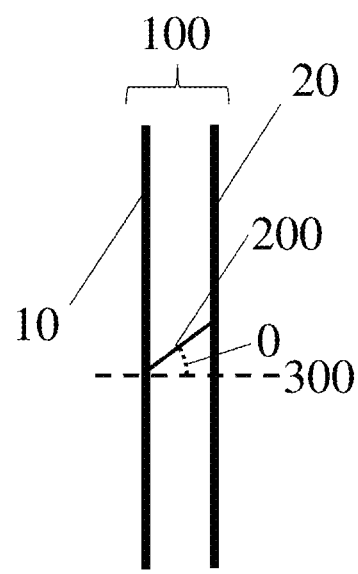
FIG. 1 shows a pair of electrodes in electrical communication by a single nanowire, in accordance with some embodiments.

Sensors, methods of fabricating sensors, and methods of using sensors to sense analytes are generally provided. In some embodiments, a sensor described herein has a design that enhances its sensitivity to one or more analytes of interest.

By way of example, a sensor may comprise a pair of electrodes in electrical communication via a component having high sensitivity to an analyte. For instance, a sensor may comprise a pair of electrodes in electrical communication by a nanowire. The nanowire may have a chemical composition that has a particularly high binding affinity for the analyte and/or may experience an appreciable change in equivalent surface potential upon binding with the analyte.

As another example, a sensor may comprise electrodes spaced at an advantageous distance from each other. The spacing may be selected to be large enough so that the electrodes may be electrically isolated from each other by an insulating material (e.g., large enough such that photolithography can be employed to form structures electrically isolating the electrodes) and small enough such that they can be placed in electrical communication by nanowires that can be commercially produced in sufficiently large quantities. In some embodiments, relatively large spacings between electrodes that are in electrical communication by nanowires may be achieved by employing fabrication processes that orient the nanowires to form an angle close to perpendicular with the electrodes. For instance, nanowires may be deposited onto a substrate to form coffee ring structures in which the nanowires are oriented tangentially to one or more circles. Such arrangements of nanowires may be particularly useful in combination with radially-arranged electrodes, as described in further detail elsewhere herein.

As a third example, a sensor may comprise a blocking layer. The blocking layer may be positioned between one or more components of the sensor and an environment external to the sensor. In some embodiments, a blocking layer prevents direct contact between one or more components of the sensor and a fluid to be analyzed by the sensor. The blocking layer may promote interaction between the sensor and a fluid to be analyzed by the sensor in a desired manner. For instance, it may reduce non-specific interactions between one or more components of the sensor and one or more components of the fluid to be analyzed and/or it may reduce charge screening between a fluid to be analyzed and the sensor. This may be particularly desirable for sensors designed to sense one or more analytes in fluids having a high ionic strength and/or comprising numerous components, such as bodily fluids.

As described above, some sensors described herein may have an arrangement of electrodes that facilitates the formation of a sensor in which two electrodes are in electrical communication by a nanowire. In some embodiments, it may be beneficial for the sensor to comprise two electrodes that are in electrical communication by exactly one nanowire, as electrodes in electrical communication by exactly one nanowire may have a resistivity thereacross that is predictable and/or may be highly sensitive to an analyte of interest. For instance, as described in the preceding paragraph, a sensor may comprise an arrangement of pairs electrodes in which the pairs of electrodes have radial symmetry around a center point. Pairs of electrodes having radial symmetry disposed on nanowires arranged to form a circular structure may be particularly likely to be connected by one such nanowire if the concentration of the nanowires in the circular structure(s) are appropriately selected.

In some embodiments, a sensor comprises electrodes having a design that facilitates the formation of a sensor having one or more desirable properties. By way of example, a sensor may comprise pairs of electrodes comprising an inner electrode nested inside of an outer electrode. Electrodes having this design may be twice as long as parallel electrodes of the same length, and so may have double the length available for a nanowire to place in electrical communication.

Some embodiments described herein relate to methods of fabricating sensors having one or more desirable properties. Such methods may comprise forming sensors by a process that results in the deposition of nanowires at a density and/or in an arrangement that is desirable. For instance, as described above, some methods may comprise forming one or more circular structures (e.g., coffee ring structures) of nanowires. The nanowires may be tangentially to the circular structure(s) and/or may be present in the circular structure(s) at advantageous densities. In some embodiments, a method comprises depositing nanowires from a fluid held in contact with a substrate. The fluid may at least partially evaporate and/or may be replenished while it is held in contact with the substrate. The evaporation and/or replenishment may be selected to promote the formation of coffee ring structure(s) (e.g., having a circular morphology) at desired locations, having desired radii, and/or having desired nanowire densities.

FIG. 1 shows one non-limiting embodiment of a pair of electrodes in electrical communication by a single nanowire. In FIG. 1, a pair of electrodes 100 comprises the electrodes 10 and 11. The electrodes 10 and 11 are in electrical communication by a nanowire 200. In some embodiments, like the embodiment shown in FIG. 1, a pair of electrodes comprises electrodes that are substantially parallel and/or comprises electrodes that comprise portions substantially parallel to each other. Electrodes (and/or portions therein) that are relatively parallel to each other may be oriented such that, if a line were drawn that intersected with both electrodes (and/or portions) in the pair, the angles that it would make with the two electrodes (and/or portions) in the pair would differ by a relatively small amount (e.g., less than or equal to 5°, less than or equal to 2°, less than or equal to 1°). In some embodiments, a pair of electrodes (and/or portions therein) that are relatively parallel to each other may be oriented such that the distance between each sub-portion of each electrode (and/or portion of each electrode) and the closest sub-portion thereto of the other electrode (and/or portion of the other electrode) varies by a relatively small amount (e.g., by less than or equal to 2 microns, less than or equal to 1.75 microns, less than or equal to 1.5 microns, less than or equal to 1.25 microns, less than or equal to 1 micron, less than or equal to 0.75 microns, or less than or equal to 0.5 microns). Additionally, it should also be understood that pairs of electrodes lacking substantially parallel portions are also contemplated.

A nanowire may place a pair of electrodes in electrical communication when it itself is in electrical communication with both members of the pair and when it provides a pathway through which current can flow between the pair of electrodes. This may be determined by applying a 0.1 V potential across the pair of electrodes and measuring the resultant current therebetween. If the resultant current is greater than or equal to 1 nA, then the pair of electrodes may be considered to be in electrical communication with each other.

In some embodiments, a nanowire that places two electrodes in electrical communication may be oriented such that it is at an angle to one or both electrodes that is close to 90°. With reference to FIG. 1, an angle (the angle 0) between a nanowire (the nanowire 200 in FIG. 1) and a direction perpendicular to an electrode (the direction 300 in FIG. 1 perpendicular to the electrode 10 in FIG. 1) may be relatively low. As described elsewhere herein, a nanowire having this property may be able to place electrodes in electrical communication that are spaced at a distance close to the length of the nanowire. This may advantageously allow for electrodes to be spaced apart at distances that allow them to be separated by photolithographic structures and/or may allow for the use of nanowires that have a length capable of being fabricated by commercial processes in an economical and/or relatively defect-free manner. However, it should also be understood that some nanowires may be oriented at a variety of angles to two electrodes that it places in electrical communication.

Figure 2:
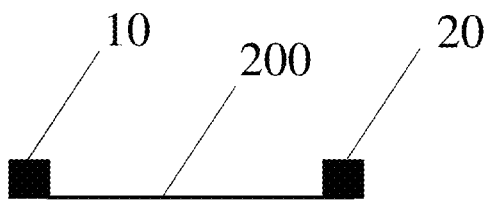
FIG. 2 shows a side view of a pair of electrodes, in accordance with some embodiments.

FIG. 2 shows a side view of the pair of electrodes shown in FIG. 1. Like in FIG. 2, some embodiments comprise a pair of electrodes disposed on a nanowire. It is also possible for a nanowire to be disposed on a pair of electrodes (e.g., alternatively to the pair of electrodes being disposed on the nanowire). Components disposed on each other as described herein and/or shown in the figures herein may be directly disposed on each other or may be indirectly disposed on each other. In other words, as used herein, when a component is referred to as being "disposed on" or "adjacent" another component, it can be directly disposed on or adjacent the component, or it may be disposed on one or more intervening components disposed on the other component. A component that is "directly disposed on", "directly adjacent" or "in contact with" another component means that it is disposed on the other component in a manner such that no intervening component is present.

Figure 3:
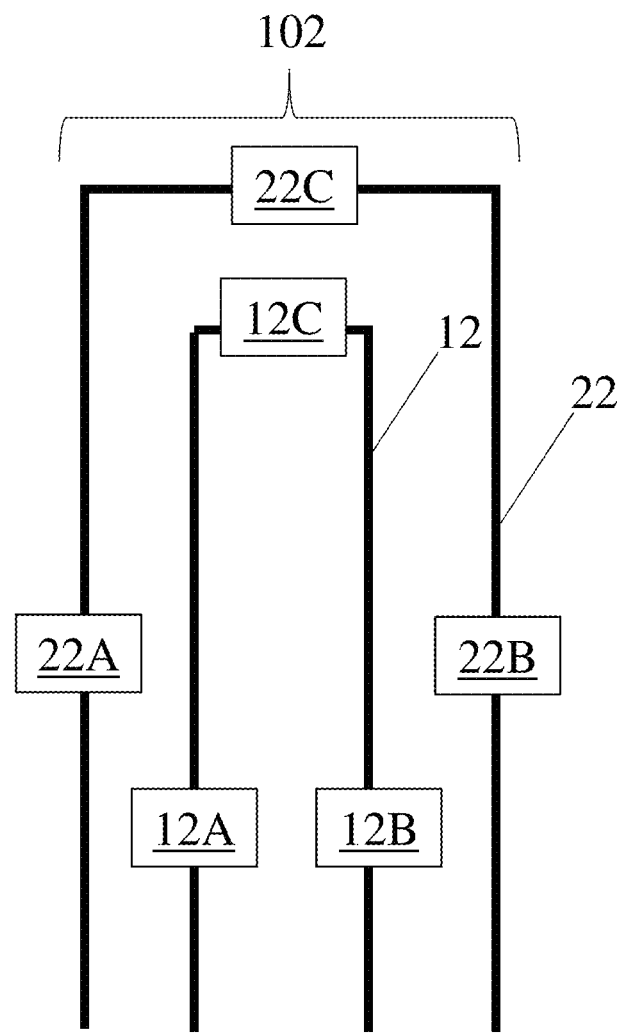
FIG. 3 shows a pair of electrodes, in accordance with some embodiments.
Figure 4:
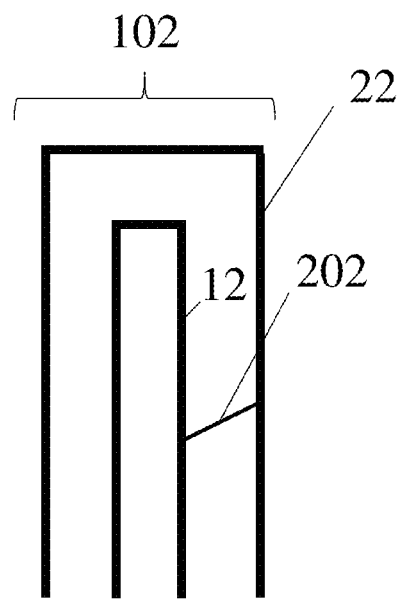
FIG. 4 shows a pair of electrodes in electrical communication by a single nanowire, in accordance with some embodiments.

FIG. 3 shows another possible electrode design. In FIG. 3, a pair of electrodes 102 comprises an electrode 12 (e.g., a first electrode) and an electrode 22 (e.g., a second electrode). Like the electrodes shown in FIGS. 1-2, electrodes having this design may also be in electrical communication by a nanowire (e.g., as shown in FIG. 4, in which these electrodes are electrically connected by a nanowire 202). The electrodes shown in FIGS. 3 and 4 each have three portions: a first and second portion that are substantially parallel to each other (the portions 22A and 22B of the electrode 22 and the portions 12A and 12B of the electrode 12 as shown in FIG. 3) and one portion connecting the first and second portions (the portion 22C of the electrode 22 and the portion 12C of the electrode 12 as shown in FIG. 3). As shown in FIGS. 3 and 4, the electrodes may be nested such that the first and second portions of the second electrode are positioned between the first and second portions of the first electrode (e.g., such that the portions 12A and 12B of the electrode 12 shown in FIG. 3 are positioned between the portions 22A and 22B of the electrode 22 shown in FIG. 3). Similarly, as is shown in FIGS. 3 and 4, the electrodes may be arranged such that portions of each electrode are parallel to portions of the other electrode. By way of example, with reference to FIG. 3, the portion 12A of the electrode 12 is parallel to the portion 22A of the electrode 22 and the portion 12B of the electrode 12 is parallel to the portion 22B of the electrode 22.

Figure 5:
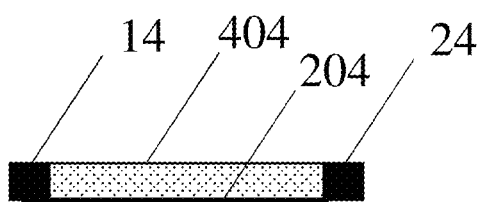
FIG. 5 shows a side view of a pair of electrodes in a sensor comprising a blocking layer, in accordance with some embodiments.

The electrodes described herein may be positioned in the sensors described herein. The sensors may further comprise one or more additional components. One example of such a component is a blocking layer. As described above, a blocking layer may be disposed on one or more portions of the sensor and/or may be configured to prevent direct contact between one or more portions of the sensor and environment external to the sensor. FIG. 5 shows one example of a side view of a pair of electrodes in a sensor comprising a blocking layer. In FIG. 5, the pair of electrodes 14 and 24 are in electrical communication by a nanowire 204. A blocking layer 404 is disposed over the nanowire 204. In some embodiments, the blocking layer may be the only layer positioned between a nanowire and an environment external to the sensor. Accordingly, it may mediate interactions between the environment external the sensor and the nanowire (e.g., between a fluid disposed on the sensor and the nanowire).

It should be understood that FIG. 5 is merely exemplary and that some blocking layers may differ from those shown in FIG. 5. For instance, some blocking layers may have different thicknesses with respect to the nanowire and/or the electrodes than the blocking layer shown in FIG. 5. As another example, some blocking layers may extend such that they are also at least partially disposed on one or both electrodes in a pair of electrodes. Similarly, it should be understood that some sensors may comprise further components than those shown in FIG. 5, non-limiting examples of which include substrates, surface layers, wire bonding pads, and/or further electrodes.

Figure 6A:
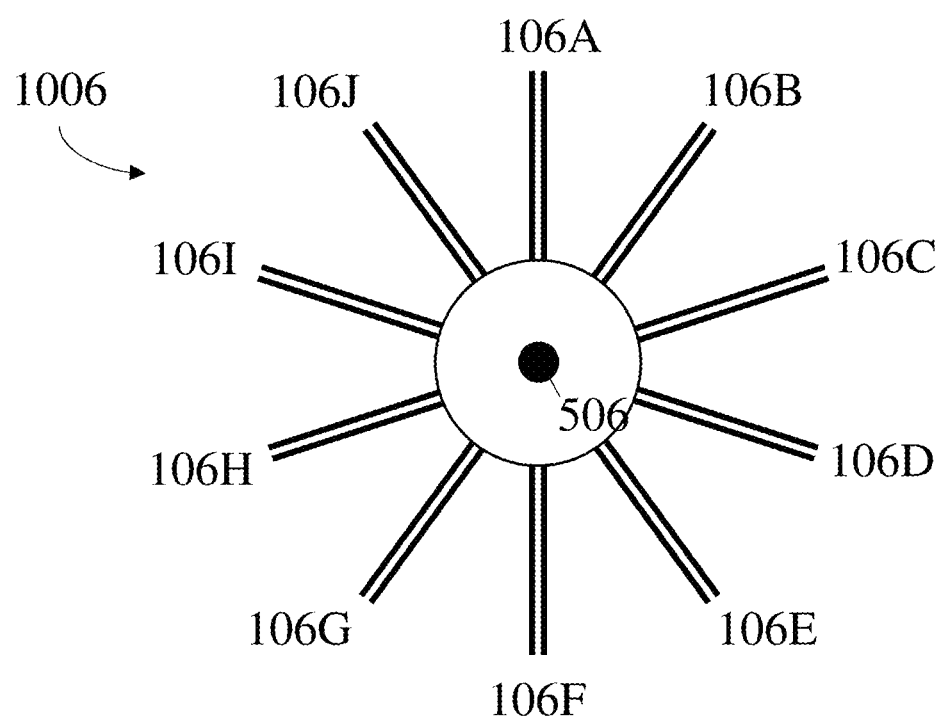
FIGS. 6A and 6B show sensors comprising pluralities of pairs of electrodes arranged to have radial symmetry around center points, in accordance with some embodiments.

In some embodiments, a sensor comprises a plurality of pairs of electrodes. Some of the pairs of electrodes may be in electrical communication (e.g., by a single nanowire, by more than one nanowire) and/or some of the pairs of electrodes may not be in electrical communication with one another. As described elsewhere herein, in some embodiments, a sensor comprises a plurality of pairs of electrodes arranged in a manner that promotes the formation of electrical communication between pairs of electrodes by a single nanowire. For instance, in some embodiments, a sensor comprises a plurality of pairs of electrodes arranged to have radial symmetry around a center point. FIG. 6A shows one non-limiting embodiment of a sensor having this property. In FIG. 6A, a sensor 1006 comprises pairs of electrodes 106A-106J arranged radially symmetrically around a center point 506. Some sensors may have one or more features like the sensor shown in FIG. 6A (e.g., some sensors may comprise exactly ten pairs of electrodes), and some sensors may differ from the sensor shown in FIG. 6A in one or more ways (e.g., some sensors may comprise a different number of pairs of electrodes, may comprise electrodes having a different design than the electrodes shown in FIG. 6A and/or may be spaced from the center point at distances other than those shown in FIG. 6A).

It should also be understood that the center point may lack any distinguishing feature (e.g., it may be the geometric center around which the electrodes are positioned in a radially symmetric manner, but otherwise have a chemistry and/or structure consistent with portions of the sensor to which it is adjacent) or may comprise one or more structural and/or chemical features distinguishing it from other portions of the sensor (e.g., it may comprise an electrode or other functional portion of the sensor).

Figure 6B:
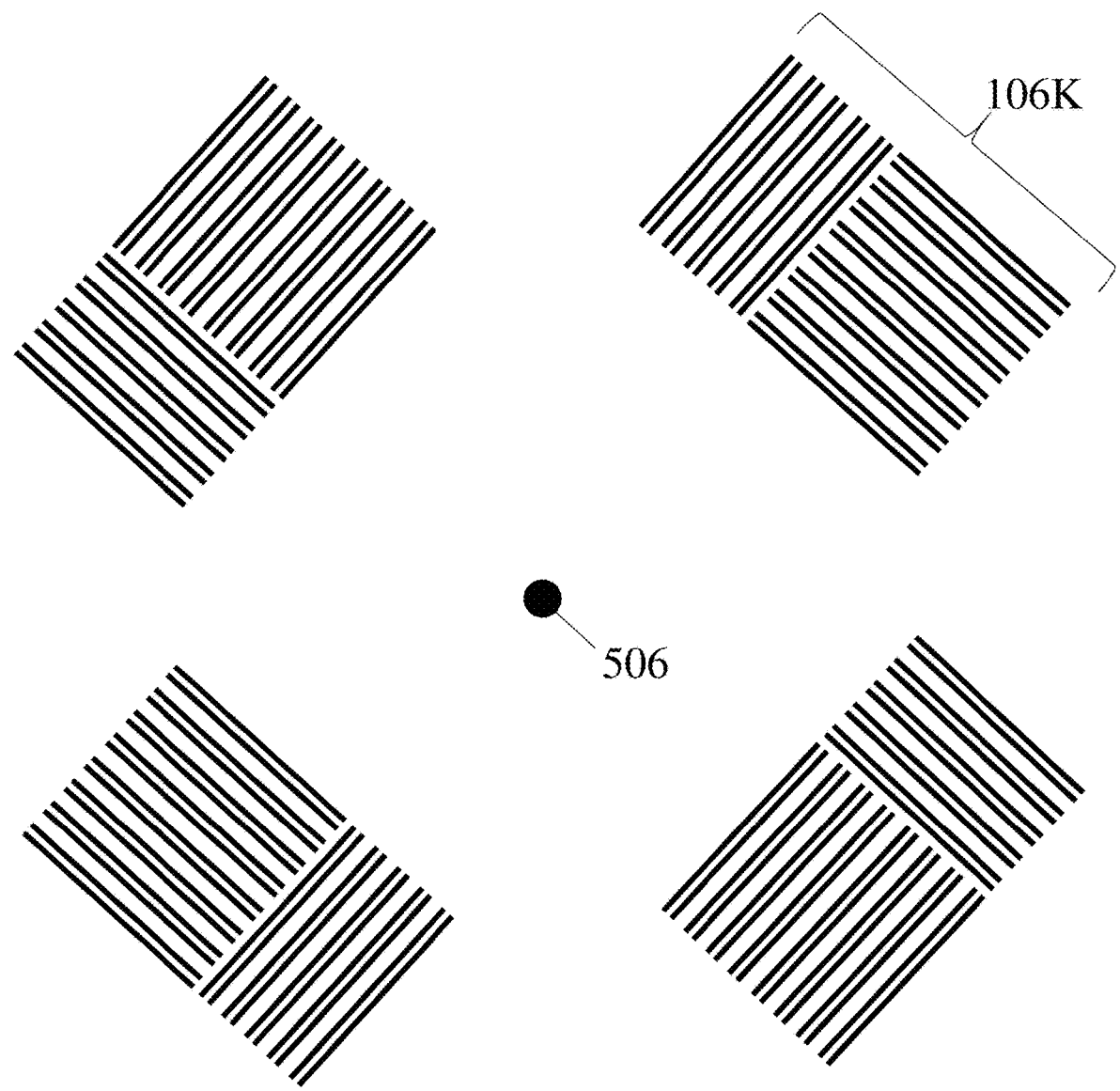

FIG. 6B shows another example of a sensor comprising a plurality of pairs of electrodes arranged to have radial symmetry around a center point. In FIG. 6B, a motif 106K comprising 13 pairs of electrodes is arranged to have radial symmetry around the center point 506. In embodiments in which a motif is arranged to have radial symmetry around a center point, the motif may comprise a variety of suitable numbers of pairs of electrodes. For instance, the motif may comprise two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more pairs of electrodes.

A plurality of pairs electrodes that have radial symmetry around a point may be positioned with respect to the point such that rotation of the pair of electrodes by a given angle (e.g., by 36° for ten electrodes that have radial symmetry) results in a plurality of pairs of electrodes having a structure substantially identical to the structure of the plurality of pairs of electrodes prior to rotation. In some embodiments, a plurality of pairs electrodes that have radial symmetry around a point comprises a structural motif (e.g., a pair of electrodes, a pair of electrodes exclusive of any leads connecting the pair of electrodes to another component of the sensor and/or an environment external to the sensor) that is positioned with respect to the point such that rotation of the pair of electrodes by a given angle (e.g., by 36° for ten electrodes that have radial symmetry) results in the structural motif being arranged substantially identically to the way that it was arranged prior to rotation. In some embodiments, a plurality of pairs of electrodes having radial symmetry may be positioned such that they (and/or a structural motif therein) are separated from each other by equal angles. By way of example, a plurality of electrodes may comprise ten pairs of electrodes, each of which are oriented with respect to their nearest neighbors such that rotation of any given pair of electrodes by 36° clockwise or counterclockwise around the center point would cause the pair of electrodes (and/or a structural motif therein) to substantially overlap with their clockwise or counterclockwise nearest neighbor, respectively. As another example, a plurality of electrodes may comprise twenty pairs of electrodes, each of which are oriented with respect to their nearest neighbors such that rotation of any given pair of electrodes by 18° clockwise or counterclockwise around the center point would cause the pair of electrodes (and/or a structural motif therein) to substantially overlap with their clockwise or counterclockwise nearest neighbor, respectively.

As can be seen from FIGS. 6A and 6B, some pluralities of pairs of electrodes that are arranged to have radial symmetry around a center point are made up of pairs electrodes that oriented with respect to the center point in a manner such that each pair of electrodes can be mapped onto each other pair of electrodes by rotation around the center point and some pluralities of pairs of electrodes comprise at least some pairs of electrodes that cannot be mapped onto other pairs of electrodes by such rotation. In some embodiments, a plurality of pairs of electrodes forms a plurality of structural motifs that have radial symmetry around a center point such that each structural motif can be mapped onto each other structural motif by rotation around the center point.

In some embodiments, a plurality of pairs of electrodes have a type of symmetry other than radial (e.g., in addition to radial symmetry, instead of radial symmetry). For instance, in some embodiments, a plurality of pairs of electrodes has reflection symmetry. In such cases, the plurality of pairs of electrodes may be positioned with respect to one or more mirror planes such that reflection of the pair of electrodes across the mirror plane(s) results in a plurality of pairs of electrodes having a structure substantially identical to the structure of the plurality of pairs of electrodes prior to reflection. Similarly, the plurality of pairs of electrodes may comprise a structural motif (e.g., a pair of electrodes, a pair of electrodes exclusive of any leads connecting the pair of electrodes to another component of the sensor and/or an environment external to the sensor) that is positioned with respect to one or more mirror planes such that reflection of the pair of electrodes across the mirror plane(s) does not change the arrangement of the structural motifs.

Additionally, some sensors may comprise a plurality of pairs of electrodes that is equidistant from a center point but not necessarily radially symmetric about the center point. As an example, a sensor may comprise a plurality of pairs of electrodes that is positioned to be equidistant from the center point but not positioned equiangularly around the center point. For instance, a sensor may comprise four electrodes and each electrode may comprise one nearest neighbor from which it is separated by a rotation of less than 90° (e.g., less than or equal to 85°, less than or equal to 80°, less than or equal to 85°, less than or equal to 70°, less than or equal to 75°, less than or equal to 60°) and/or one nearest neighbor from which it is separated by a rotation of greater than 90° (e.g., greater than or equal to 95°, greater than or equal to 95°, greater than or equal to 100°, greater than or equal to 105°, greater than or equal to 110°, greater than or equal to 115°, or greater than or equal to 120°). As another example, a sensor may comprise a plurality of structural motifs comprising one or more pairs of electrodes (e.g., as shown in FIG. 6B) that are positioned equidistantly from a center point but not radially symmetrically about the center point. For instance, a sensor may comprise four such structural motifs and each structural motif may comprise one nearest neighbor from which it is separated by a rotation of less than 90° and/or one nearest neighbor from which it is separated by a rotation of greater than 90°. For instance, with respect to FIG. 7E, the angle 6 may be a value other than 90° (e.g., less than 90° or greater than 90°).

In some embodiments, a sensor comprises a plurality of electrodes that are equidistant from a center point but lack an angle of less than 360° through any given pair of electrodes can be rotated to overlap with another plurality of electrodes. This may be due to differing orientations of the electrodes, different shapes of the electrodes and/or different sizes of the electrodes. Similarly, a sensor may comprise a plurality of structural motifs comprising one or more pairs of electrodes that are equidistant from a center point but lack an angle of less than 360° through any given motif can be rotated to overlap with another structural motif. This may be due to differing orientations of the structural motifs and/or electrodes therein, different shapes of the structural motifs and/or electrodes therein and/or different sizes of the structural motifs and/or electrodes therein.

Additionally, a sensor may comprise a plurality of pairs of electrodes and/or a plurality of structural motifs that are not equidistant from a center point that are positioned within a range of distances from the center point. For instance, as described in further detail below, the plurality of pairs of electrodes and/or plurality of structural motifs may be positioned within a range of distances from the center points that overlaps (e.g., partially, fully) with a circular structure comprising a plurality of nanowires.

Figure 7A:
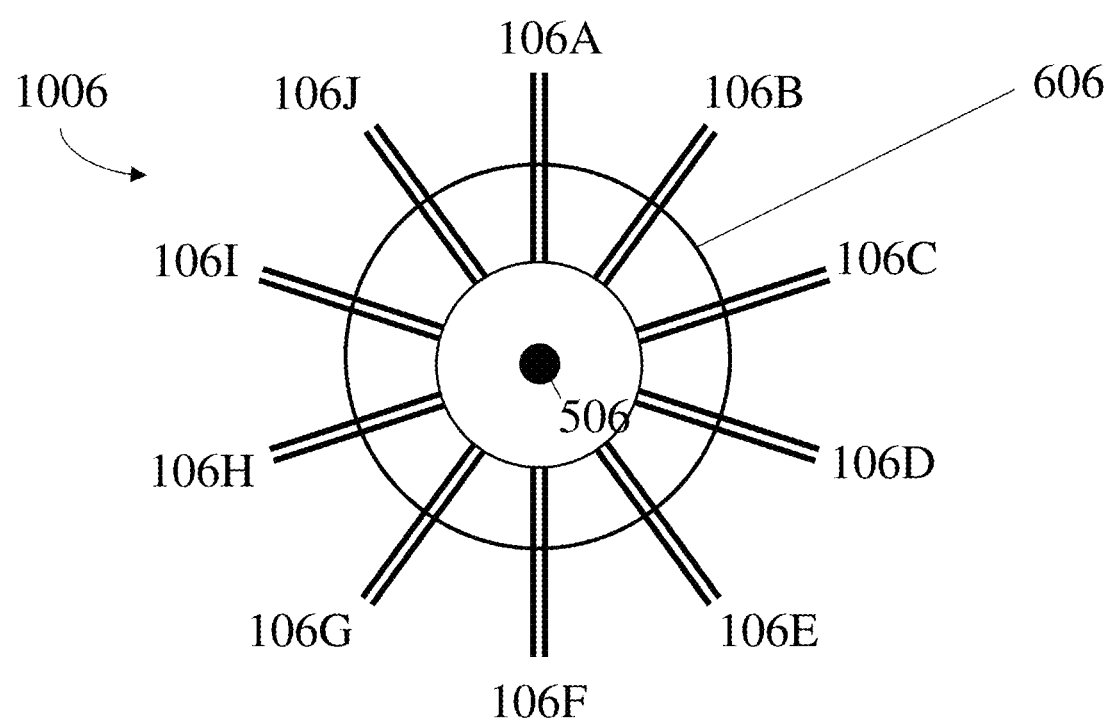
FIGS. 7A-7E shows sensors comprising pluralities of pairs of electrodes that are disposed on circular structures comprising pluralities of nanowires, in accordance with some embodiments.
Figure 7B:
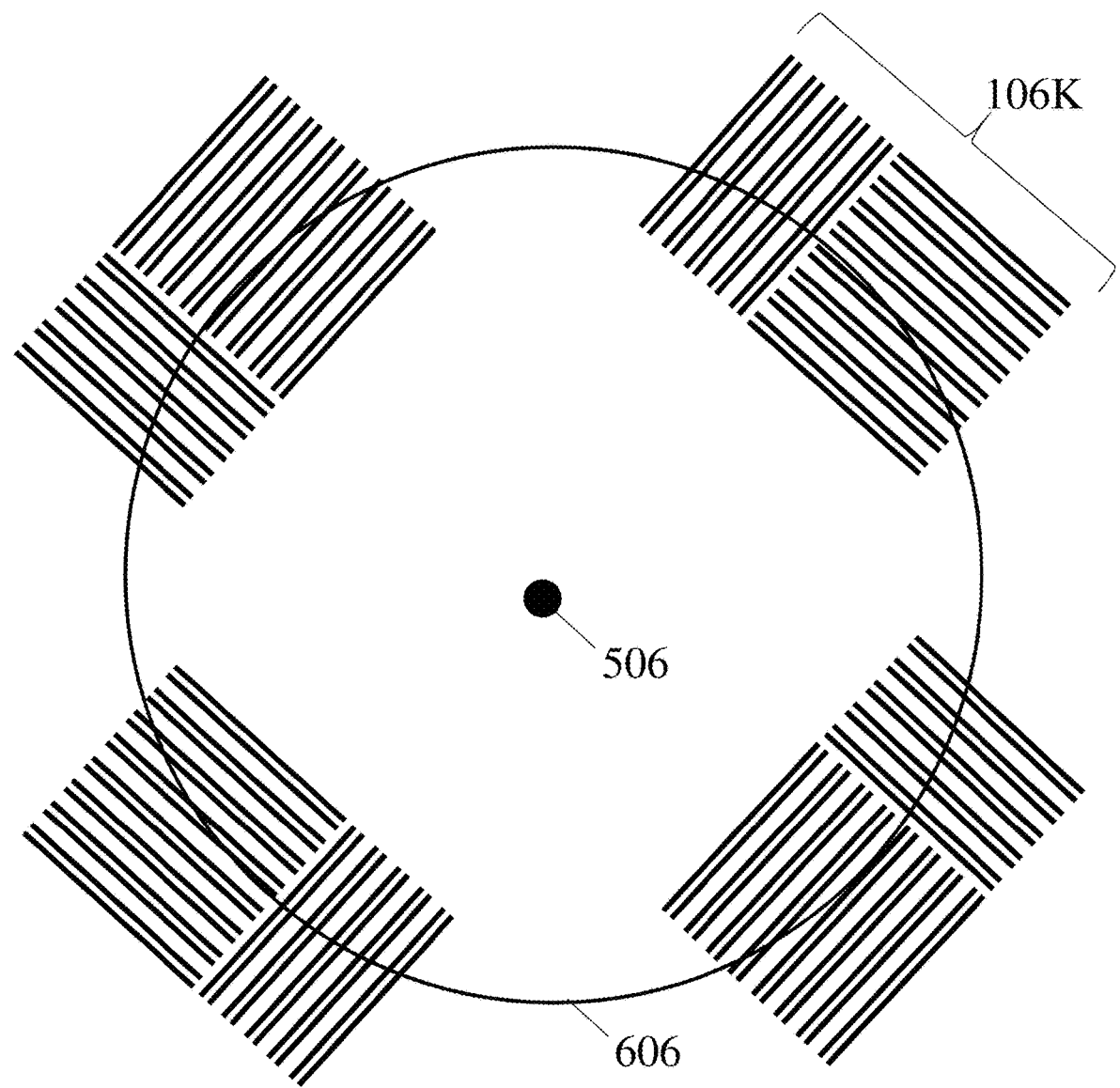

As shown in FIGS. 7A and 7B, it is also possible for a sensor to comprise a plurality of pairs of electrodes that are disposed on a circular structure comprising and/or formed from a plurality of nanowires (e.g., on the circular structure 606 shown in FIGS. 7A and 7B). As shown in FIGS. 7A and 7B, such electrodes may have radial symmetry around a center point. The circular structure may also have radial symmetry around this same center point and/or may comprise pairs of electrodes positioned equidistantly from this same center point. In some embodiments, at least a portion of the nanowires forming the circular structure may be oriented substantially tangentially to the circular structure. As described elsewhere herein, such nanowires may intersect one or more electrodes at an angle close to 90° and/or may be in electrical communication with two electrodes in a pair of electrodes while also having a length relatively close to the distance therebetween. It is also possible for the nanowires in a circular structure to be oriented randomly therein and/or for one or more portions of the nanowires in the circular structure to be oriented randomly (e.g., in addition to one or more portions oriented substantially tangentially to the circular structure). It should be understood that references to "circular structures" herein may refer to structures that form a perfect geometric circle or may refer to structures that form a shape close to a perfect geometric circle but that differ insubstantially from a perfect geometric circle in one or more ways.

Figure 7C:
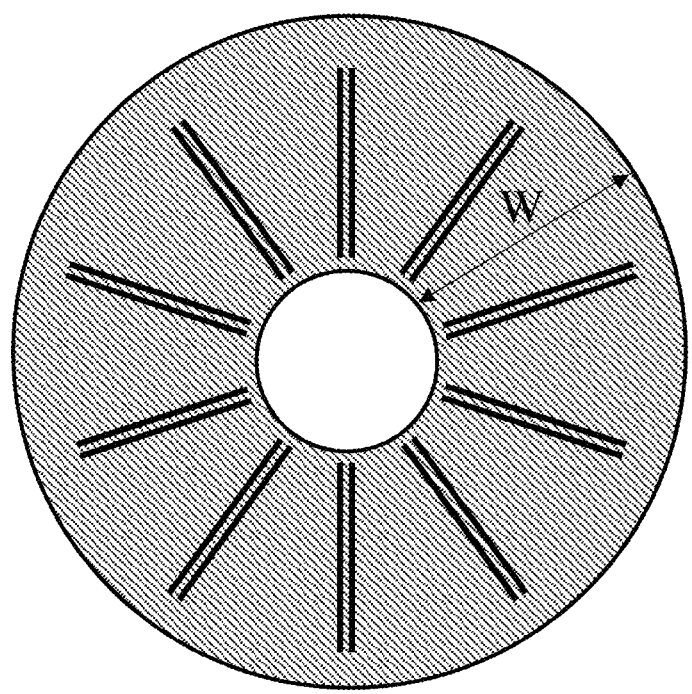
Figure 7D:
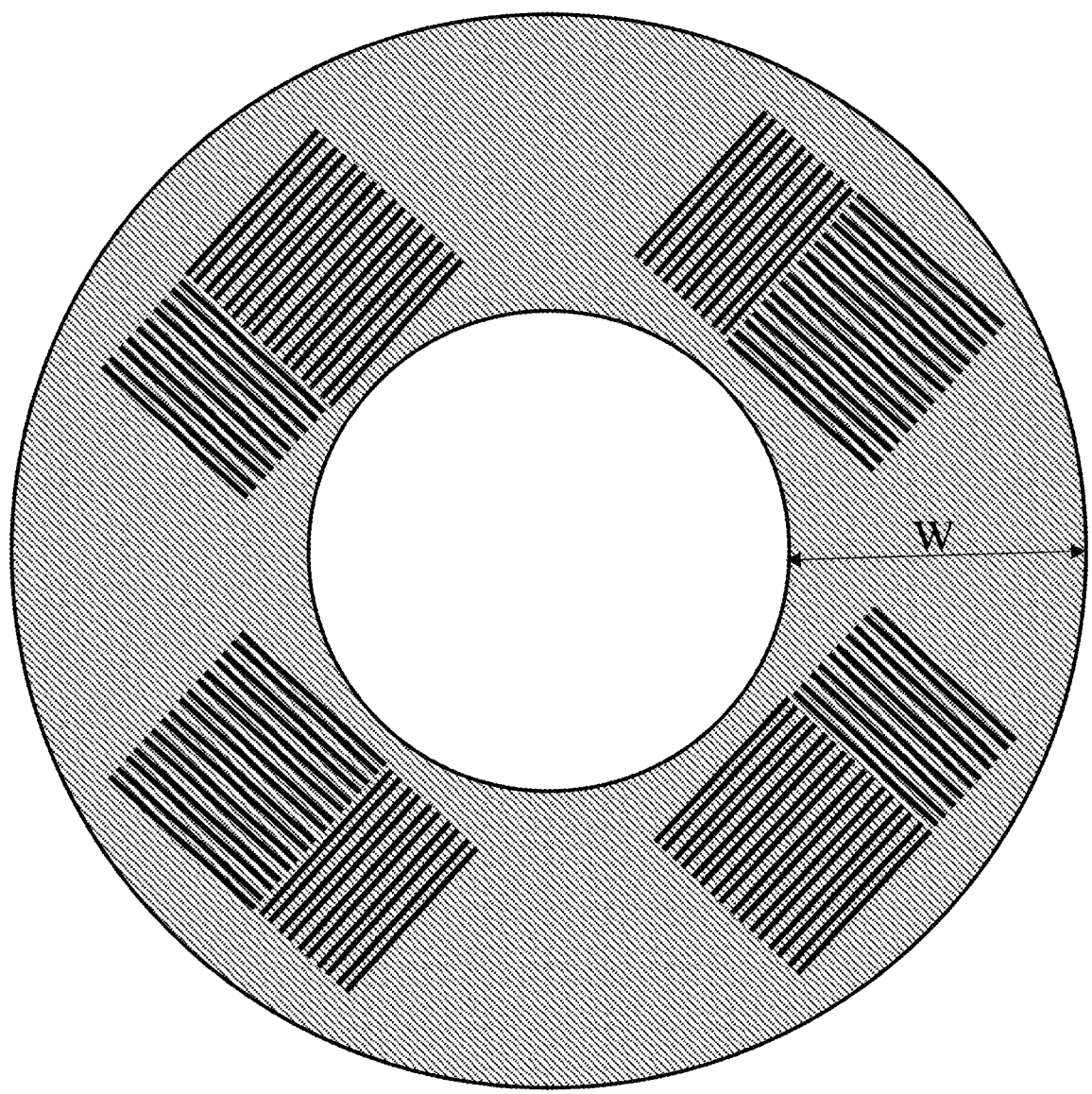

Although the circular structures shown in FIGS. 7A and 7B have relatively small widths in comparison to the pluralities of pairs of electrodes also shown therein, it is also possible for circular structures to have widths that are on the order of the sizes of these pluralities of pairs of electrodes and/or motifs formed by these pluralities of pairs of electrodes. For instance, FIGS. 7C and 7D show circular structures having widths that are large enough to cover the pluralities of electrodes shown therein. These widths are labeled W in both of these figures.

Figure 7E:
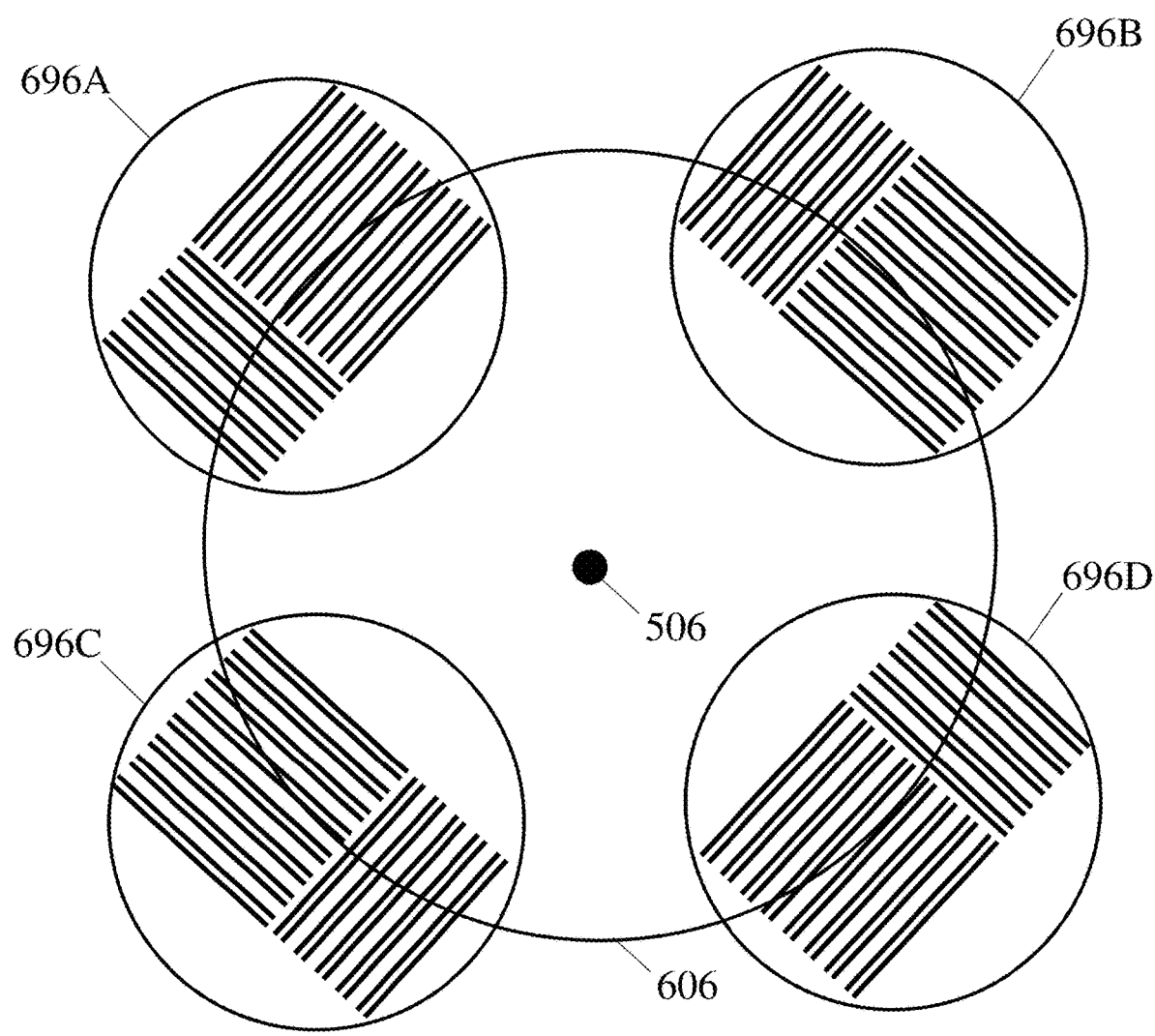

In some embodiments, a sensor described herein may be configured to sense a single analyte. In such embodiments, all of the nanowires may be functionalized to have a single type of chemistry (e.g., a single type of functional group, a single type of binding entity). Other sensors may be configured to sense two or more analytes. Such sensors may comprise two or more groups of nanowires that are functionalized with different chemistries (e.g., different types of functional groups, different types of binding entities). In some embodiments, a plurality of pairs of electrodes may be arranged such that there are groups of electrodes that correspond to groups of nanowires that are functionalized with different chemistries. Such groups of electrodes may comprise a number and/or arrangement of electrodes that results in a relatively high number of electrodes in electrical communication with each other by the nanowires in the relevant group and/or that results in a relatively small (or zero) number of electrodes in electrical communication with each other by nanowires outside the relevant group. Such groups of electrodes may have shapes that roughly correspond to the areas over which the species employed to functionalize the nanowires can be facilely dispensed. For instance, FIG. 7E shows four examples of areas over which the species employed to functionalize the nanowires can be facilely dispensed (the areas 696A, 696B, 696C, and 696D). As can be seen from FIG. 7E, a group of electrodes is positioned within each area. These areas may also have radial symmetry about a center point, be positioned equidistantly from a center point, and/or be positioned within a range of distances from a center point (e.g., the same center point about which a plurality of pairs of electrodes and/or structural motifs has radial symmetry, the same center point about which a circular structure of nanowires has radial symmetry)

It should be understood that sensors having designs similar to those shown in FIGS. 6 and 7 may comprise electrodes having a variety of suitable designs. In some embodiments, the pairs of electrodes have a design similar to that shown in FIG. 3. It is also possible for the pairs of electrodes to have a design similar to that shown in FIG. 1 (e.g., the sensor may comprise an array of linear electrodes positioned such that their long axes are next to each other).

Figure 8A:
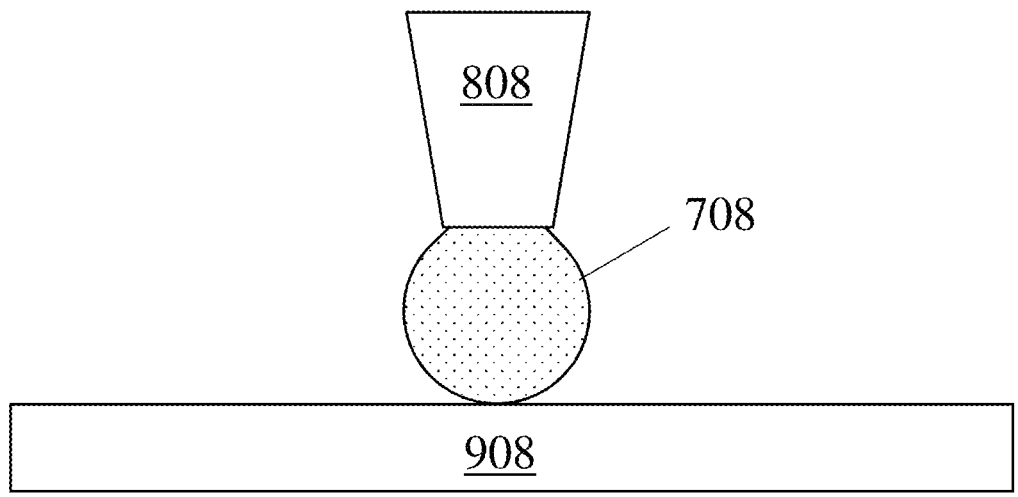
FIGS. 8A-8E show several steps that may be performed during sensor fabrication, in accordance with some embodiments.
Figure 8B:
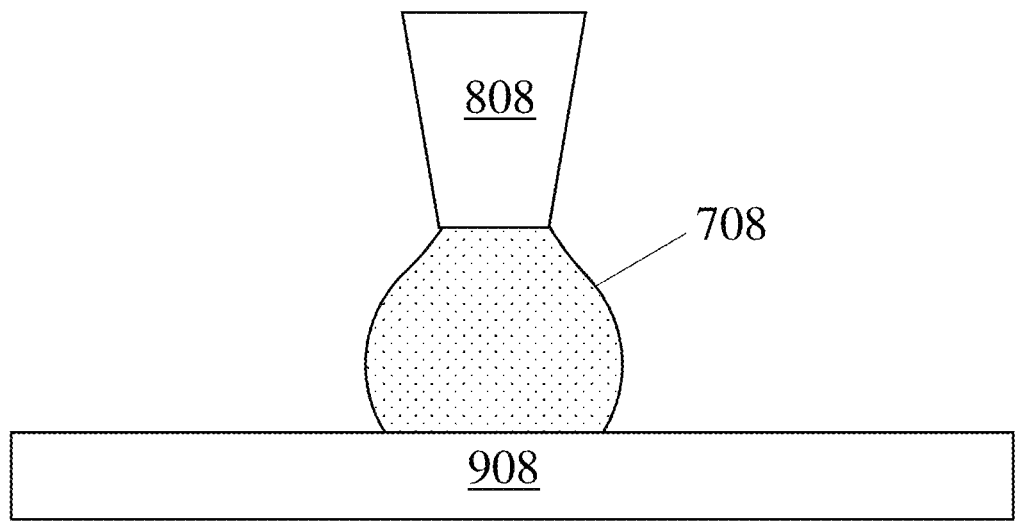
Figure 8C:
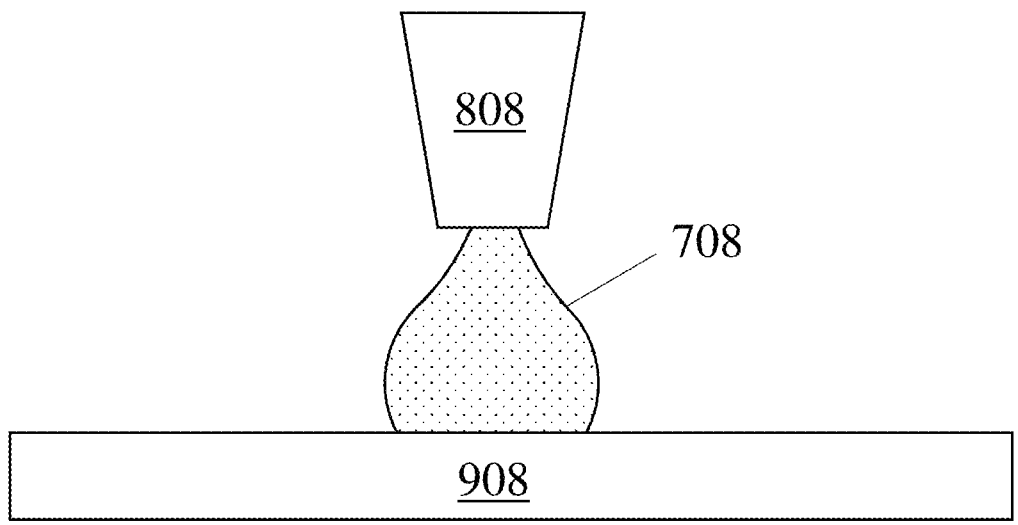
Figure 8D:
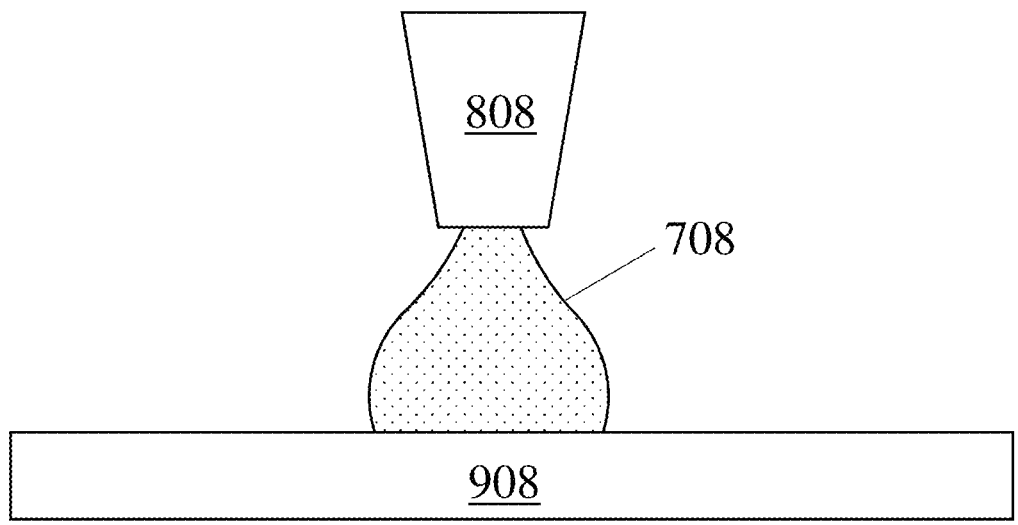
Figure 8E:
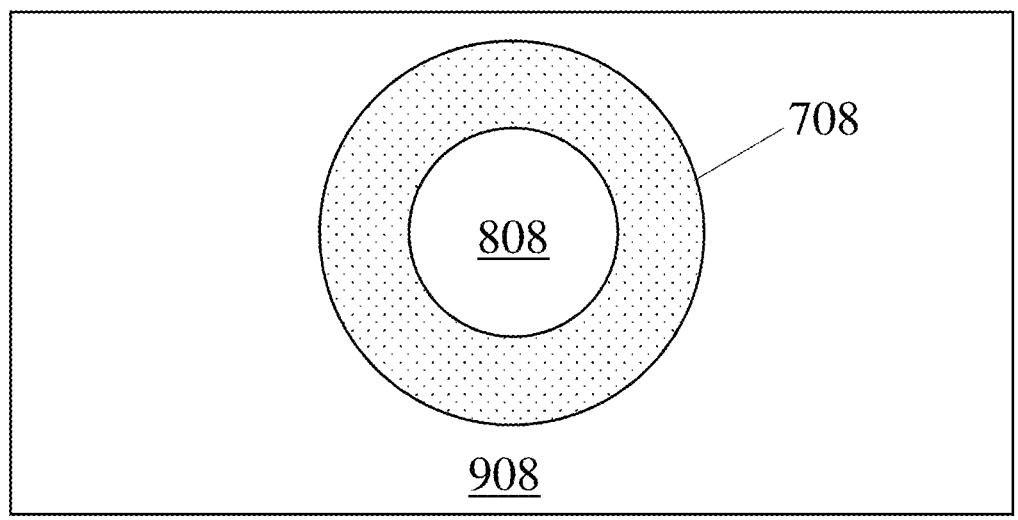

As described elsewhere herein, some embodiments relate to methods of fabricating sensors and/or methods that may be performed during the fabrication of sensors (e.g., sensors having one or more of the features described herein). FIGS. 8A-8D show one method that may be performed during sensor fabrication (e.g., in combination with other, further steps). The method shown in FIGS. 8A-8D depicts one manner in which a plurality of nanowires may be deposited onto a substrate. The method comprises expelling a fluid comprising the plurality of nanowires from a nozzle and holding the fluid comprising the plurality of nanowires in contact with both the substrate and the nozzle for a finite period of time. During this finite period of time, at least a portion of the fluid is allowed to evaporate and is replenished by further fluid from the nozzle. FIGS. 8A-8B shows the expulsion of a fluid 708 comprising a plurality of nanowires from a nozzle 808 onto a substrate 908. FIG. 8C shows the fluid 708 comprising the nanowires after partial evaporation, and FIG. 8D shows the fluid 708 comprising the nanowires after replenishment. FIG. 8E shows a top view of FIG. 8D. Although FIGS. 8C and 8D show fluid evaporation and replenishment as distinct steps, it should be understood that both may occur simultaneously. For instance, fluid from the fluid comprising nanowires may be continually evaporating throughout the process shown in FIGS. 8A-8D. As another example, the fluid may be continually replenished throughout the process shown in FIGS. 8A-8D and/or may be replenished at discrete times (e.g., periodically) during which evaporation also occurs.

The method shown in FIGS. 8A-8D may be advantageous for forming circular structures comprising nanowires at advantageous locations and/or oriented at advantageous angles. Without wishing to be bound by any particular theory, it is believed that this method may be suitable for forming such structures due to the coffee ring effect. The coffee ring effect may occur when fluid comprising a solid (in some embodiments described herein, a plurality of nanowires) at least partially evaporates at its surface (e.g., at an interface between the fluid and air). As the fluid evaporates from its surface, the solid suspended and/or dissolved therein does not evaporate and so may become increasingly concentrated at the surface of the fluid. Additionally, evaporation of a fluid from its surface may cause further transport of fluid from its interior to its surface, transporting further solids from the interior of the fluid to its surface. This is believed to result in the formation of a relatively large concentration of the solid at the external boundary of the fluid at which evaporation occurs (e.g., an interface between the fluid and air; an interface between the fluid, air, and a substrate on which the fluid is disposed; an outer rim of the fluid). If the fluid is pinned at a particular location on a substrate during such evaporation (e.g., due to surface tension), a coffee ring or circular structure comprising the solids therein (e.g., nanowires) disposed on that location may form after evaporation of the fluid.

The methods described herein, such as the method shown in FIGS. 8A-8D may be suitable for forming coffee ring structures or circular structures at desired locations because they may allow for placement of the surface of the fluid from which evaporation may occur (and, in some embodiments, the associated placement of solids therein on a substrate on which the fluid is disposed during evaporation). For instance, the initial volume of the fluid comprising the plurality of nanowires may be selected such that the outer boundary of the fluid on the substrate is at a location where it is desirable for a coffee ring and/or circular structure to form. As another example, the initial concentration of the nanowires in the fluid, the rate at which the fluid is replenished, and/or the total amount of fluid evaporated may be selected such that the coffee ring and/or circular structure that forms has a desirable density of nanowires. In some embodiments, the rate at which the fluid evaporates may be adjusted (e.g., by selection of the fluid, by temperature of the substrate) to promote formation of a coffee ring or circular structure having one or more desirable properties. Combinations of the above-mentioned parameters may be varied to tailor the deposition of the plurality of nanowires.

As described herein, in some embodiments a method may involve forming a circular structure comprising a plurality of nanowires. The method may also involve forming a plurality of pairs of electrodes (e.g., at least ten pairs of electrodes) arranged to have radial symmetry around a center point such that at least one nanowire is in electrical communication with one pair of electrodes. As a result, in some embodiments, a sensor comprises a plurality of nanowires arranged to form a circular structure (e.g., a circular structure having radial symmetry around a center point) and a plurality of electrodes disposed thereon (e.g., a plurality of electrodes also having radial symmetry around the same center point). In some embodiments, for greater than or equal to 10% of the pairs of electrodes, the two electrodes making up the pair are in electrical communication by exactly one nanowire.

In some embodiments, a plurality of nanowires is deposited onto a substrate that has been plasma etched (e.g., as described elsewhere herein). The plasma etching may advantageously enhance the uniformity of the surface thereof. In the case of a silicon substrate, the plasma etching may cause the formation of hydroxyl groups that enhance bonding between the plurality of nanowires and the substrate surface.

As described above, some embodiments relate to sensors comprising components other than those shown in FIGS. 1-7 (e.g., in addition to the components shown in one or more of FIGS. 1-7) and/or relate to methods of fabricating sensors comprising steps other than those shown in FIGS. 8A-8D (e.g., in addition to the steps shown in FIGS. 8A-8D). An overview of one set of steps by which a sensor can be fabricated is provided below. The components that the sensor may comprise are introduced below in combination with a step by which they may be fabricated. However, it should be understood that some sensors may comprise such component(s) but that the component(s) may be fabricated in a manner other than that described. It should also be understood that some sensors may comprise all of the components below, some sensors may comprise a subset of the components below, and/or some sensors may comprise components other than those described below. Similarly, it should be understood that some methods may comprise all of the steps below, some methods may comprise a subset of the steps below, and/or some methods may comprise steps other than those described below.

In some embodiments, a sensor is disposed on a substrate. Some substrates naturally and/or by design comprise a layer disposed thereon having a different chemical composition than the substrate bulk. It may be desirable to remove at least a portion of this surface layer from the substrate so that one or more components of the sensor may be fabricated directly on the substrate and/or so that portion(s) of the substrate uncovered by a surface layer may serve as fiducial alignment marks. Direct fabrication of one or more components of the sensor on the substrate may be employed when it is desirable for the relevant component(s) to be in direct electrical communication with the substrate, such as when the substrate is employed as a gating electrode and/or when the substrate is grounded. Fiducial alignment marks may be employed during further sensor fabrication steps to ensure that the processes performed are performed at the correct location(s) on the substrate. For instance, the location(s) at which further sensor fabrication steps are be performed may be determined with reference to one or more fiducial alignment marks. If multiple steps are performed at location(s) at known distances from the fiducial alignment mark(s), they may thus be performed at known distances from each other.

Figure 9A:
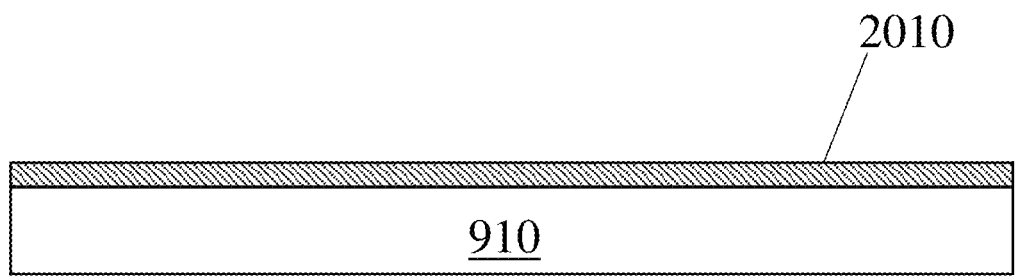
FIGS. 9A-9B show one method of removing a portion of a surface layer from a substrate, in accordance with some embodiments.
Figure 9B:
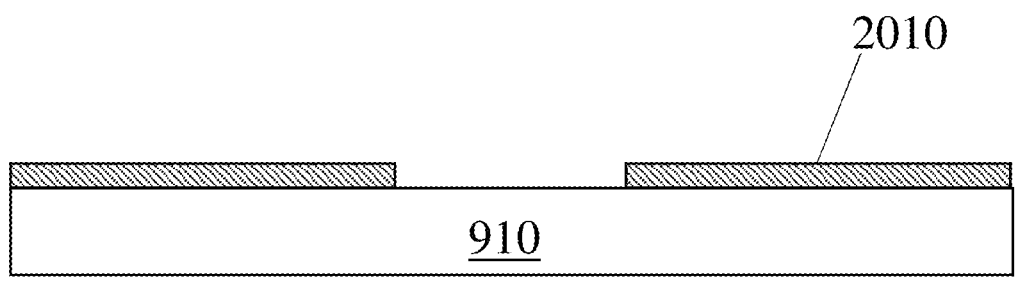

FIGS. 9A-9B show one method of removing a portion of a surface layer from a substrate. In FIGS. 9A-9B, a portion of a surface layer 2010 is removed from a substrate 910 to form an article comprising a substrate on which a surface layer is partially disposed. In some embodiments, such a process may be performed to form an article in which one or more portions of the substrate is/are covered by a surface layer and one or more portions of the substrate is/are uncovered by a surface layer (e.g., they may be directly exposed to an environment external to the substrate). Such a process may also be formed to remove the entirety of a surface layer from a substrate (not shown).

A surface layer may be removed from a substrate by a variety of suitable techniques. In some embodiments, an etching technique may be used, non-limiting examples of which include wet etching techniques and dry etching techniques. Wet etching techniques may comprise exposing the substrate to a wet etchant. One example of a suitable wet etchant is a solution comprising an acid (e.g., hydrofluoric acid) and a buffering agent (e.g., ammonium fluoride). The acid and the buffering agent may be mixed at a variety of ratios, such as a 1:6 buffering agent:acid ratio. Another example of a suitable wet etchant is an acid (e.g., hydrofluoric acid). Dry etching techniques may comprise exposing the substrate to a dry etchant, such as a reactive plasma (e.g., a reactive oxygen plasma). The plasma may be generated by exposing a low pressure environment to an electromagnetic field to generate high energy ions. The high energy ions may attack the passivating layer and etch it away. In one exemplary embodiment, a plasma etch is performed by exposing the substrate to an oxygen plasma at a pressure of 1 Torr and a power of 50 W in a Plasmalin 115 plasma etcher.

The time for which an etching technique may be performed may be selected such that the surface layer is removed but that the underlying substrate is not appreciably etched. For this reason, it may vary with the thickness of the surface layer. For the case of a solution comprising an acid and a buffering agent, which may remove a surface layer at a rate of approximately 100 nm/minute, a suitable exposure time of the substrate to the solution in minutes may be determined by dividing the thickness of the surface layer in nanometers by 100.

When an etching process is performed to remove a portion, but not all, of a surface layer, the portions of the surface layer designed to be retained may be protected from exposure to the etchant during the etching process. In some embodiments, the portion(s) of the surface layer designed to be retained may be covered by a photoresist during the etching process while the portion(s) of the surface layer designed to be removed may be free from the photoresist. After the etching process, the remainder of the photoresist may be removed. Suitable photoresists (and associated methods of patterning photoresists) include those described elsewhere herein as options for forming photoresist layers to be included in the final sensor (e.g., photoresists that may be patterned by selective exposure to light and then subsequent development, such as AZ-5214E-IR, SU8).

It should also be noted that some sensors may comprise fiducial alignment marks other than those formed by etching away portions of a passivating layer disposed on a substrate. By way of example, some sensors may comprise fiducial alignment marks formed by depositing a material on a substrate. Non-limiting examples of suitable such materials include metals (e.g., nickel, chromium, gold, titanium, platinum, aluminum, alloys thereof, combinations thereof).

As described above, some embodiments may comprise a plurality of nanowires disposed on a substrate. The plurality of nanowires may be deposited on the substrate after at least a portion of a surface layer disposed on the substrate has been removed therefrom and/or after fiducial alignment marks have been formed thereon. In some embodiments, the plurality of nanowires are deposited onto a surface layer disposed on a substrate.

As also described above, some embodiments may comprise pairs of electrodes disposed on a substrate. The pairs of electrodes may be disposed on the substrate (e.g., directly on a surface layer disposed thereon) and/or may be disposed on a portion of the plurality of nanowires (e.g., directly thereon). A variety of suitable techniques may be employed to deposit a pair of electrodes on a substrate. In some embodiments, a pair of electrodes is deposited on a substrate by vapor deposition. Prior to vapor deposition of the electrodes, a photoresist may be deposited onto the substrate and selectively removed from locations at which the electrodes are to be deposited. By way of example, a photoresist may be deposited onto the substrate, exposed to light (e.g., UV light) through a mask at the locations at which the pairs of electrodes are to be deposited, and then exposed to a developer. The developer may remove the portions of the photoresist exposed to the light. Then, the material forming the pairs of electrodes may be deposited onto both the photoresist and the exposed nanowires and/or substrate therebeneath. This material forming the pairs of electrodes may thus deposit directly onto the nanowires and/or substrate in the locations where the photoresist has been removed.

Figure 10A:
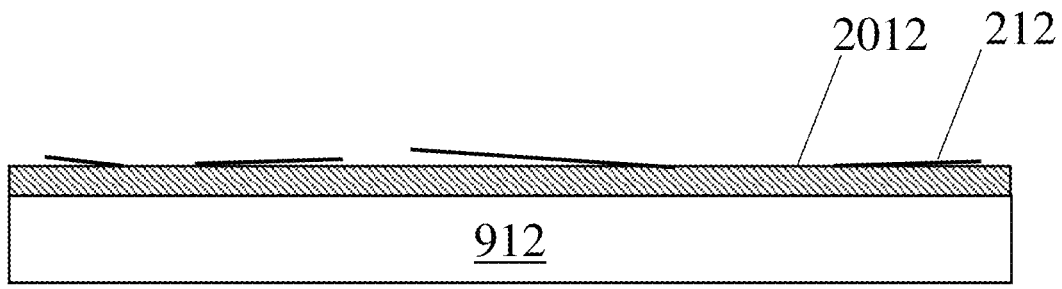
FIGS. 10A-10E show one method of depositing a pair of electrodes on a substrate on which a plurality of nanowires is disposed, in accordance with some embodiments.
Figure 10B:
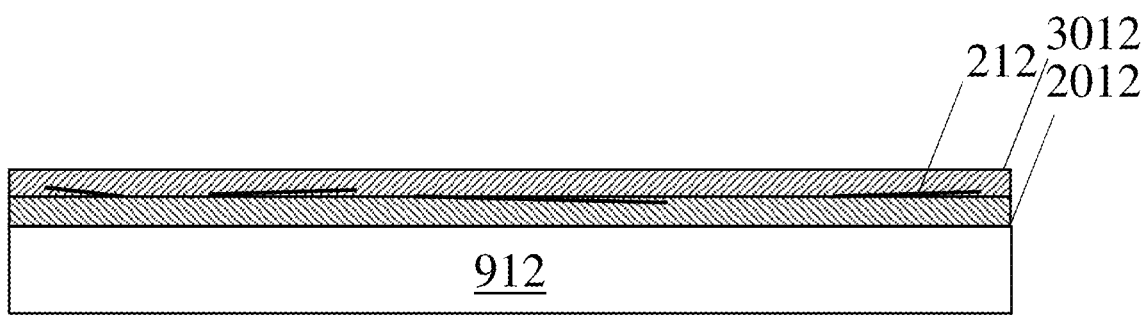
Figure 10C:
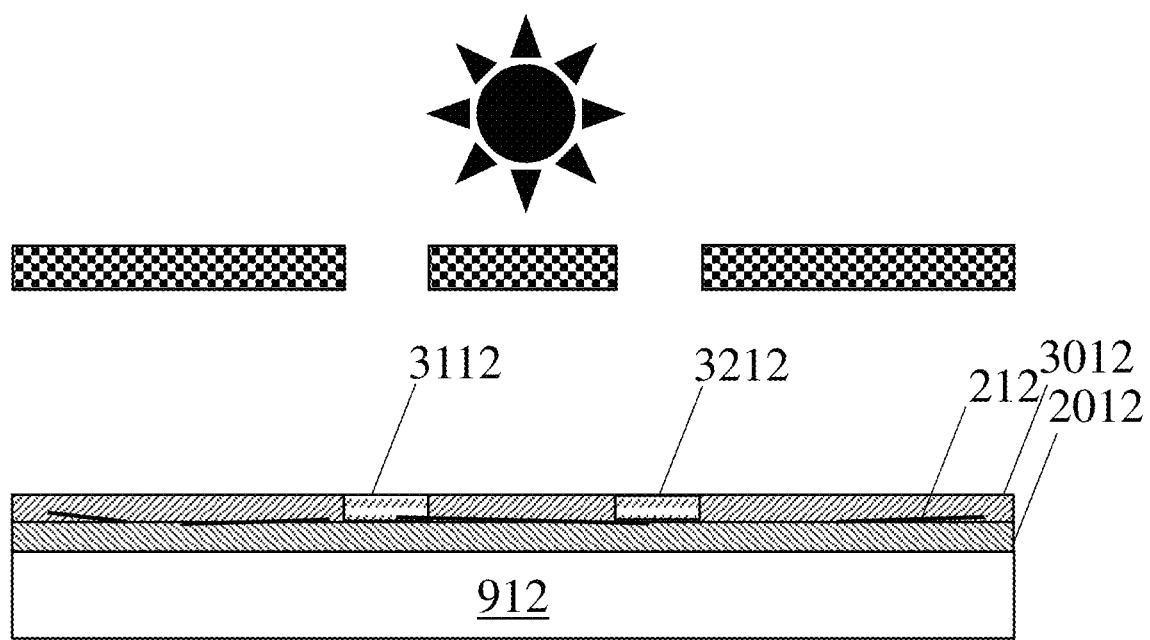
Figure 10D:
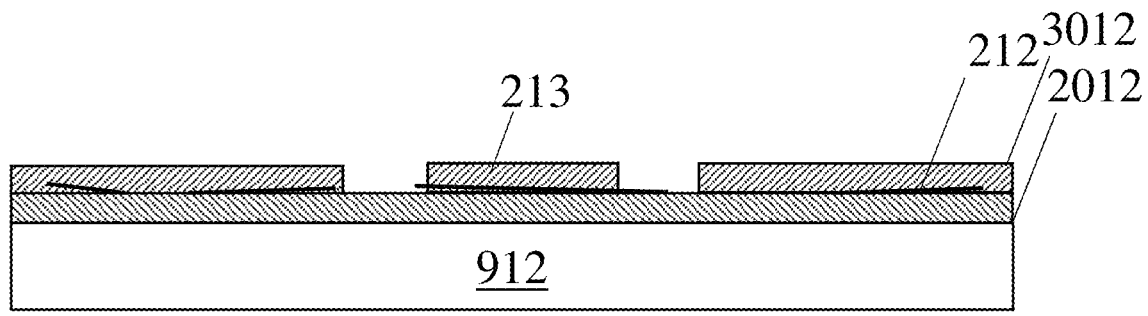
Figure 10E:
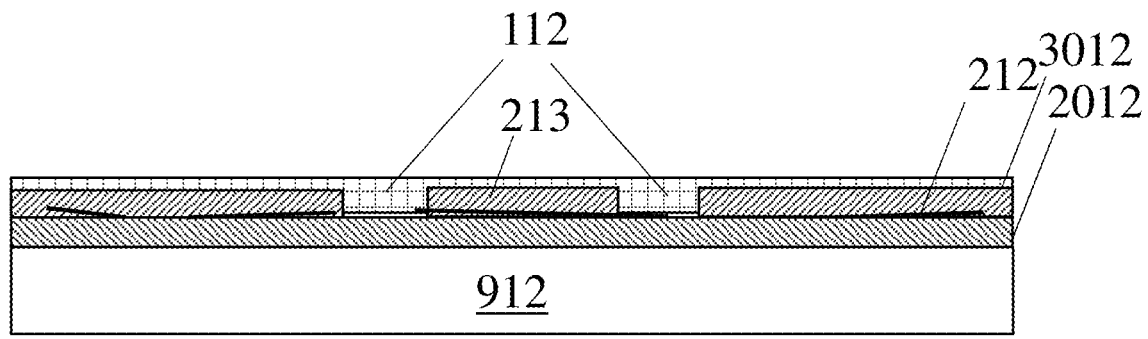

FIGS. 10A-10E show one method of depositing a pair of electrodes on a substrate on which a plurality of nanowires is disposed. FIG. 10A shows a substrate 912 on which a surface layer 2012 is disposed. The plurality 212 of nanowires is disposed thereon. In FIG. 10B, a photoresist 3012 has been deposited on the plurality of nanowires 212. FIG. 10C shows the exposure to light of portions 3112 and 3212 of the photoresist, and FIG. 10D shows the substrate, nanowires, and photoresist after removal of portions 3112 and 3212 of the photoresist upon exposure to a developer. FIG. 10E depicts the deposition of an electrode material on the photoresist, plurality of nanowires, and substrate to form a pair of electrodes 112. It is noted that nanowire 213 in the plurality of nanowires 212 is in direct contact and electrical communication with both electrodes in the pair of electrodes 112. It is also noted that the pair of electrodes 112 is in electrical communication with each other by the nanowire 213.

In some embodiments, a process may be formed after the step shown in FIG. 10D and the step shown in FIG. 10E. By way of example, the substrate and/or nanowires disposed thereon may be prepared for deposition of the electrode material. For instance, any portions of the nanowire unsuitable for forming an ohmic contact with the electrode material may be removed (e.g., any oxide thereon). This may be accomplished by etching the surfaces of the nanowires, such as by exposing the nanowires to an etchant (e.g., by dipping the substrate in an etchant, by performing a plasma etch). The etchant may be the same type of etchant suitable for removing a surface layer from a substrate described above and/or the etching process may be the same etching process described above with respect to forming fiducial alignment marks in a surface layer. The etching time may be selected to be sufficient to remove the desired material from the nanowires (e.g., any oxide on the nanowires) but not sufficient to remove desirable components of the substrate (e.g., all of the oxide on the substrate). For instance, in some embodiments, the etching time may be selected to be sufficient to remove approximately several nanometers of oxide but insufficient to remove hundreds of nanometers of oxide (e.g., sufficient to remove 2-5 nm of oxide but insufficient to remove 300-600 nm of oxide). As another example of a process that may be performed after the steps shown in FIGS. 10D and 10E, the substrate and/or nanowires disposed thereon may be cleaned by exposure to a solvent and then spun dry. The solvent may comprise an organic solvent and/or may comprise water (e.g., deionized water). Non-limiting examples of suitable organic solvents include acetone and alcohols (e.g., methanol, isopropanol).

Figure 11:
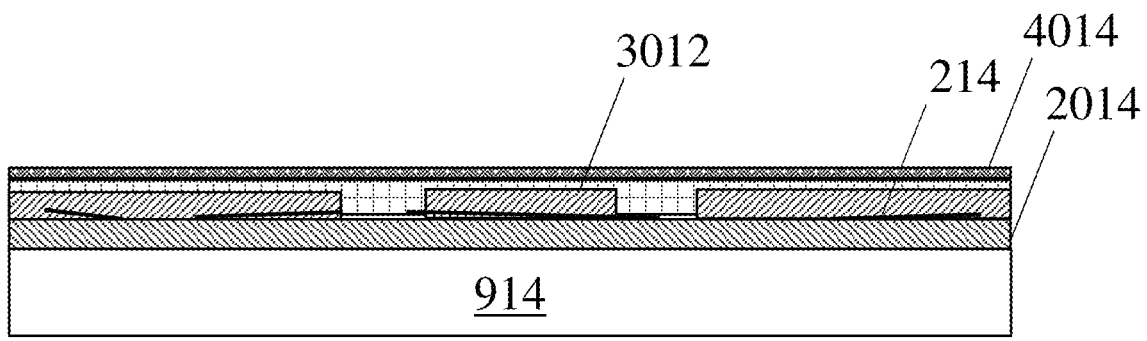
FIG. 11 shows one method of forming a passivating layer disposed on an electrode material, in accordance with some embodiments.

After formation of the pairs of electrodes, the surfaces of the pair(s) of electrodes may be passivated. For instance, a passivating layer may be formed thereon. The surfaces may be passivated by exposure to a gas that reacts with the electrodes to alter their surface chemistry and/or may be passivated by depositing a material thereon (e.g., from a gas, from a liquid). If the pairs of electrodes are formed with the assistance of a photoresist as shown in FIGS. 10A-10E, the entire surface of the electrode material may be passivated (e.g., the surface of the electrode material forming the pair(s) of electrodes and the surface of the electrode material disposed on the photoresist). It is also possible for only the electrode surfaces to be passivated (e.g., in the case where pair(s) of electrodes are fabricated by another method, in the case where electrode material not forming the pair(s) of electrodes is removed prior to the passivation process). FIG. 11 shows one method of forming a passivating layer 4014 disposed on the electrode material. Passivating the surfaces of the pair(s) of electrodes may advantageously reduce the reactivity of the material forming the electrodes and/or protect the material forming the electrodes during further fabrication steps.

Figure 12:
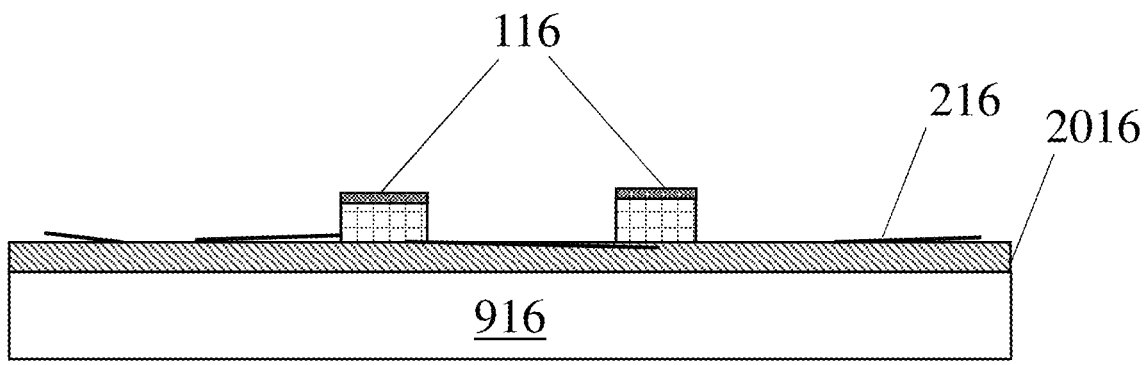
FIG. 12 shows one example of an article comprising a substrate, a surface layer disposed on the substrate, a plurality of nanowires disposed on the surface layer, and a pair of passivated electrodes disposed on the surface layer and the plurality of nanowires, in accordance with some embodiments.

As described above, methods comprising forming electrodes with the assistance of a photoresist may comprise removing the photoresist and any electrode material disposed thereon from the substrate. This step may allow for the deposition of further, non-electrode material onto one or more portions of the substrate covered by the photoresist during electrode formation. The photoresist may be removed directly after deposition of the electrode material (e.g., prior to passivation of the surface of the electrode material or any other further steps), directly after passivation of the surface of the electrode material (e.g., and prior to any other further steps), or at a later point in time (e.g., after the formation of ohmic contacts between the electrodes and the nanowires to which they are directly adjacent). The photoresist may be removed from the substrate by, for example, exposing it to a solvent in which it is soluble. FIG. 12 shows one example of an article comprising a substrate 916, a surface layer 2016 disposed on the substrate, a plurality of nanowires 216 disposed on the surface layer, and a pair of passivated electrodes 116 disposed on the surface layer and the plurality of nanowires.

Another step that may be performed subsequent to the deposition of pair(s) of electrodes is the formation of ohmic contacts between the electrodes and the nanowire(s) to which the electrodes are directly adjacent. This step may be performed after passivating the surfaces of the pair(s) of electrodes, prior to passivating the surfaces of the pair(s) of electrodes, or as a step in a method that does not comprise passivating the surfaces of the pair(s) of electrodes. In some embodiments, it may be advantageous to passivate the surfaces of the pair(s) of electrodes prior to formation of the ohmic contacts because the method employed to form the ohmic contacts may be performed in a manner such that the electrodes are exposed to an environment that would promote one or more deleterious reactions at the electrode surfaces if unpassivated but for which passivated electrode surfaces may be relatively unreactive. By way of example, in some embodiments, the ohmic contacts may be formed by exposing the electrodes and the plurality of nanowires to a heated environment and/or an environment comprising one or more gases reactive with the electrode surfaces. It may also be advantageous to remove any photoresist disposed on the substrate prior to formation of the ohmic contacts for similar reasons. Many photoresists that may be desirable for use in forming electrodes may be undesirably reactive under the conditions present during ohmic contact formation.

A fourth step that may be performed subsequent to the deposition of pair(s) of electrodes is the formation of a layer positioned between the pair(s) of electrodes and an environment external to the electrodes. A layer having this property may electrically insulate the electrodes from the environment external thereto, which may advantageously prevent the formation of short circuits when the electrodes are exposed to an environment that is electrically conductive (e.g., an aqueous environment). This step is typically performed subsequent to the step of passivating the surfaces of the electrodes. It may be performed subsequent to the step of removing any photoresist deposited on the substrate and/or the step of forming an ohmic contact between the electrodes and the nanowires to which they are directly adjacent. The layer positioned between the pair(s) of electrodes and an environment external to the electrodes may be formed by a variety of suitable processes, including vapor deposition and/or spin coating.

Figure 13:
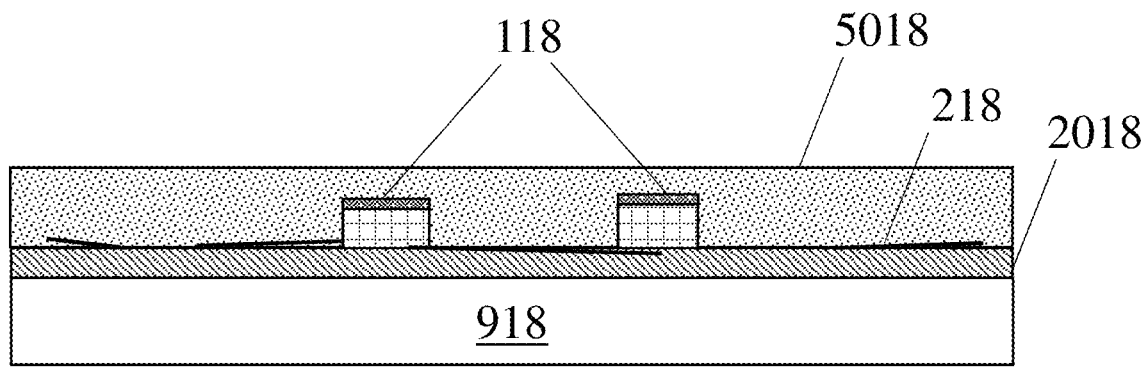
FIG. 13 shows one non-limiting embodiment of an article comprising a layer positioned between a pair of electrodes and an environment external to the electrodes, in accordance with some embodiments.

FIG. 13 shows one non-limiting embodiment of an article comprising a layer positioned between a pair of electrodes and an environment external to the electrodes. In FIG. 13, the layer 5018 is disposed on the pair of electrodes 118, the plurality of nanowires 218, and the surface layer 2018 that are all disposed on the substrate 918. This layer isolates these components of the article from an environment external thereto. Example 1 provides a description of one exemplary method by which an electrically insulating layer positioned at this location may be formed.

Figure 14:
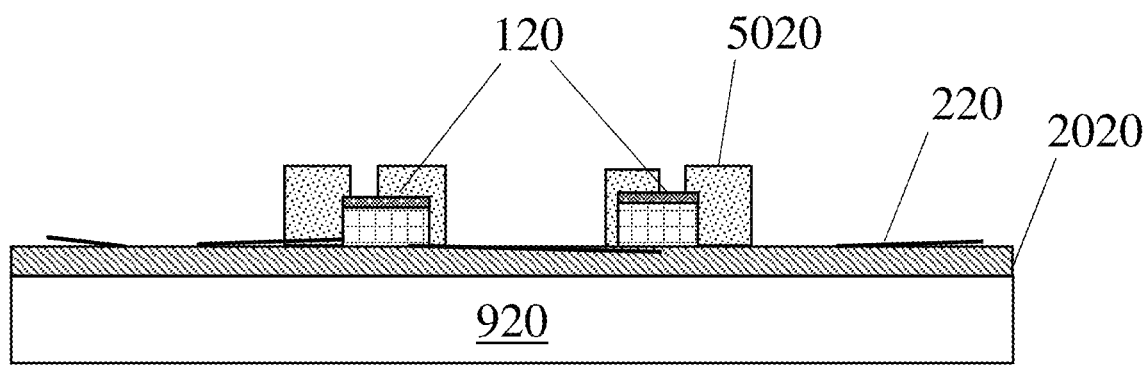
FIG. 14 shows one example of an article in which a layer disposed on the pair of electrodes exposes a portion of a plurality of nanowires, a portion of a surface layer, and a portion of each member of the pair of electrodes to an environment external thereto, in accordance with some embodiments.

Some layers positioned between a pair of electrodes and an environment external thereto may be disposed over the entirety of an external surface of the article comprising the pair of electrodes (e.g., as shown in FIG. 13). In other embodiments, an article may comprise a layer positioned between a pair of electrodes and an environment external to the electrodes that exposes one or more portions of the article to the environment external to the electrodes. By way of an example, in some embodiments, a layer positioned between a pair of electrodes and an environment external to the electrodes does not cover a portion of the nanowires in the plurality of nanowires (e.g., one or more nanowires in electrical communication with one or both of the electrodes in the pair of electrodes), one or more portions of the surface layer disposed on the substrate, one or more portions of the substrate (e.g., one or more portions of the substrate from which a surface layer disposed thereon has been etched away to form a fiducial alignment mark), and/or one or more portions of the electrodes configured to be isolated from an environment external thereto by a different component. FIG. 14 shows one example of an article in which the layer 5020 disposed on the pair of electrodes 120 exposes a portion of the plurality of nanowires 220, a portion of a surface layer 2020, and a portion of each member of the pair of electrodes 120 to an environment external thereto. A layer positioned between a pair of electrodes and an environment external to the electrodes that exposes one or more other components of the article in which it is positioned may be fabricated to do so by use of a photoresist that can be patterned through a mask as described elsewhere herein.

In some embodiments, a method of fabricating a sensor comprises forming a component that places one or more pairs of electrodes therein in in electrical communication with an environment external to the sensor. This step is typically performed after formation of the pair(s) of electrodes and after formation of a layer positioned between the pair(s) of electrodes and an environment external to the electrodes. In such cases, one or more portions of the layer positioned between the pair(s) of electrodes and an environment external to the electrodes may be removed therefrom (e.g., as described in the preceding paragraph), and a composition configured to place the electrodes and an environment external thereto may be deposited on the electrode at the location(s) from which this layer was removed. It is also possible for a component that places one or more pairs of electrodes therein in electrical communication with an environment external to the sensor to be formed prior to the formation of a layer positioned between the pair(s) of electrodes and an environment external to the electrodes and/or to be formed in embodiments which lack a layer positioned between the pair(s) of electrodes and an environment external to the electrodes.

Similarly, some sensors comprise a pair of electrodes in electrical communication with an environment external to the sensor. Such electrical communication may be desirable for allowing the sensor to output electrical data indicative of the environment to which it is exposed. For example, some sensors may be configured to output the equivalent surface potential across one or more pairs of electrodes therein. Electrodes may be placed in electrical communication with an environment external thereto by, for example, being placed in electrical communication with a component in communication with the environment external thereto. This may be accomplished by placing the electrodes in direct contact with the relevant component. In some embodiments, a wire bonding composition is disposed on a portion of an external surface of the electrodes described herein for this purpose. The wire bonding composition may be configured to also be capable of being placed in electrical communication with a component capable of outputting data from the electrodes in a manner that can easily be interpreted by a user of the sensor and/or computer program (e.g., with a voltmeter).

Figure 15:
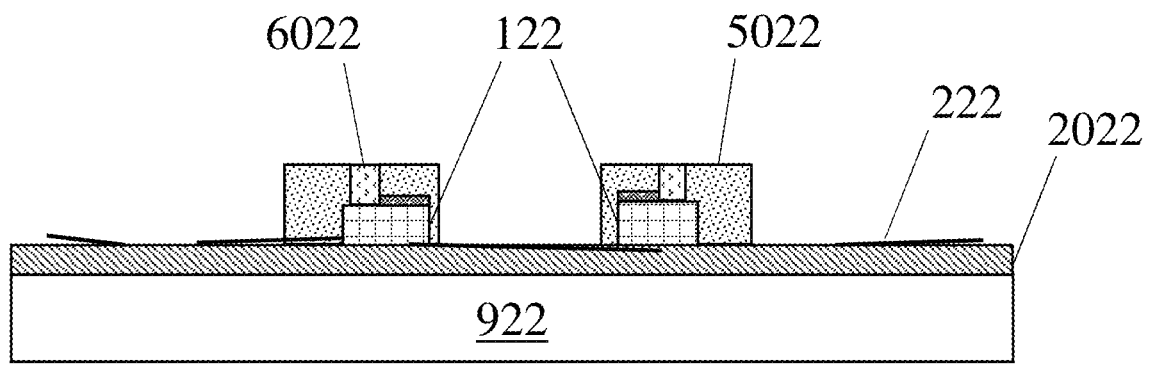
FIG. 15 shows one example of a sensor comprising a wire bonding composition disposed on a portion of each member of the pair of electrodes, in accordance with some embodiments.

FIG. 15 shows one example of a sensor comprising a wire bonding composition 6022 disposed on a portion of each member of the pair of electrodes 122. Example 2 provides more detail about one process that may be employed to dispose a wire bonding composition on a pair of electrodes. As shown in FIG. 15, the wirebonding composition may be disposed directly on the electrode material in the electrode. It is also possible for the wirebonding composition to be disposed on the electrodes in a manner such that one or more intervening components are present between it and the electrode material. For instance, the wirebonding composition may be disposed on an electrically conductive material disposed on the electrode material, such as an electrically conductive material that facilitates bonding between the electrode material and the wirebonding composition. One example of an electrically conductive material suitable for this purpose is an alloy of titanium and gold. When the wirebonding composition is disposed directly on a portion of the electrode material in an electrode for which a passivating layer is disposed directly on a different portion thereof, the electrode material in the electrodes may be exposed for contact with the wirebonding composition by removing a portion of the passivating layer disposed thereon. This may be accomplished by, for instance, employing a photolithography technique described elsewhere herein.

Another example of a step that may be performed during the fabrication of the sensors described herein is the formation of one or more components thereof that promotes interaction between the sensor and one or more analytes of interest in a desirable manner. By way of example, the surface chemistry of one or more components of the sensor may be altered to promote a desirable interaction with one or more analytes of interest (in other words, one or more components of the sensor may be functionalized). For instance, one or more types of molecules may be bound to the surfaces of a plurality of nanowires. Such molecules may include those which are configured to bind with an analyte of interest (e.g., they may comprise antibodies for an antigen of interest). Molecules of interest may be bound to the nanowires by covalent attachment. In some embodiments, covalent attachment of molecules of interest to the nanowires may be facilitated by the use of silane derivatives. A silane derivative comprising a functional group suitable for bonding with the molecule of interest (e.g., an amino group, such as a primary amino group, an aldehyde group, an epoxy group) may be covalently attached to the nanowires. Then, the molecule(s) of interest may, after optionally being activated to facilitate bonding with the silane derivative, allowed to react with the silane derivative to form a covalent bond therewith. In some embodiments, it may be advantageous to alter the surface chemistry of the plurality of nanowires as one of the later steps during sensor fabrication and/or after steps during which the molecule(s) of interest may be degraded (e.g., after any photolithography steps, after any etching steps).

As another example, and as also described elsewhere herein, in some embodiments, a blocking layer is formed on one or more components of the sensor. The blocking layer may be positioned between these component(s) and an environment external to the sensor. In some embodiments, a blocking layer mediates interactions between one or more components of an environment external to the sensor (e.g., one or more samples to be analyzed and/or one or more components thereof, such as one or more analytes therein). For instance, a blocking layer may reduce non-specific interactions of sample(s) and/or component(s) therein with one or more components of the sensor (e.g., with a plurality of nanowires therein). Blocking layers suitable for this purpose may be formed from and/or comprise materials that do not bind readily with sample components (e.g., proteins) other than the analyte(s) of interest. As another example, a blocking layer may reduce electrostatic charge screening by a sample to be analyzed with one or more components of the sensor (e.g., with a plurality of nanowires therein).

A blocking layer may be introduced to a sensor by a variety of suitable processes. One example of a suitable process comprises dispensing a solution comprising the components of the blocking layer on the sensor and/or one or more components thereof and then incubating the sensor on which the solution is disposed to allow for bonding between the components of the blocking layer and the sensor and/or component(s) thereof.

Figure 16:
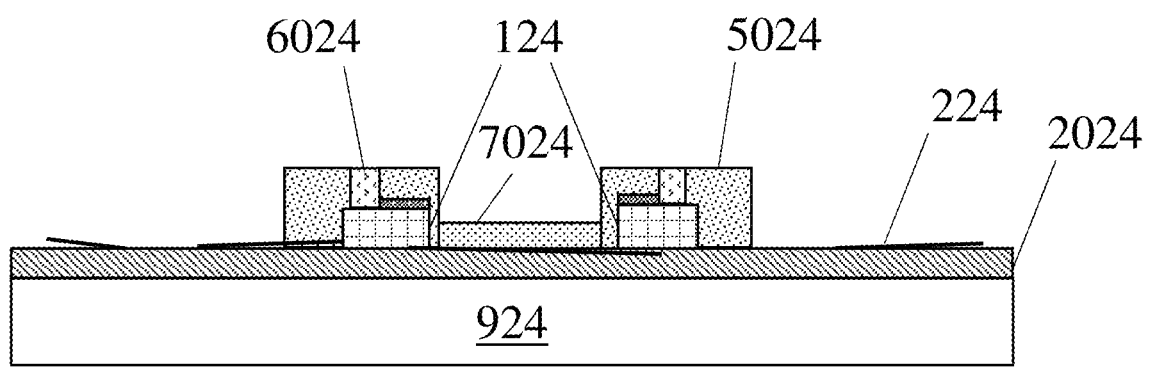
FIG. 16 shows one example of a sensor comprising a blocking layer that is disposed over a nanowire placing a pair of electrodes in electrical communication, but absent from other portions of the sensor, in accordance with some embodiments.

When present, a blocking layer may be disposed on one or more discrete portions of the sensor or may form a coating that covers a significant fraction of the sensor (e.g., it may cover all, or a majority, of the portions of the sensor not in electrical communication with an environment external thereto). FIG. 16 shows one example of a sensor a sensor comprising a blocking layer 7024 that is disposed over a nanowire placing a pair of electrodes 124 in electrical communication, but absent from other portions of the sensor.

Some methods may comprise the formation of electrodes other than the pairs of electrodes described elsewhere herein and some sensors may comprise such electrodes. By way of example, a sensor may further comprise a back gate electrode, a water gate electrode, and/or a ground electrode. These electrode(s), when present, may be formed by photolithography processes (e.g., as described elsewhere herein). They may be performed in a single step or may be fabricated by separate steps. The steps employed to form these electrode(s) may be performed at any suitable time. In some embodiments, one or more of these electrodes may be formed concurrently with the formation of the pair(s) of electrodes. For instance, a photolithographic process employed to form a pair of electrodes as described elsewhere herein may also comprise the formation of one or more further electrodes by also comprising removal of the photoresist from the location at which these electrode(s) are to be formed concurrently with removal of the photoresist from the location at which the pair of electrodes is to be formed and by also comprising deposition of the material forming these electrode(s) on the portion(s) of the substrate exposed by this process concurrently with deposition of the material forming the pair of electrodes.

Figure 17A:
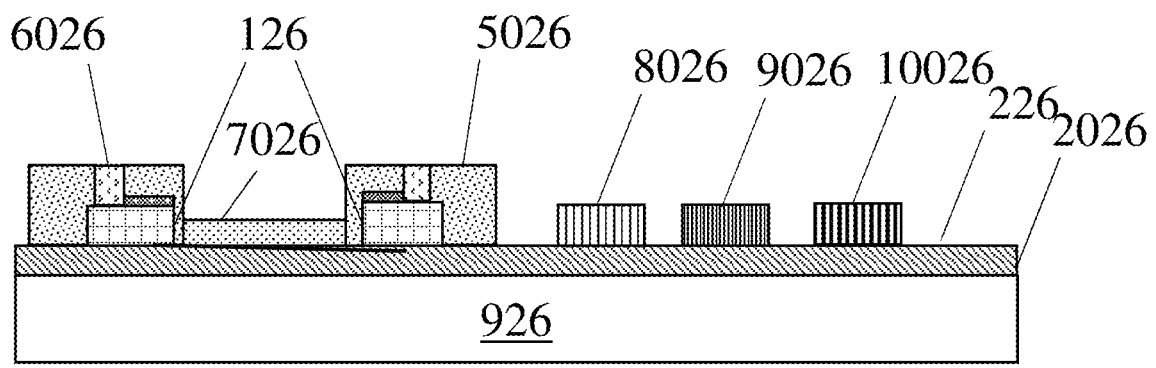
FIG. 17A shows one non-limiting embodiment of a sensor comprising a pair of electrodes and further comprising a back gate electrode, a water gate electrode, and a ground electrode, in accordance with some embodiments.

FIG. 17A shows one non-limiting embodiment of a sensor comprising a pair of electrodes 126 and further comprising a back gate electrode 8026, a water gate electrode 9026, and a ground electrode 10026. Such electrodes, when present, may be directly exposed to an environment external to the sensor and/or may lack passivating layers and/or electrically insulating layers disposed thereon. In other embodiments, one or more passivating layers and/or electrically insulating layers may be positioned between one or more of these electrodes and an environment external thereto.

In some embodiments, a back gate electrode, a water gate electrode, and/or a ground electrode may be disposed on the substrate such that it is in direct contact with the material forming the bulk thereof (e.g., instead of the surface layer). By way of example, in some embodiments, an electrode (e.g., a back gate electrode) is deposited onto a portion of the substrate from which the surface layer has been etched. Without wishing to be bound by any particular theory, it is believed that it may be advantageous for back gate electrodes to be disposed on the substrate such that they are in direct contact with the material forming the bulk thereof. It is believed that this arrangement may enhance the consistency of the gating provided by the back gate electrode, may allow for dry gating of the plurality of nanowires, and/or may provide a facile way to ground the bulk substrate.

Figure 17B:
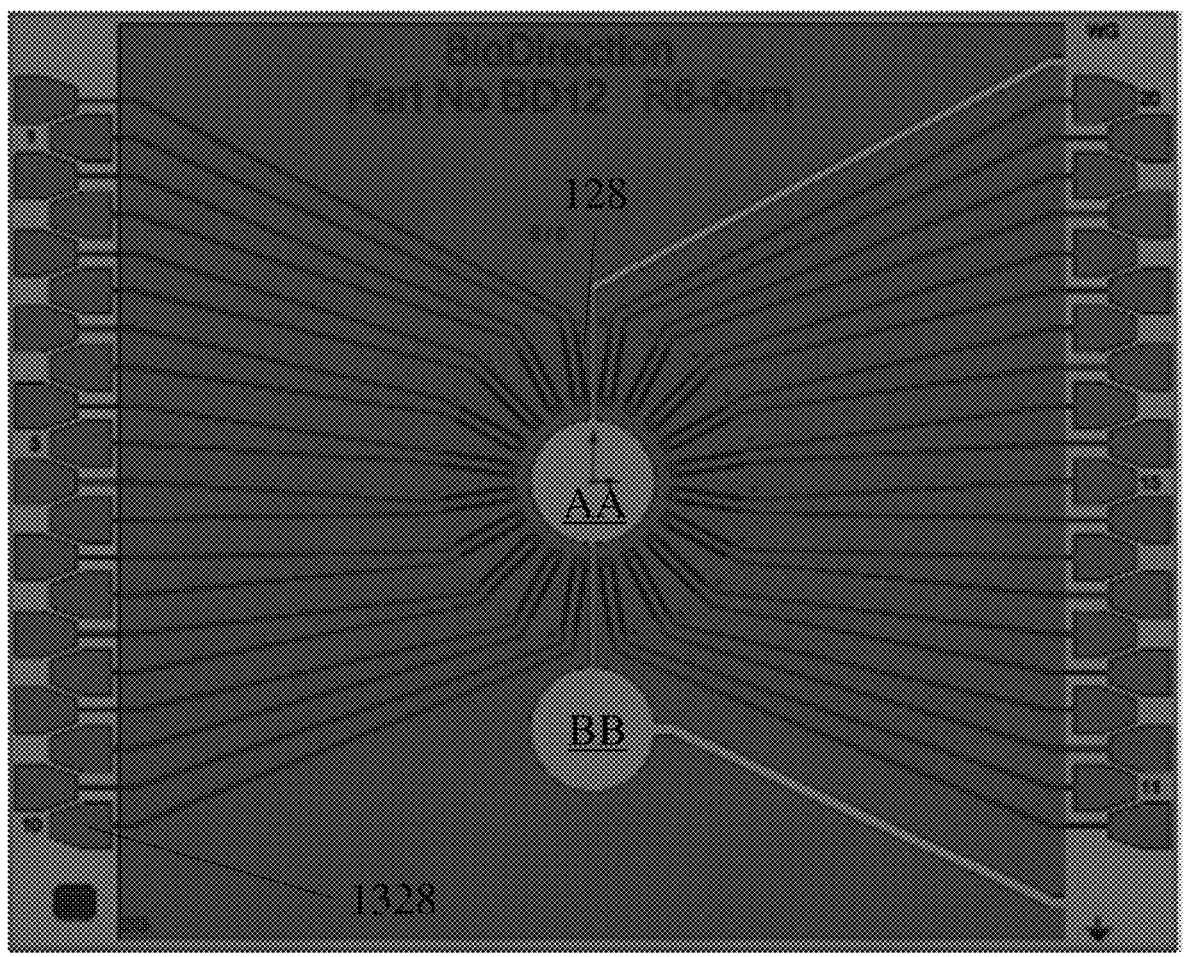
FIG. 17B shows a top view of one exemplary embodiment of a sensor comprising two further electrodes in addition to a plurality of pairs of electrodes, in accordance with some embodiments.
Figure 17C:
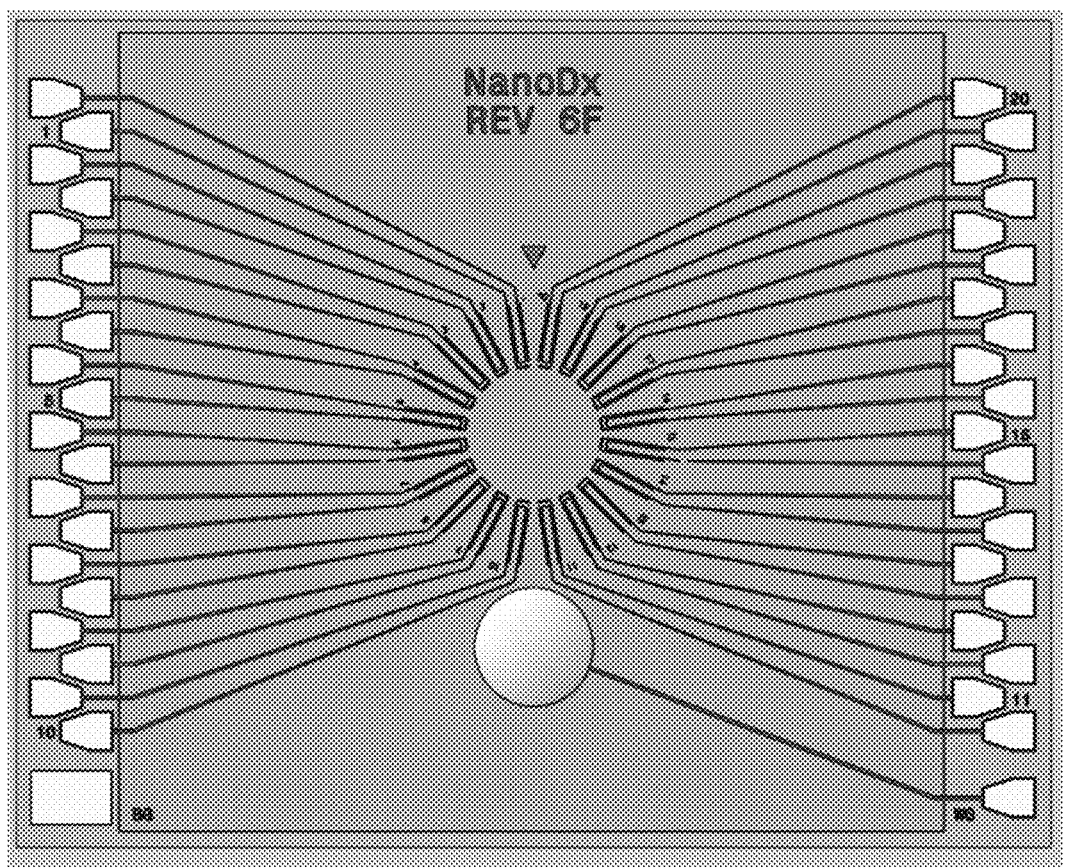
FIG. 17C shows a top view of one exemplary embodiment of a sensor comprising one further electrode in addition to a plurality of pairs of electrodes, in accordance with some embodiments.

FIG. 17B shows a top view of one exemplary embodiment of a sensor comprising two further electrodes in addition to a plurality of pairs of electrodes. In FIG. 17B, a plurality of pairs of electrodes 128 is electrodes arranged to have radial symmetry around a center point. A first electrode AA is disposed on and symmetrically around the center point. A second electrode BB is in electrical communication with the first electrode AA. Each electrode is in electrical communication with an environment external to the sensor by a wire connecting the electrode with a contact pad 1328. The contact pad may be placed in electrical communication with a voltmeter, computer, or other device. A sensor having a design like that shown in FIG. 17B may be configured such that both the first and second electrodes are ground electrodes. It is also possible for a sensor to have a design like that shown in FIG. 17B and be configured such that both the first and second electrodes are reference electrodes, or for such a sensor to be configured to employ one but not the other of the first and second electrodes shown in FIG. 17B. FIG. 17C shows one example of a sensor including the second electrode shown in FIG. 17B but not the first electrode. In other respects, this sensor is the same as the sensor shown in FIG. 17B.

In some embodiments, a sensor further comprises an external layer configured to be removed prior to and/or during use thereof. The external layer may protect the sensor prior to use (e.g., during transport) and then removed so that the sensor can function when desired. In some embodiments, the external layer is a layer that is soluble in a fluid to which the sensor is configured to be exposed (e.g., for the purpose of removing the layer, during sensing). By way of example, in some embodiments, the external layer may be a layer that is soluble in buffered saline and/or one or more bodily fluids. Such layers may be removed by dissolution in the relevant fluid. Non-limiting examples of suitable compositions for external layers include sugars and/or proteins.

Figure 18:
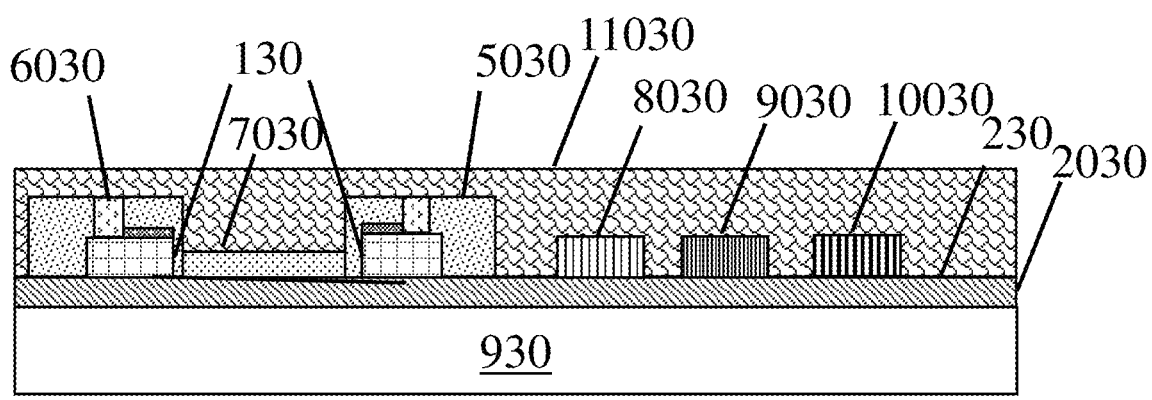
FIG. 18 shows one non-limiting example of a sensor comprising an external layer, in accordance with some embodiments.

FIG. 18 shows one non-limiting example of a sensor comprising an external layer 11030. As shown in FIG. 18, an external layer may be disposed on the entirety of the external surface of a sensor. It is also possible for a sensor to comprise an external layer that is disposed only on one or more portions thereof (e.g., one or more particularly delicate portions, such as nanowires therein and/or molecule(s) configured to bond with one or more analytes of interest exposed thereto) and/or to form a conformal coating.

The sensors described herein may be incorporated into fluidic devices. By way of example, in some embodiments, a fluidic device comprises one or more sensors described herein. The fluidic device may be configured to receive a fluid, pass the fluid over the sensor, and then output information about the fluid (e.g., the presence and/or concentration of one or more analytes) based on a property of the sensor upon exposure to the fluid. In some embodiments, a fluidic device may comprise a plurality of sensors. The fluidic device may be configured to pass a fluid over two or more sensors sequentially (e.g., each sensor may be configured to sense a different property of the fluid, such as the presence and/or concentration of different analytes therein) and/or may comprise two or more sensors that are not in fluidic communication with each other (e.g., a fluidic device may comprise multiple, distinct fluid pathways through which fluid can be passed that are each configured to act on a fluid introduced thereto in an identical manner). Some fluidic devices comprising the sensors described herein may be microfluidic devices.

Having provided an overview of the various components that may be included the sensors described herein and the methods that may be employed to form the sensors described herein, further details regarding particular sensor components and method steps are provided below.

As described elsewhere herein, some sensors comprise a plurality of nanowires. When present, the nanowires may have one or more physical or chemical characteristics that enhance sensor performance. Such physical and chemical characteristics are described below.

A plurality of nanowires may comprise a variety of suitable numbers of nanowires. In some embodiments, a plurality of nanowires comprises at least 30 nanowires, at least 50 nanowires, at least 75 nanowires, at least 100 nanowires, at least 200 nanowires, at least 500 nanowires, at least 750 nanowires, at least 1,000 nanowires, at least 1,250 nanowires, at least 1,500 nanowires, at least 1,750 nanowires, at least 2,000 nanowires, at least 2,500 nanowires, at least 3,000 nanowires, at least 4,000 nanowires, at least 5,000 nanowires, at least 7,500 nanowires, at least 10,000 nanowires, at least 20,000 nanowires, at least 50,000 nanowires, or at least 75,000 nanowires. In some embodiments, a plurality of nanowires comprises at most 100,000 nanowires, at most 75,000 nanowires, at most 50,000 nanowires, at most 20,000 nanowires, at most 10,000 nanowires, at most 7,500 nanowires, at most 5,000 nanowires, at most 4,000 nanowires, at most 3,000 nanowires, at most 2,500 nanowires, at most 2,000 nanowires, at most 1,750 nanowires, at most 1,500 nanowires, at most 1,250 nanowires, at most 1,000 nanowires, at most 750 nanowires, at most 500 nanowires, at most 200 nanowires, at most 100 nanowires, at most 75 nanowires, or at most 50 nanowires. Combinations of the above-referenced ranges are also possible (e.g., at least 30 nanowires and at most 100,000 nanowires, or at least 30 nanowires and at most 1,000 nanowires). Other ranges are also possible.

In some embodiments, a plurality of nanowires comprises nanowires oriented substantially tangentially to a circular structure. Such nanowires may have an angle with respect to the circular structure that is greater than or equal to 70°, greater than or equal to 72.5°, greater than or equal to 75°, greater than or equal to 77.5°, greater than or equal to 80°, greater than or equal to 82.5°, greater than or equal to 85°, greater than or equal to 87.5°, or greater than or equal to 89°. In some embodiments, a nanowire that is oriented substantially tangentially to a circular structure has an angle with respect to the circular structure of less than or equal to 90°, less than or equal to 89°, less than or equal to 87.5°, less than or equal to 85°, less than or equal to 82.5°, less than or equal to 80°, less than or equal to 77.5°, less than or equal to 75°, or less than or equal to 72.5°. Combinations of the above-referenced ranges are also possible (e.g., greater than or equal to 70° and less than or equal to 90°, or greater than or equal to 80° and less than or equal to 90°). Other ranges are also possible.

Some pluralities of nanowires may comprise a relatively high number of nanowires that are oriented substantially tangentially to a circular structure. For instance, in some embodiments, greater than or equal to 30%, greater than or equal to 40%, greater than or equal to 50%, greater than or equal to 60%, greater than or equal to 70%, greater than or equal to 75%, greater than or equal to 80%, greater than or equal to 85%, greater than or equal to 90%, greater than or equal to 95%, greater than or equal to 97.5%, or greater than or equal to 99% of the nanowires in a plurality of nanowires have an angle with respect to a circular structure in one or more of the above-referenced ranges. In some embodiments, less than or equal to 100%, less than or equal to 99%, less than or equal to 97.5%, less than or equal to 95%, less than or equal to 90%, less than or equal to 85%, less than or equal to 80%, less than or equal to 75%, less than or equal to 70%, less than or equal to 60%, less than or equal to 50%, or less than or equal to 40% of the nanowires in a plurality of nanowires have an angle with respect to a circular structure in one or more of the above-referenced ranges. Combinations of the above-referenced ranges are also possible (e.g., greater than or equal to 30% and less than or equal to 100%, greater than or equal to 75% and less than or equal to 100%). Other ranges are also possible.

In some embodiments, a plurality of nanowires comprises nanowires having a chemical composition that is desirable. By way of example, the nanowires may be formed from and/or comprise a material that is capable of being functionalized with one or more chemistries of interest (e.g., one or more chemistries having a desirable interaction with an analyte of interest and/or which can further react with a molecule having a desirable interaction with an analyte of interest). As another example, the nanowires may be formed from and/or comprise a material having a desirable electrical conductivity and/or equivalent surface potential (e.g., from a semiconductor, from a material that exhibits a change in electrical conductivity upon exposure to an analyte of interest, and/or from a material that exhibits a change in equivalent surface potential upon exposure to an analyte of interest). Non-limiting examples of materials having this property include selected elements (e.g., silicon), ceramics (e.g., gallium nitride, gallium arsenide, indium oxide, indium phosphide, molybdenum disulfide, tungsten disulfide), polymers (e.g., semiconducting polymers), one-dimensional materials (e.g., carbon nanotubes, one-dimensional materials comprising one or more of the above-referenced materials), and two-dimensional materials (e.g., graphene, two-dimensional materials comprising one or more of the above-referenced materials). In some embodiments, the nanowires are formed from and/or comprise one or more of the above-referenced materials in single-crystalline form (e.g., single-crystalline silicon).

Non-limiting examples of functional groups the surfaces of the nanowires may be functionalized to include comprise hydroxyl groups, epoxy groups, aldehyde groups, amino groups (e.g., (3-aminopropyl)triethoxysilane), and halogen groups. Some functional groups may cause the nanowires to have a charged surface (e.g., positively charged, negatively charged, zwitterionic). In some embodiments, a surface of a nanowire is functionalized with a binding entity (e.g., a binding entity for an analyte to be detected by the sensor). By way of example, a nanowire may comprise a binding entity for glial fibrillary acidic protein (GFAP), UCH-L1, S1000, ICH, NFL-1, D-dimer, a viral protein (e.g., a human viral protein, a non-human animal viral protein, a plant viral protein), a small molecule and/or a lipid. Further non-limiting examples of viral proteins include a SARS-CoV-2 proteins (e.g., spike (S) proteins, nucleocapsid (N) proteins, envelope (E) proteins), influenza virus proteins (e.g., hemagglutinin (HA) proteins, neuraminidase (NA) proteins, matrix proteins (M1, M2)), zika virus proteins, parainfluenza virus proteins, HIV1 proteins, CMV proteins, and HHV proteins.

Some nanowires suitable for use in the sensors described herein have an electrical conductivity in a desirable range. By way of example, in some embodiments, a plurality of nanowires comprises nanowires having an electrical conductivity of greater than or equal to 0.333 S/cm, greater than or equal to 0.667 S/cm, greater than or equal to 1 S/cm, greater than or equal to 2.22 S/cm, greater than or equal to 6.67 S/cm, greater than or equal to 10 S/cm, greater than or equal to 12 S/cm, greater than or equal to 14.3 S/cm, greater than or equal to 20 S/cm, greater than or equal to 50 S/cm, greater than or equal to 75 S/cm, greater than or equal to 100 S/cm, greater than or equal to 200 S/cm, greater than or equal to 286 S/cm, greater than or equal to 350 S/cm, greater than or equal to 500 S/cm, greater than or equal to 750 S/cm, greater than or equal to 1,000 S/cm, greater than or equal to 2,000 S/cm, greater than or equal to 5,000 S/cm, greater than or equal to 7,500 S/cm, greater than or equal to 10,000 S/cm, greater than or equal to 20,000 S/cm, greater than or equal to 30,000 S/cm, or greater than or equal to 40,000 S/cm. In some embodiments, a plurality of nanowires comprises nanowires having an electrical conductivity of less than or equal to 50,000 S/cm, less than or equal to 40,000 S/cm, less than or equal to 30,000 S/cm, less than or equal to 20,000 S/cm, less than or equal to 10,000 S/cm, less than or equal to 7,500 S/cm, less than or equal to 5,000 S/cm, less than or equal to 2,000 S/cm, less than or equal to 1,000 S/cm, less than or equal to 750 S/cm, less than or equal to 500 S/cm, less than or equal to 350 S/cm, less than or equal to 286 S/cm, less than or equal to 200 S/cm, less than or equal to 100 S/cm, less than or equal to 75 S/cm, less than or equal to 50 S/cm, less than or equal to 20 S/cm, less than or equal to 14.3 S/cm, less than or equal to 12 S/cm, less than or equal to 10 S/cm, less than or equal to 6.67 S/cm, less than or equal to 2.22 S/cm, less than or equal to 1 S/cm, or less than or equal to 0.67 S/cm. Combinations of the above-referenced ranges are also possible (e.g., greater than or equal to 0.333 S/cm and less than or equal to 50,000 S/cm, greater than or equal to 2.22 S/cm and less than or equal to 286 S/cm, or greater than or equal to 14.3 S/cm and less than or equal to 286 S/cm). Other ranges are also possible. The electrical conductivity of a plurality of nanowires may be determined by use of a semiconductor parameter analyzer.

In some embodiments, the average conductivity of the nanowires in a plurality of nanowires is in one or more of the above-referenced ranges. The ranges described above may independently characterize initial conductivity of the nanowires (e.g., the conductivity of the nanowires at their time of manufacture, the conductivity of the nanowires after deposition on a substrate but prior to functionalization, the conductivity of the nanowires after sensor fabrication but before use thereof) and/or the conductivity of the nanowires at another point in time (e.g., after use of the sensor for a period of minutes, hours, days, or longer).

Some nanowires suitable for use in the sensors described herein have an on/off ratio that is advantageous. For instance, a plurality of nanowires may comprise nanowires having an on/off ratio of greater than or equal to 2, greater than or equal to 5, greater than or equal to 7.5, greater than or equal to 10, greater than or equal to 20, greater than or equal to 50, greater than or equal to 75, greater than or equal to 100, greater than or equal to 200, greater than or equal to 500, greater than or equal to 750, greater than or equal to 1,000, greater than or equal to 2,000, greater than or equal to 5,000, greater than or equal to 7,500, greater than or equal to 10,000, greater than or equal to 20,000, greater than or equal to 50,000, greater than or equal to 75,000, greater than or equal to 100,000, greater than or equal to 200,000, greater than or equal to 500,000, or greater than or equal to 750,000. In some embodiments, a plurality of nanowires comprises nanowires having an on/off ratio of less than or equal to 1,000,000, less than or equal to 750,000, less than or equal to 500,000, less than or equal to 200,000, less than or equal to 100,000, less than or equal to 75,000, less than or equal to 50,000, less than or equal to 20,000, less than or equal to 10,000, less than or equal to 7,500, less than or equal to 5,000, less than or equal to 2,000, less than or equal to 1,000, less than or equal to 750, less than or equal to 500, less than or equal to 200, less than or equal to 100, less than or equal to 75, less than or equal to 50, less than or equal to 20, less than or equal to 10, less than or equal to 7.5, or less than or equal to 5. Combinations of the above-referenced ranges are also possible (e.g., greater than or equal to 2 and less than or equal to 1,000,000, greater than or equal to 1,000 and less than or equal to 1,000,000, or greater than or equal to 10,000 and less than or equal to 1,000,000). Other ranges are also possible.

The on/off ratio for a nanowire may be determined by generating an IV curve by performing a gate sweep and then determining the ratio of the current when the device is in the "on" state to the current when the device is in the "off" state from the IV curve. Briefly, the following procedure may be followed: (1) a constant direct current voltage may be applied across the pair of electrodes; (2) concurrently, the voltage applied to a gate electrode may be varied from −0.5 V to 0.5 V; (3) the current in the "off" state may be determined to be the minimum current measured during variation of the voltage applied to the gate electrode; (4) the current in the "on" state may be determined to be the maximum current measured during variation of the voltage applied to the gate electrode; and (5) the on/off ratio may be determined by dividing the current in the "on" state by the current in the "off" state.

In some embodiments, the average on/off ratio of the nanowires in a plurality of nanowires is in one or more of the above-referenced ranges. The ranges described above may independently characterize initial on/off ratio of the nanowires (e.g., the on/off ratio of the nanowires at their time of manufacture, on/off ratio of the nanowires after deposition on a substrate but prior to functionalization, on/off ratio of the nanowires after sensor fabrication but before use thereof) and/or the on/off ratio of the nanowires at another point in time (e.g., after use of the sensor for a period of minutes, hours, days, or longer).

The nanowires described herein may have a variety of suitable lengths. In some embodiments, a plurality of nanowires comprises nanowires having a length of greater than or equal to 4 microns, greater than or equal to 5 microns, greater than or equal to 6 microns, greater than or equal to 8 microns, greater than or equal to 10 microns, greater than or equal to 11 microns, greater than or equal to 12 microns, greater than or equal to 13 microns, greater than or equal to 14 microns, greater than or equal to 15 microns, greater than or equal to 16 microns, greater than or equal to 17 microns, greater than or equal to 18 microns, greater than or equal to 19 microns, greater than or equal to 20 microns, greater than or equal to 22 microns, greater than or equal to 25 microns, greater than or equal to 27.5 microns, greater than or equal to 30 microns, greater than or equal to 35 microns, greater than or equal to 40 microns, or greater than or equal to 45 microns. In some embodiments, a plurality of nanowires comprises nanowires having a length of less than or equal to 50 microns, less than or equal to 45 microns, less than or equal to 40 microns, less than or equal to 35 microns, less than or equal to 30 microns, less than or equal to 27.5 microns, less than or equal to 25 microns, less than or equal to 22 microns, less than or equal to 20 microns, less than or equal to 19 microns, less than or equal to 18 microns, less than or equal to 17 microns, less than or equal to 16 microns, less than or equal to 15 microns, less than or equal to 14 microns, less than or equal to 13 microns, less than or equal to 12 microns, less than or equal to 11 microns, less than or equal to 10 microns, less than or equal to 8 microns, or less than or equal to 6 microns. Combinations of the above-referenced ranges are also possible (e.g., greater than or equal to 4 microns and less than or equal to 40 microns, greater than or equal to 5 microns and less than or equal to 50 microns, greater than or equal to 10 microns and less than or equal to 25 microns, greater than or equal to 12 microns and less than or equal to 20 microns, or greater than or equal to 14 microns and less than or equal to 16 microns). Other ranges are also possible. In some embodiments, the average length of the nanowires in a plurality of nanowires is in one or more of the above-referenced ranges.

The nanowires described herein may have a variety of suitable diameters. In some embodiments, a plurality of nanowires comprises nanowires having a diameter of greater than or equal to 12 nm, greater than or equal to 13 nm, greater than or equal to 14 nm, greater than or equal to 15 nm, greater than or equal to 16 nm, greater than or equal to 17 nm, greater than or equal to 18 nm, greater than or equal to 19 nm, greater than or equal to 20 nm, greater than or equal to 21 nm, greater than or equal to 22 nm, greater than or equal to 23 nm, greater than or equal to 24 nm, greater than or equal to 25 nm, greater than or equal to 27 nm, greater than or equal to 30 nm, greater than or equal to 32.5 nm, or greater than or equal to 35 nm. In some embodiments, a plurality of nanowires comprises nanowires having a diameter of less than or equal to 40 nm, less than or equal to 35 nm, less than or equal to 32.5 nm, less than or equal to 30 nm, less than or equal to 27 nm, less than or equal to 25 nm, less than or equal to 24 nm, less than or equal to 23 nm, less than or equal to 22 nm, less than or equal to 21 nm, less than or equal to 20 nm, less than or equal to 19 nm, less than or equal to 18 nm, less than or equal to 17 nm, less than or equal to 16 nm, less than or equal to 15 nm, less than or equal to 14 nm, or less than or equal to 13 nm. Combinations of the above-referenced ranges are also possible (e.g., greater than or equal to 12 nm and less than or equal to 40 nm, greater than or equal to 15 nm and less than or equal to 25 nm, or greater than or equal to 19 nm and less than or equal to 21 nm). Other ranges are also possible. In some embodiments, the average diameter of the nanowires in a plurality of nanowires is in one or more of the above-referenced ranges.

As described elsewhere herein, in some embodiments, a sensor comprises a blocking layer disposed on a portion thereof, such as on a plurality of nanowires therein. When present, the blocking layer may comprise a polymeric material, such as a protein (e.g., casein, bovine serum albumin), an oligosaccharide, a polysaccharide (e.g., carboxymethyl cellulose), a synthetic polymer (e.g., poly(vinyl pyrrolidone), poly(ethylene imine), poly(ethylene glycol)), and/or a derivative of the above-referenced polymers (e.g., an acetylated polymer, such as acetylated bovine serum albumin). In some embodiments, a blocking layer further comprises one or more stabilizers, such as a free radical absorber (e.g., histidine, a beta-mercaptan, a thiol), a pH stabilizer, and/or a moisture control agent. The stabilizer(s) may increase the shelf-life of the sensor and/or may be configured to be removed upon contact with a fluid to which the sensor is configured to be exposed, such as buffered saline and/or one or more bodily fluids. For instance, in some embodiments, the stabilizer is configured to be dissolved in a fluid to which the sensor is configured to be exposed.

As described elsewhere herein, in some embodiments, a sensor comprises one or more pairs of electrodes. Further details regarding such electrodes are provided below.

The sensors described herein may comprise a variety of suitable numbers of pairs of electrodes (e.g., that are arranged to have radial symmetry about a center point). In some embodiments, a sensor comprises greater than or equal to 5, greater than or equal to 6, greater than or equal to 7, greater than or equal to 8, greater than or equal to 9, greater than or equal to 10, greater than or equal to 11, greater than or equal to 12, greater than or equal to 13, greater than or equal to 14, greater than or equal to 15, greater than or equal to 16, greater than or equal to 17, greater than or equal to 18, greater than or equal to 19, greater than or equal to 20, greater than or equal to 21, greater than or equal to 22, greater than or equal to 23, greater than or equal to 24, greater than or equal to 25, greater than or equal to 26, greater than or equal to 27, greater than or equal to 28, greater than or equal to 29, greater than or equal to 30, greater than or equal to 31, greater than or equal to 32, greater than or equal to 34, greater than or equal to 36, greater than or equal to 38, greater than or equal to 40, or greater than or equal to 45 pairs of electrodes. In some embodiments, a sensor comprises less than or equal to 50, less than or equal to 45, less than or equal to 40, less than or equal to 38, less than or equal to 36, less than or equal to 34, less than or equal to 32, less than or equal to 31, less than or equal to 30, less than or equal to 29, less than or equal to 28, less than or equal to 27, less than or equal to 26, less than or equal to 25, less than or equal to 24, less than or equal to 23, less than or equal to 22, less than or equal to 21, less than or equal to 20, less than or equal to 19, less than or equal to 18, less than or equal to 17, less than or equal to 16, less than or equal to 15, less than or equal to 14, less than or equal to 13, less than or equal to 12, less than or equal to 11, less than or equal to 10, less than or equal to 9, less than or equal to 8, less than or equal to 7, or less than or equal to 6 pairs of electrodes. Combinations of the above-referenced ranges are also possible (e.g., greater than or equal to 5 and less than or equal to 50, greater than or equal to 10 and less than or equal to 50, greater than or equal to 10 and less than or equal to 40, or greater than or equal to 15 and less than or equal to 25). Other ranges are also possible.

The sensors described herein may comprise a variety of suitable numbers of motifs (e.g., comprising pairs of electrodes) that are arranged to have radial symmetry about a center point. In some embodiments, a sensor comprises greater than or equal to 2 or greater than or equal to 3 motifs. In some embodiments, a sensor comprises less than or equal to 4 less than or equal to 3 motifs. Combinations of the above-referenced ranges are also possible (e.g., greater than or equal to 2 and less than or equal to 4. Other ranges are also possible.

In some embodiments, a suitable percentage of the electrode pairs in a sensor (e.g., a sensor comprising a plurality of pairs of electrodes that are arranged to have radial symmetry about a center point) may be in electrical communication by exactly one nanowire. The percentage of electrode pairs in communication by exactly one nanowire may be greater than or equal to 0%, greater than or equal to 1%, greater than or equal to 2%, greater than or equal to 5%, greater than or equal to 7.5%, greater than or equal to 10%, greater than or equal to 12.5%, greater than or equal to 15%, greater than or equal to 17.5%, greater than or equal to 20%, greater than or equal to 22.5%, greater than or equal to 25%, greater than or equal to 27.5%, greater than or equal to 30%, greater than or equal to 35%, greater than or equal to 40%, greater than or equal to 45%, greater than or equal to 50%, greater than or equal to 60%, greater than or equal to 70%, greater than or equal to 80%, or greater than or equal to 90%. In some embodiments, the percentage of electrode pairs in communication by exactly one nanowire is less than or equal to 100%, less than or equal to 90%, less than or equal to 80%, less than or equal to 70%, less than or equal to 60%, less than or equal to 50%, less than or equal to 45%, less than or equal to 40%, less than or equal to 35%, less than or equal to 30%, less than or equal to 27.5%, less than or equal to 25%, less than or equal to 22.5%, less than or equal to 20%, less than or equal to 17.5%, less than or equal to 15%, less than or equal to 12.5%, less than or equal to 10%, less than or equal to 7.5%, less than or equal to 5%, less than or equal to 2%, or less than or equal to 1%. Combinations of the above-referenced ranges are also possible (e.g., greater than or equal to 0% and less than or equal to 100%, greater than or equal to 10% and less than or equal to 50%, or greater than or equal to 15% and less than or equal to 25%). Other ranges are also possible.

In some embodiments, a pair of electrodes that is in electrical communication by exactly one nanowire is also suitably configured for making a measurement of an analyte in a fluid as described elsewhere herein. Accordingly, in some embodiments, a sensor may comprise a percentage of pairs of electrodes that are acceptable for sensing in one or more of the ranges described above.

A sensor may comprise a pair of electrodes in which an inner electrode is nested inside an outer electrode. Both the inner and the outer electrode may comprise two connected portions and one portion that connects the two connected portions. The connecting portion may place the two connected portions in electrical communication with each other. The connected portions may be substantially parallel, or may be oriented with respect to each other in another manner (e.g., the two connected portions may be oriented radially outwards from a center point). It is also possible for the connected portions may be substantially straight or to comprise one or more curves, angles, and/or kinks. Similarly, the portion that connects the two connected portions may be substantially straight or may comprise one or more curves, angles, and/or kinks. By way of example, in some embodiments, a portion that connects two connected portions may comprise three sub-portions, each of which are substantially straight.

Figure 19:
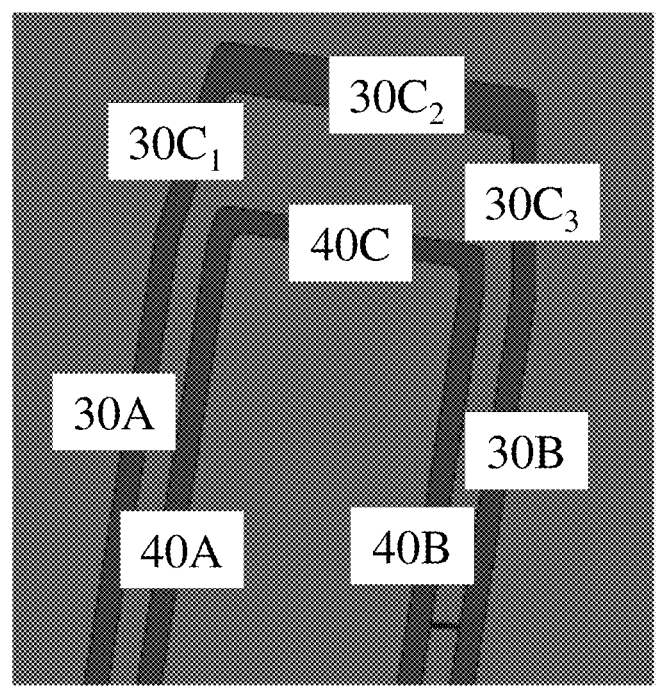
FIG. 19 shows one example of a pair of electrodes comprising one electrode including a connecting portion comprising three sub-portions, in accordance with some embodiments.

FIG. 19 shows one example of a pair of electrodes comprising one electrode including a connecting portion comprising three sub-portions. In FIG. 19, the outer electrode 30 comprises connected portions 30A and 30B. It further comprises a connecting portion 30C comprising the subportions 30C1, 30C2, and 30C3. FIG. 19 also shows an inner electrode 40 that comprises connected portions 40A and 40B, and further comprises a connecting portion 40C that is substantially straight. In embodiments like FIG. 19, in which an inner electrode comprises a connecting portion that is substantially straight and an outer electrode comprises a connecting portion that comprises three subportions, the lengths of the connected portions for the inner electrode may be substantially the same as those for the outer electrode (e.g., their lengths may be within 5%, 2%, or 1% of each other). As also shown in FIG. 19, the connected portions of the inner and outer electrodes that are adjacent to each other may be substantially parallel. With reference to FIG. 19, the connected portion 40A of the inner electrode 40 is substantially parallel to the connected portion 30A of the outer electrode 30 and the connected portion of 40B of the inner electrode 40 is substantially parallel to the connected portion 30B of the outer electrode 30.

It should be noted that, when a pair of electrodes comprises an inner electrode and an outer electrode, either electrode may be the source electrode and either electrode may be the drain electrode.

The dimensions of each portion of the electrode may generally be selected as desired. In some embodiments, an outer electrode (e.g., an electrode comprising connected portions positioned around connected portions of an inner electrode) comprises connected portions having a length of greater than or equal to 100 microns, greater than or equal to 125 microns, greater than or equal to 150 microns, greater than or equal to 175 microns, greater than or equal to 200 microns, greater than or equal to 225 microns, greater than or equal to 250 microns, greater than or equal to 275 microns, greater than or equal to 300 microns, greater than or equal to 325 microns, greater than or equal to 344 microns, greater than or equal to 375 microns, greater than or equal to 400 microns, greater than or equal to 450 microns, greater than or equal to 500 microns, greater than or equal to 600 microns, or greater than or equal to 800 microns. In some embodiments, an outer electrode comprises connected portions having a length of less than or equal to 1,000 microns, less than or equal to 800 microns, less than or equal to 600 microns, less than or equal to 500 microns, less than or equal to 450 microns, less than or equal to 400 microns, less than or equal to 375 microns, less than or equal to 344 microns, less than or equal to 325 microns, less than or equal to 300 microns, less than or equal to 275 microns, less than or equal to 250 microns, less than or equal to 225 microns, less than or equal to 200 microns, less than or equal to 175 microns, less than or equal to 150 microns, or less than or equal to 125 microns. Combinations of the above-referenced ranges are also possible (e.g., greater than or equal to 100 microns and less than or equal to 1,000 microns, or greater than or equal to 300 and less than or equal to 400 microns). Other ranges are also possible.

Two connected portions of an outer electrode may have substantially the same length (e.g., they may have lengths within 5%, 2%, or 1% of each other) or may have lengths that differ from each other. When a pair of connected portions of an outer electrode have different lengths, each such electrode portion may independently have a length in one or more of the ranges described above.

In some embodiments, an outer electrode (e.g., an electrode comprising connected portions positioned around the connected portions of an inner electrode) comprises connected portions having a width of greater than or equal to 1 micron, greater than or equal to 1.5 microns, greater than or equal to 2 microns, greater than or equal to 2.5 microns, greater than or equal to 3 microns, greater than or equal to 3.5 microns, greater than or equal to 4 microns, greater than or equal to 4.5 microns, greater than or equal to 5 microns, greater than or equal to 5.5 microns, greater than or equal to 6 microns, greater than or equal to 6.5 microns, greater than or equal to 7 microns, greater than or equal to 7.5 microns, greater than or equal to 8 microns, greater than or equal to 9 microns, greater than or equal to 10 microns, greater than or equal to 15 microns, greater than or equal to 20 microns, greater than or equal to 50 microns, greater than or equal to 75 microns, greater than or equal to 100 microns, greater than or equal to 150 microns, greater than or equal to 200 microns, or greater than or equal to 250 microns. In some embodiments, an outer electrode comprises connected portions having a width of less than or equal to 300 microns, less than or equal to 250 microns, less than or equal to 200 microns, less than or equal to 150 microns, less than or equal to 100 microns, less than or equal to 75 microns, less than or equal to 50 microns, less than or equal to 20 microns, less than or equal to 15 microns, less than or equal to 10 microns, less than or equal to 9 microns, less than or equal to 8 microns, less than or equal to 7.5 microns, less than or equal to 7 microns, less than or equal to 6.5 microns, less than or equal to 6 microns, less than or equal to 5.5 microns, less than or equal to 5 microns, less than or equal to 4.5 microns, less than or equal to 4 microns, less than or equal to 3.5 microns, less than or equal to 3 microns, less than or equal to 2.5 microns, less than or equal to 2 microns, or less than or equal to 1.5 microns. Combinations of the above-referenced ranges are also possible (e.g., greater than or equal to 1 micron and less than or equal to 300 microns, or greater than or equal to 3 and less than or equal to 7 microns). Other ranges are also possible.

Two connected portions of an outer electrode may have substantially the same width (e.g., they may have widths within 10%, 5%, 2%, or 1% of each other) or may have widths that differ from each other. When a pair of connected portions of an outer electrode have different widths, each such electrode portion may independently have a width in one or more of the ranges described above. It should also be understood that the values listed above may independently describe the average width of the connected portions of the outer electrode or the median width of the connected portions of the outer electrode.

In some embodiments, an outer electrode (e.g., an electrode comprising connected portions positioned around the connected portions of an inner electrode) comprises connected portions having a height of greater than or equal to 0.05 microns, greater than or equal to 0.01 micron, greater than or equal to 0.02 microns, greater than or equal to 0.05 microns, greater than or equal to 0.075 microns, greater than or equal to 0.1 micron, greater than or equal to 0.15 microns, greater than or equal to 0.175 microns, greater than or equal to 0.2 microns, greater than or equal to 0.225 microns, greater than or equal to 0.25 microns, greater than or equal to 0.275 microns, greater than or equal to 0.3 microns, greater than or equal to 0.325 microns, greater than or equal to 0.35 microns, greater than or equal to 0.375 microns, greater than or equal to 0.4 microns, or greater than or equal to 0.45 microns. In some embodiments, an outer electrode comprises connected portions having a height of less than or equal to 0.5 microns, less than or equal to 0.45 microns, less than or equal to 0.4 microns, less than or equal to 0.375 microns, less than or equal to 0.35 microns, less than or equal to 0.325 microns, less than or equal to 0.3 microns, less than or equal to 0.275 microns, less than or equal to 0.25 microns, less than or equal to 0.225 microns, less than or equal to 0.2 microns, less than or equal to 0.175 microns, less than or equal to 0.15 microns, less than or equal to 0.1 micron, less than or equal to 0.075 microns, less than or equal to 0.05 microns, less than or equal to 0.02 microns, or less than or equal to 0.01 micron. Combinations of the above-referenced ranges are also possible (e.g., greater than or equal to 0.05 microns and less than or equal to 0.5 microns, or greater than or equal to 0.15 microns and less than or equal to 0.35 microns). Other ranges are also possible.

Two connected portions of an outer electrode may have substantially the same height (e.g., they may have heights within 10%, 5%, 2%, or 1% of each other) or may have heights that differ from each other. When a pair of connected portions of an outer electrode have different heights, each such electrode portion may independently have a height in one or more of the ranges described above. It should also be understood that the values listed above may independently describe the average height of the connected portions of the outer electrode or the median height of the connected portions of the outer electrode.

A portion of an outer electrode (e.g., an electrode comprising connected portions positioned around the connected portions of an inner electrode) connecting two connected portions thereof may have a length of greater than or equal to 50 microns, greater than or equal to 52 microns, greater than or equal to 55 microns, greater than or equal to 57 microns, greater than or equal to 60 microns, greater than or equal to 62 microns, greater than or equal to 65 microns, greater than or equal to 67 microns, greater than or equal to 70 microns, greater than or equal to 72 microns, greater than or equal to 75 microns, or greater than or equal to 77 microns. In some embodiments, a portion of an outer electrode connecting two connected portions thereof has a length of less than or equal to 80 microns, less than or equal to 77 microns, less than or equal to 75 microns, less than or equal to 72 microns, less than or equal to 70 microns, less than or equal to 67 microns, less than or equal to 65 microns, less than or equal to 62 microns, less than or equal to 60 microns, less than or equal to 57 microns, less than or equal to 55 microns, less than or equal to 52 microns, or less than or equal to 50 microns. Combinations of the above-referenced ranges are also possible (e.g., greater than or equal to 50 microns and less than or equal to 80 microns, or greater than or equal to 60 microns and less than or equal to 67 microns). Other ranges are also possible.

It should also be understood that the values listed above may independently describe the length of a connecting portion of an outer electrode from one end to the other, the spacing between the connected portions of the outer electrode, the length of the longest portion of the connecting portion, and/or the length of the connecting portion oriented at the largest angle to the connected portions.

A portion of an outer electrode (e.g., an electrode comprising connected portions positioned around the connected portions of an inner electrode) connecting two connected portions thereof may have a width of greater than or equal to 5 microns, greater than or equal to 6 microns, greater than or equal to 7 microns, greater than or equal to 8 microns, greater than or equal to 9 microns, greater than or equal to 10 microns, greater than or equal to 11 microns, greater than or equal to 12 microns, greater than or equal to 13 microns, or greater than or equal to 14 microns. In some embodiments, a portion of an outer electrode connecting two connected portions thereof has a width of less than or equal to 15 microns, less than or equal to 14 microns, less than or equal to 13 microns, less than or equal to 12 microns, less than or equal to 11 microns, less than or equal to 10 microns, less than or equal to 9 microns, less than or equal to 8 microns, less than or equal to 7 microns, or less than or equal to 6 microns. Combinations of the above-referenced ranges are also possible (e.g., greater than or equal to 5 microns and less than or equal to 10 microns). Other ranges are also possible.

It should also be understood that the values listed above may independently describe the average width of a portion of the outer electrode connecting two connected portions thereof or the median width of the portion of the outer electrode connecting two connected portions thereof.

A portion of an outer electrode (e.g., an electrode comprising connected portions positioned around the connected portions of an inner electrode) connecting two connected portions thereof may have a height of greater than or equal to 0.005 microns, greater than or equal to greater than or equal to 0.0075 microns, greater than or equal to 0.01 micron, greater than or equal to 0.02 microns, greater than or equal to 0.05 microns, greater than or equal to 0.075 microns, greater than or equal to 0.1 micron, greater than or equal to 0.15 microns, greater than or equal to 0.175 microns, greater than or equal to 0.2 microns, greater than or equal to 0.225 microns, greater than or equal to 0.25 microns, greater than or equal to 0.275 microns, greater than or equal to 0.3 microns, greater than or equal to 0.325 microns, greater than or equal to 0.35 microns, greater than or equal to 0.375 microns, greater than or equal to 0.4 microns, or greater than or equal to 0.45 microns. In some embodiments, a portion of an outer electrode connecting two connected portions thereof has a height of less than or equal to 0.5 microns, less than or equal to 0.45 microns, less than or equal to 0.4 microns, less than or equal to 0.375 microns, less than or equal to 0.35 microns, less than or equal to 0.325 microns, less than or equal to 0.3 microns, less than or equal to 0.275 microns, less than or equal to 0.25 microns, less than or equal to 0.225 microns, less than or equal to 0.2 microns, less than or equal to 0.175 microns, less than or equal to 0.15 microns, less than or equal to 0.1 micron, less than or equal to 0.075 microns, less than or equal to 0.05 microns, less than or equal to 0.02 microns, less than or equal to 0.01 micron, or less than or equal to 0.0075 microns. Combinations of the above-referenced ranges are also possible (e.g., greater than or equal to 0.005 microns and less than or equal to 0.5 microns, greater than or equal to 0.05 microns and less than or equal to 0.5 microns, or greater than or equal to 0.15 microns and less than or equal to 0.35 microns). Other ranges are also possible.

It should also be understood that the values listed above may independently describe the average height of a portion of the outer electrode connecting two connected portions thereof or the median height of the portion of the outer electrode connecting two connected portions thereof.

In some embodiments, an inner electrode (e.g., an electrode comprising connected portions positioned between the connected portions of an outer electrode) comprises connected portions having a length of greater than or equal to 100 microns, greater than or equal to 125 microns, greater than or equal to 150 microns, greater than or equal to 175 microns, greater than or equal to 200 microns, greater than or equal to 225 microns, greater than or equal to 250 microns, greater than or equal to 275 microns, greater than or equal to 300 microns, greater than or equal to 325 microns, greater than or equal to 344 microns, greater than or equal to 375 microns, greater than or equal to 400 microns, greater than or equal to 450 microns, greater than or equal to 500 microns, greater than or equal to 600 microns, or greater than or equal to 800 microns. In some embodiments, an inner electrode comprises connected portions having a length of less than or equal to 1,000 microns, less than or equal to 800 microns, less than or equal to 600 microns, less than or equal to 500 microns, less than or equal to 450 microns, less than or equal to 400 microns, less than or equal to 375 microns, less than or equal to 344 microns, less than or equal to 325 microns, less than or equal to 300 microns, less than or equal to 275 microns, less than or equal to 250 microns, less than or equal to 225 microns, less than or equal to 200 microns, less than or equal to 175 microns, less than or equal to 150 microns, or less than or equal to 125 microns. Combinations of the above-referenced ranges are also possible (e.g., greater than or equal to 100 microns and less than or equal to 1,000 microns, or greater than or equal to 300 and less than or equal to 400 microns). Other ranges are also possible.

Two connected portions of an inner electrode may have substantially the same length (e.g., they may have lengths within 5%, 2%, or 1% of each other) or may have lengths that differ from each other. When a pair of connected portions of an inner electrode have different lengths, each such electrode portion may independently have a length in one or more of the ranges described above.

In some embodiments, an inner electrode (e.g., an electrode comprising connected portions positioned between the connected portions of an outer electrode) comprises connected portions having a width of greater than or equal to 1 micron, greater than or equal to 1.5 microns, greater than or equal to 2 microns, greater than or equal to 2.5 microns, greater than or equal to 3 microns, greater than or equal to 3.5 microns, greater than or equal to 4 microns, greater than or equal to 4.5 microns, greater than or equal to 5 microns, greater than or equal to 5.5 microns, greater than or equal to 6 microns, greater than or equal to 6.5 microns, greater than or equal to 7 microns, greater than or equal to 7.5 microns, greater than or equal to 8 microns, greater than or equal to 9 microns, greater than or equal to 10 microns, greater than or equal to 15 microns, greater than or equal to 20 microns, greater than or equal to 50 microns, greater than or equal to 75 microns, greater than or equal to 100 microns, greater than or equal to 150 microns, greater than or equal to 200 microns, or greater than or equal to 250 microns. In some embodiments, an inner electrode comprises connected portions having a width of less than or equal to 300 microns, less than or equal to 250 microns, less than or equal to 200 microns, less than or equal to 150 microns, less than or equal to 100 microns, less than or equal to 75 microns, less than or equal to 50 microns, less than or equal to 20 microns, less than or equal to 15 microns, less than or equal to 10 microns, less than or equal to 9 microns, less than or equal to 8 microns, less than or equal to 7.5 microns, less than or equal to 7 microns, less than or equal to 6.5 microns, less than or equal to 6 microns, less than or equal to 5.5 microns, less than or equal to 5 microns, less than or equal to 4.5 microns, less than or equal to 4 microns, less than or equal to 3.5 microns, less than or equal to 3 microns, less than or equal to 2.5 microns, less than or equal to 2 microns, or less than or equal to 1.5 microns. Combinations of the above-referenced ranges are also possible (e.g., greater than or equal to 1 micron and less than or equal to 300 microns, or greater than or equal to 3 microns and less than or equal to 7 microns). Other ranges are also possible.

Two connected portions of an inner electrode may have substantially the same width (e.g., they may have widths within 5%, 2%, or 1% of each other) or may have widths that differ from each other. When a pair of connected portions of an inner electrode have different widths, each such electrode portion may independently have a width in one or more of the ranges described above. It should also be understood that the values listed above may independently describe the average width of the connected portions of the inner electrode or the median width of the connected portions of the inner electrode.

In some embodiments, an inner electrode (e.g., an electrode comprising connected portions positioned between the connected portions of an outer electrode) comprises connected portions having a height of greater than or equal to 0.05 microns, greater than or equal to 0.01 micron, greater than or equal to 0.02 microns, greater than or equal to 0.05 microns, greater than or equal to 0.075 microns, greater than or equal to 0.1 micron, greater than or equal to 0.15 microns, greater than or equal to 0.175 microns, greater than or equal to 0.2 microns, greater than or equal to 0.225 microns, greater than or equal to 0.25 microns, greater than or equal to 0.275 microns, greater than or equal to 0.3 microns, greater than or equal to 0.325 microns, greater than or equal to 0.35 microns, greater than or equal to 0.375 microns, greater than or equal to 0.4 microns, or greater than or equal to 0.45 microns. In some embodiments, an inner electrode comprises connected portions having a height of less than or equal to 0.5 microns, less than or equal to 0.45 microns, less than or equal to 0.4 microns, less than or equal to 0.375 microns, less than or equal to 0.35 microns, less than or equal to 0.325 microns, less than or equal to 0.3 microns, less than or equal to 0.275 microns, less than or equal to 0.25 microns, less than or equal to 0.225 microns, less than or equal to 0.2 microns, less than or equal to 0.175 microns, less than or equal to 0.15 microns, less than or equal to 0.1 micron, less than or equal to 0.075 microns, less than or equal to 0.05 microns, less than or equal to 0.02 microns, or less than or equal to 0.01 micron. Combinations of the above-referenced ranges are also possible (e.g., greater than or equal to 0.05 microns and less than or equal to 0.5 microns, or greater than or equal to 0.15 microns and less than or equal to 0.35 microns). Other ranges are also possible.

Two connected portions of an inner electrode may have substantially the same height (e.g., they may have heights within 10%, 5%, 2%, or 1% of each other) or may have heights that differ from each other. When a pair of connected portions of an inner electrode have different heights, each such electrode portion may independently have a height in one or more of the ranges described above. It should also be understood that the values listed above may independently describe the average height of the connected portions of the inner electrode or the median height of the connected portions of the inner electrode.

A portion of an inner electrode (e.g., an electrode comprising connected portions positioned between the connected portions of an outer electrode) connecting two connected portions thereof may have a length of greater than or equal to 40 microns, greater than or equal to 41 microns, greater than or equal to 42 microns, greater than or equal to 43 microns, greater than or equal to 44 microns, greater than or equal to 45 microns, greater than or equal to 46 microns, greater than or equal to 47 microns, greater than or equal to 48 microns, greater than or equal to 49 microns, greater than or equal to 50 microns, greater than or equal to 51 microns, greater than or equal to 52 microns, greater than or equal to 53 microns, or greater than or equal to 54 microns. In some embodiments, a portion of an inner electrode connecting two connected portions thereof has a length of less than or equal to 55 microns, less than or equal to 54 microns, less than or equal to 53 microns, less than or equal to 52 microns, less than or equal to 51 microns, less than or equal to 50 microns, less than or equal to 49 microns, less than or equal to 48 microns, less than or equal to 47 microns, less than or equal to 46 microns, less than or equal to 45 microns, less than or equal to 44 microns, less than or equal to 43 microns, less than or equal to 42 microns, or less than or equal to 41 microns. Combinations of the above-referenced ranges are also possible (e.g., greater than or equal to 40 microns and less than or equal to 50 microns, or greater than or equal to 45 microns and less than or equal to 55 microns). Other ranges are also possible.

It should also be understood that the values listed above may independently describe the length of a connecting portion of an inner electrode from one end to the other, the spacing between the connected portions of the inner electrode, the length of the longest portion of the connecting portion, and/or the length of the connecting portion oriented at the largest angle with the connected portions.

A portion of an inner electrode (e.g., an electrode comprising connected portions positioned between the connected portions of an outer electrode) connecting two connected portions thereof may have a width of greater than or equal to 1 micron, greater than or equal to 1.5 microns, greater than or equal to 2 microns, greater than or equal to 2.5 microns, greater than or equal to 3 microns, greater than or equal to 3.5 microns, greater than or equal to 4 microns, greater than or equal to 4.5 microns, greater than or equal to 5 microns, greater than or equal to 5.5 microns, greater than or equal to 6 microns, greater than or equal to 6.5 microns, greater than or equal to 7 microns, greater than or equal to 7.5 microns, greater than or equal to 8 microns, greater than or equal to 9 microns, greater than or equal to 10 microns, greater than or equal to 15 microns, greater than or equal to 20 microns, greater than or equal to 50 microns, greater than or equal to 75 microns, greater than or equal to 100 microns, greater than or equal to 150 microns, greater than or equal to 200 microns, or greater than or equal to 250 microns. In some embodiments, a portion of an inner electrode connecting two connected portions thereof has a width of less than or equal to 300 microns, less than or equal to 250 microns, less than or equal to 200 microns, less than or equal to 150 microns, less than or equal to 100 microns, less than or equal to 75 microns, less than or equal to 50 microns, less than or equal to 20 microns, less than or equal to 15 microns, less than or equal to 10 microns, less than or equal to 9 microns, less than or equal to 8 microns, less than or equal to 7.5 microns, less than or equal to 7 microns, less than or equal to 6.5 microns, less than or equal to 6 microns, less than or equal to 5.5 microns, less than or equal to 5 microns, less than or equal to 4.5 microns, less than or equal to 4 microns, less than or equal to 3.5 microns, less than or equal to 3 microns, less than or equal to 2.5 microns, less than or equal to 2 microns, or less than or equal to 1.5 microns. Combinations of the above-referenced ranges are also possible (e.g., greater than or equal to 1 micron and less than or equal to 300 microns, or greater than or equal to 3 and less than or equal to 7 microns). Other ranges are also possible.

It should also be understood that the values listed above may independently describe the average width of a portion of the inner electrode connecting two connected portions thereof or the median width of the portion of the inner electrode connecting two connected portions thereof.

A portion of an inner electrode (e.g., an electrode comprising connected portions positioned between the connected portions of an outer electrode) connecting two connected portions thereof may have a height of greater than or equal to 0.005 microns, greater than or equal to greater than or equal to 0.0075 microns, greater than or equal to 0.01 micron, greater than or equal to 0.02 microns, greater than or equal to 0.05 microns, greater than or equal to 0.075 microns, greater than or equal to 0.1 micron, greater than or equal to 0.15 microns, greater than or equal to 0.175 microns, greater than or equal to 0.2 microns, greater than or equal to 0.225 microns, greater than or equal to 0.25 microns, greater than or equal to 0.275 microns, greater than or equal to 0.3 microns, greater than or equal to 0.325 microns, greater than or equal to 0.35 microns, greater than or equal to 0.375 microns, greater than or equal to 0.4 microns, or greater than or equal to 0.45 microns. In some embodiments, a portion of an inner electrode connecting two connected portions thereof has a height of less than or equal to 0.5 microns, less than or equal to 0.45 microns, less than or equal to 0.4 microns, less than or equal to 0.375 microns, less than or equal to 0.35 microns, less than or equal to 0.325 microns, less than or equal to 0.3 microns, less than or equal to 0.275 microns, less than or equal to 0.25 microns, less than or equal to 0.225 microns, less than or equal to 0.2 microns, less than or equal to 0.175 microns, less than or equal to 0.15 microns, less than or equal to 0.1 micron, less than or equal to 0.075 microns, less than or equal to 0.05 microns, less than or equal to 0.02 microns, less than or equal to 0.01 micron, or less than or equal to 0.0075 microns. Combinations of the above-referenced ranges are also possible (e.g., greater than or equal to 0.05 microns and less than or equal to 0.5 microns, or greater than or equal to 0.15 microns and less than or equal to 0.35 microns). Other ranges are also possible.

It should also be understood that the values listed above may independently describe the average height of a portion of the inner electrode connecting two connected portions thereof or the median height of the portion of the inner electrode connecting two connected portions thereof.

When a pair of electrodes comprises an outer electrode and an inner electrode, the spacing therebetween may be selected as desired. In some embodiments, the distance between one of the connected portions of an outer electrode and the connected portion of the inner electrode to which it is closest (e.g., the distance between portions 30A and 40A in FIG. 19, or the distance between portions 30B and 40B in FIG. 19) is greater than or equal to 1 micron, greater than or equal to 1.25 microns, greater than or equal to 1.5 microns, greater than or equal to 1.75 microns, greater than or equal to 2 microns, greater than or equal to 2.25 microns, greater than or equal to 2.5 microns, greater than or equal to 3 microns, greater than or equal to 3.5 microns, greater than or equal to 4 microns, greater than or equal to 5 microns, greater than or equal to 6 microns, greater than or equal to 7 microns, greater than or equal to 8 microns, greater than or equal to 8.5 microns, greater than or equal to 9 microns, greater than or equal to 9.25 microns, greater than or equal to 9.5 microns, greater than or equal to 9.75 microns, greater than or equal to 10 microns, greater than or equal to 10.5 microns, greater than or equal to 11 microns, greater than or equal to 11.5 microns, greater than or equal to 12 microns, greater than or equal to 12.5 microns, greater than or equal to 13 microns, greater than or equal to 13.5 microns, greater than or equal to 14 microns, greater than or equal to 15 microns, greater than or equal to 17.5 microns, greater than or equal to 20 microns, greater than or equal to 25 microns, greater than or equal to 30 microns, greater than or equal to 35 microns, or greater than or equal to 40 microns. In some embodiments, the distance between one of the connected portions of an outer electrode and the connected portion of the inner electrode to which it is closest is less than or equal to 50 microns, less than or equal to 40 microns, less than or equal to 35 microns, less than or equal to 25 microns, less than or equal to 20 microns, less than or equal to 17.5 microns, less than or equal to 15 microns, less than or equal to 14 microns, less than or equal to 13.5 microns, less than or equal to 13 microns, less than or equal to 12.5 microns, less than or equal to 12 microns, less than or equal to 11.5 microns, less than or equal to 11 microns, less than or equal to 10.5 microns, less than or equal to 10 microns, less than or equal to 9.75 microns, less than or equal to 9.5 microns, less than or equal to 9.25 microns, less than or equal to 9 microns, less than or equal to 8.5 microns, less than or equal to 8 microns, less than or equal to 7 microns, less than or equal to 6 microns, less than or equal to 5 microns, less than or equal to 4 microns, less than or equal to 3.5 microns, less than or equal to 3 microns, less than or equal to 2.5 microns, less than or equal to 2.25 microns, less than or equal to 2 microns, less than or equal to 1.75 microns, less than or equal to 1.5 microns, or less than or equal to 1.25 microns. Combinations of the above-referenced ranges are also possible (e.g., greater than or equal to 1 micron and less than or equal to 50 microns, greater than or equal to 1.5 microns and less than or equal to 12 microns, greater than or equal to 5 microns and less than or equal to 15 microns, or greater than or equal to 9 microns and less than or equal to 10 microns). Other ranges are also possible.

It should also be understood that the values listed above may independently describe the average distance between one of the connected portions of an outer electrode and the connected portion of the inner electrode to which it is closest, the median distance between one of the connected portions of an outer electrode and the connected portion of the inner electrode to which it is closest, or the minimum distance between one of the connected portions of an outer electrode and the connected portion of the inner electrode to which it is closest.

In some embodiments, the distance between one of the connected portions of an outer electrode and the connected portion of the inner electrode to which it is closest may be relatively close to the length of a nanowire placing the inner and outer electrodes in electrical communication. In some embodiments, the ratio of the length of the nanowire to the distance between one of the connected portions of an outer electrode and the connected portion of the inner electrode to which it is closest is greater than or equal to 1, greater than or equal to 1.5, greater than or equal to 2, greater than or equal to 2.5, greater than or equal to 3, greater than or equal to 3.5, greater than or equal to 4, or greater than or equal to 4.5. In some embodiments, the ratio of the length of the nanowire to the distance between one of the connected portions of an outer electrode and the connected portion of the inner electrode to which it is closest is less than or equal to 5, less than or equal to 4.5, less than or equal to 4, less than or equal to 3.5, less than or equal to 3, less than or equal to 2.5, less than or equal to 2, or less than or equal to 1.5. Combinations of the above-referenced ranges are also possible (e.g., greater than or equal to 1 and less than or equal to 5). Other ranges are also possible.

It should also be understood that the ratios listed above may independently describe the ratio of the length of the nanowire to the average distance between one of the connected portions of an outer electrode and the connected portion of the inner electrode to which it is closest, the ratio of the length of the nanowire to the median distance between one of the connected portions of an outer electrode and the connected portion of the inner electrode to which it is closest, or the ratio of the length of the nanowire to the minimum distance between one of the connected portions of an outer electrode and the connected portion of the inner electrode to which it is closest.

As described elsewhere herein, in some embodiments, a pair of electrodes comprises two electrodes that are straight and parallel to each other (e.g., they may have a structure like that shown in FIG. 1) and/or a plurality of electrodes comprises an array of electrodes that are straight and parallel to each other.

The dimensions of electrodes that are straight and parallel to each other may generally be selected as desired. In some embodiments, such an electrode comprises has a length of greater than or equal to 100 microns, greater than or equal to 125 microns, greater than or equal to 150 microns, greater than or equal to 175 microns, greater than or equal to 200 microns, greater than or equal to 225 microns, greater than or equal to 250 microns, greater than or equal to 275 microns, greater than or equal to 300 microns, greater than or equal to 325 microns, greater than or equal to 344 microns, greater than or equal to 375 microns, greater than or equal to 400 microns, greater than or equal to 450 microns, greater than or equal to 500 microns, greater than or equal to 600 microns, or greater than or equal to 800 microns. In some embodiments, a straight electrode has a length of less than or equal to 1,000 microns, less than or equal to 800 microns, less than or equal to 600 microns, less than or equal to 500 microns, less than or equal to 450 microns, less than or equal to 400 microns, less than or equal to 375 microns, less than or equal to 344 microns, less than or equal to 325 microns, less than or equal to 300 microns, less than or equal to 275 microns, less than or equal to 250 microns, less than or equal to 225 microns, less than or equal to 200 microns, less than or equal to 175 microns, less than or equal to 150 microns, or less than or equal to 125 microns. Combinations of the above-referenced ranges are also possible (e.g., greater than or equal to 100 microns and less than or equal to 1,000 microns, or greater than or equal to 300 and less than or equal to 400 microns). Other ranges are also possible.

Straight and parallel electrodes may have substantially the same length (e.g., they may have lengths within 5%, 2%, or 1% of each other) or may have lengths that differ from each other. When a plurality of straight and parallel electrodes comprises electrodes having different lengths, each such electrode may independently have a length in one or more of the ranges described above.

In some embodiments, a straight electrode has a width of greater than or equal to 1 micron, greater than or equal to 1.5 microns, greater than or equal to 2 microns, greater than or equal to 2.5 microns, greater than or equal to 3 microns, greater than or equal to 3.5 microns, greater than or equal to 4 microns, greater than or equal to 4.5 microns, greater than or equal to 5 microns, greater than or equal to 5.5 microns, greater than or equal to 6 microns, greater than or equal to 6.5 microns, greater than or equal to 7 microns, greater than or equal to 7.5 microns, greater than or equal to 8 microns, greater than or equal to 9 microns, greater than or equal to 10 microns, greater than or equal to 15 microns, greater than or equal to 20 microns, greater than or equal to 50 microns, greater than or equal to 75 microns, greater than or equal to 100 microns, greater than or equal to 150 microns, greater than or equal to 200 microns, or greater than or equal to 250 microns. In some embodiments, a straight electrode has a width of less than or equal to 300 microns, less than or equal to 250 microns, less than or equal to 200 microns, less than or equal to 150 microns, less than or equal to 100 microns, less than or equal to 75 microns, less than or equal to 50 microns, less than or equal to 20 microns, less than or equal to 15 microns, less than or equal to 10 microns, less than or equal to 9 microns, less than or equal to 8 microns, less than or equal to 7.5 microns, less than or equal to 7 microns, less than or equal to 6.5 microns, less than or equal to 6 microns, less than or equal to 5.5 microns, less than or equal to 5 microns, less than or equal to 4.5 microns, less than or equal to 4 microns, less than or equal to 3.5 microns, less than or equal to 3 microns, less than or equal to 2.5 microns, less than or equal to 2 microns, or less than or equal to 1.5 microns. Combinations of the above-referenced ranges are also possible (e.g., greater than or equal to 1 micron and less than or equal to 300 microns, or greater than or equal to 3 and less than or equal to 7 microns). Other ranges are also possible.

Straight and parallel electrodes may have substantially the same width (e.g., they may have widths within 5%, 2%, or 1% of each other) or may have widths that differ from each other. When a plurality of straight and parallel electrodes comprises electrodes having different widths, each such electrode may independently have a width in one or more of the ranges described above.

In some embodiments, a straight electrode has a height of greater than or equal to 0.05 microns, greater than or equal to 0.01 micron, greater than or equal to 0.02 microns, greater than or equal to 0.05 microns, greater than or equal to 0.075 microns, greater than or equal to 0.1 micron, greater than or equal to 0.15 microns, greater than or equal to 0.175 microns, greater than or equal to 0.2 microns, greater than or equal to 0.225 microns, greater than or equal to 0.25 microns, greater than or equal to 0.275 microns, greater than or equal to 0.3 microns, greater than or equal to 0.325 microns, greater than or equal to 0.35 microns, greater than or equal to 0.375 microns, greater than or equal to 0.4 microns, or greater than or equal to 0.45 microns. In some embodiments, a straight electrode has a height of less than or equal to 0.5 microns, less than or equal to 0.45 microns, less than or equal to 0.4 microns, less than or equal to 0.375 microns, less than or equal to 0.35 microns, less than or equal to 0.325 microns, less than or equal to 0.3 microns, less than or equal to 0.275 microns, less than or equal to 0.25 microns, less than or equal to 0.225 microns, less than or equal to 0.2 microns, less than or equal to 0.175 microns, less than or equal to 0.15 microns, less than or equal to 0.1 micron, less than or equal to 0.075 microns, less than or equal to 0.05 microns, less than or equal to 0.02 microns, or less than or equal to 0.01 micron. Combinations of the above-referenced ranges are also possible (e.g., greater than or equal to 0.05 microns and less than or equal to 0.5 microns, or greater than or equal to 0.15 microns and less than or equal to 0.35 microns). Other ranges are also possible.

Straight and parallel electrodes may have substantially the same height (e.g., they may have heights within 5%, 2%, or 1% of each other) or may have heights that differ from each other. When a plurality of straight and parallel electrodes comprises electrodes having different heights, each such electrode may independently have a height in one or more of the ranges described above.

In some embodiments, the distance between straight and parallel electrodes is greater than or equal to 1 micron, greater than or equal to 1.25 microns, greater than or equal to 1.5 microns, greater than or equal to 1.75 microns, greater than or equal to 2 microns, greater than or equal to 2.25 microns, greater than or equal to 2.5 microns, greater than or equal to 3 microns, greater than or equal to 3.5 microns, greater than or equal to 4 microns, greater than or equal to 5 microns, greater than or equal to 6 microns, greater than or equal to 7 microns, greater than or equal to 8 microns, greater than or equal to 8.5 microns, greater than or equal to 9 microns, greater than or equal to 9.25 microns, greater than or equal to 9.5 microns, greater than or equal to 9.75 microns, greater than or equal to 10 microns, greater than or equal to 10.5 microns, greater than or equal to 11 microns, greater than or equal to 11.5 microns, greater than or equal to 12 microns, greater than or equal to 12.5 microns, greater than or equal to 13 microns, greater than or equal to 13.5 microns, greater than or equal to 14 microns, greater than or equal to 15 microns, greater than or equal to 17.5 microns, greater than or equal to 20 microns, greater than or equal to 25 microns, greater than or equal to 30 microns, greater than or equal to 35 microns, or greater than or equal to 40 microns. In some embodiments, the distance between straight and parallel electrodes is less than or equal to 50 microns, less than or equal to 40 microns, less than or equal to 35 microns, less than or equal to 25 microns, less than or equal to 20 microns, less than or equal to 17.5 microns, less than or equal to 15 microns, less than or equal to 14 microns, less than or equal to 13.5 microns, less than or equal to 13 microns, less than or equal to 12.5 microns, less than or equal to 12 microns, less than or equal to 11.5 microns, less than or equal to 11 microns, less than or equal to 10.5 microns, less than or equal to 10 microns, less than or equal to 9.75 microns, less than or equal to 9.5 microns, less than or equal to 9.25 microns, less than or equal to 9 microns, less than or equal to 8.5 microns, less than or equal to 8 microns, less than or equal to 7 microns, less than or equal to 6 microns, less than or equal to 5 microns, less than or equal to 4 microns, less than or equal to 3.5 microns, less than or equal to 3 microns, less than or equal to 2.5 microns, less than or equal to 2.25 microns, less than or equal to 2 microns, less than or equal to 1.75 microns, less than or equal to 1.5 microns, or less than or equal to 1.25 microns. Combinations of the above-referenced ranges are also possible (e.g., greater than or equal to 1 micron and less than or equal to 50 microns, greater than or equal to 1.5 microns and less than or equal to 12 microns, greater than or equal to 5 microns and less than or equal to 15 microns, or greater than or equal to 9 microns and less than or equal to 10 microns). Other ranges are also possible.

Pairs of nearest neighbor straight and parallel electrodes may have substantially the same distance therebetween (e.g., they may have be separated by distances within 5%, 2%, or 1% of each other) or may be separated by distances that differ from each other. When a plurality of straight and parallel electrodes comprises electrodes pairs of nearest neighbor electrodes separated by different distances, each nearest neighbor distance may independently be in one or more of the ranges described above.

In some embodiments, the distance between two straight and parallel electrodes may be relatively close to the length of a nanowire placing them in electrical communication. In some embodiments, the ratio of the length of the nanowire to the distance two straight and parallel electrodes is greater than or equal to 1, greater than or equal to 1.5, greater than or equal to 2, greater than or equal to 2.5, greater than or equal to 3, greater than or equal to 3.5, greater than or equal to 4, or greater than or equal to 4.5. In some embodiments, the ratio of the length of the nanowire to the distance between two straight and parallel electrodes is less than or equal to 5, less than or equal to 4.5, less than or equal to 4, less than or equal to 3.5, less than or equal to 3, less than or equal to 2.5, less than or equal to 2, or less than or equal to 1.5. Combinations of the above-referenced ranges are also possible (e.g., greater than or equal to 1 and less than or equal to 5). Other ranges are also possible.

The electrodes described herein may comprise and/or be formed from a variety of suitable materials. By way of example, in some embodiments, one or more electrodes described herein comprises and/or is formed from a metal. Non-limiting examples of suitable metals include nickel, gold, aluminum, titanium, and platinum.

As described elsewhere herein, in some embodiments, a passivation layer is disposed on at least a portion of an electrode surface. When present, a passivation layer may have a variety of suitable thicknesses. In some embodiments, a passivation layer disposed on an electrode has a thickness of greater than or equal to 300 nm, greater than or equal to 325 nm, greater than or equal to 350 nm, greater than or equal to 375 nm, greater than or equal to 400 nm, greater than or equal to 425 nm, greater than or equal to 450 nm, greater than or equal to 475 nm, greater than or equal to 500 nm, greater than or equal to 525 nm, greater than or equal to 550 nm, or greater than or equal to 575 nm. In some embodiments, a passivation layer disposed on an electrode has a thickness of less than or equal to 600 nm, less than or equal to 575 nm, less than or equal to 550 nm, less than or equal to 525 nm, less than or equal to 500 nm, less than or equal to 475 nm, less than or equal to 450 nm, less than or equal to 425 nm, less than or equal to 400 nm, less than or equal to 375 nm, less than or equal to 350 nm, or less than or equal to 325 nm. Combinations of the above-referenced ranges are also possible (e.g., greater than or equal to 300 nm and less than or equal to 600 nm). Other ranges are also possible. The thickness of the passivation layer may be determined by ellipsometry.

The passivation layers described herein may comprise and/or be formed from a variety of suitable materials. By way of example, in some embodiments, a passivation layer disposed on an electrode comprises and/or is formed from a polymer and/or a ceramic. Non-limiting examples of suitable such materials include photoresists (e.g., an AZ series photoresist, an S1800 series photoresist, an SU8 photoresist, a Futurrex photoresist, a polyimide photoresist, a polyimide-based photoresist), nitrides (e.g., silicon nitride), oxides (e.g., silicon oxide), and silicates (e.g., tetraethyl orthosilicate).

As also described elsewhere herein, in some embodiments, a wire bonding composition is disposed on at least a portion of an electrode surface. The wire bonding composition may facilitate bonding of the electrode with one or more wires (e.g., wire(s) placing the electrode in electrical communication with an environment external to the sensor). Suitable wire bonding compositions may comprise and/or be formed from a metal, such as titanium and/or gold.

As described elsewhere herein, some sensors may comprise further electrodes in addition to one or more pairs of electrodes. In some embodiments, one or more of the pair(s) of electrodes in a sensor are configured to sense an analyte of interest and one or more further pairs of electrodes are also included in the sensor to provide a function other than sensing the analyte. Such electrodes are described in further detail below.

In some embodiments, a sensor comprises a water gate electrode. The water gate electrode may assist with regulation of the potential of the fluid to which the one or more of the pairs of electrodes are exposed. Advantageously, the water gate electrode may place the fluid at a potential that facilitates an interaction of the fluid with the pair(s) of electrodes that enhances the sensitivity of the sensor to one or more analytes therein. By way of example, the water gate electrode may place the fluid at a potential that enhances its charge sensitivity. In some embodiments, the water gate electrode's utility is enhanced when the water gate electrode is in direct contact with the fluid comprising the analyte(s) to be detected. Accordingly, in some embodiments, a water gate electrode is configured to directly contact a fluid to be analyzed by the sensor and/or directly contacts a fluid to be analyzed by the sensor at one or more points in time (e.g., during use of the sensor).

When present, the water gate electrode may have a variety of suitable designs. In some embodiments, the water gate electrode is circular and/or has a circular cross-section (e.g., it may be cylindrical). The water gate electrode may have a variety of suitable thicknesses. In some embodiments, the water gate electrode has a thickness of greater than or equal to 100 microns, greater than or equal to 150 microns, greater than or equal to 200 microns, greater than or equal to 250 microns, greater than or equal to 300 microns, greater than or equal to 350 microns, greater than or equal to 400 microns, or greater than or equal to 450 microns. In some embodiments, the water gate electrode has a thickness of less than or equal to 500 microns, less than or equal to 450 microns, less than or equal to 400 microns, less than or equal to 350 microns, less than or equal to 300 microns, less than or equal to 250 microns, less than or equal to 200 microns, or less than or equal to 150 microns. Combinations of the above-referenced ranges are also possible (e.g., greater than or equal to 100 microns and less than or equal to 500 microns). Other ranges are also possible.

It should also be understood that the values listed above may independently describe the average thickness of a water gate electrode or the median thickness of the water gate electrode.

A variety of suitable compositions may be employed to form water gate electrodes. In some embodiments, a water gate electrode comprises and/or is formed from a composition comprising silver, gold, and/or platinum. For instance, a water gate electrode may comprise and/or be formed from silver and/or silver chloride. In some embodiments, a water gate electrode is formed by applying an epoxy ink and/or paste comprising silver and silver chloride directly onto a plasma-etched substrate. As another example, an epoxy ink and/or paste comprising silver and silver chloride may be applied to an electrode comprising gold to facilitate electrical communication with a wire bonding pad.

In some embodiments, a sensor comprises a ground electrode. The ground electrode may be configured to electrically ground a fluid to which the sensor is exposed. This may be advantageous in sensors in which it is possible that the fluid may overcharge. The ground electrode may be in electrical communication with a ground wire. In some embodiments, the ground electrode is also configured to be in electrical communication with a fluid to be analyzed by the sensor under certain conditions (e.g., when the fluid is overcharged). This may be accomplished by placing the fluid in direct contact with the ground electrode.

A variety of suitable compositions may be employed to form ground electrodes. In some embodiments, a ground electrode comprises and/or is formed from a metal. For instance, a water gate electrode may comprise and/or be formed from gold and/or platinum.

In some embodiments, a sensor comprises a back gate electrode. The back gate electrode may be configured to provide a solid state gating of a nanowire placing a pair of electrodes in electrical communication. Varying the potential of the back gate electrode may, e.g., vary the conductivity of the nanowire. Advantageously, this may allow the sensitivity of the sensor to the analyte to be varied.

A variety of suitable compositions may be employed to form back gate electrodes. In some embodiments, a back gate electrode comprises and/or is formed from a metal or a semiconductor. For instance, a water gate electrode may comprise and/or be formed from gold and/or silicon (e.g., doped silicon).

As also described elsewhere herein, in some embodiments, a sensor comprises an electrically insulating layer. The electrically insulating layer may isolate one or more portions of the sensor from direct contact with an environment external thereto (e.g., it may electrically isolate one or more portions of an electrode surface from a fluid to which the sensor is exposed).

When present, an electrically insulating layer may have a variety of suitable thicknesses. In some embodiments, an electrically insulating layer has a thickness of greater than or equal to 0.1 micron, greater than or equal to 0.2 microns, greater than or equal to 0.5 microns, greater than or equal to 0.75 microns, greater than or equal to 1 micron, greater than or equal to 1.1 microns, greater than or equal to 1.2 microns, greater than or equal to 1.3 microns, greater than or equal to 1.4 microns, greater than or equal to 1.5 microns, greater than or equal to 1.6 microns, greater than or equal to 1.7 microns, greater than or equal to 1.8 microns, greater than or equal to 1.9 microns, greater than or equal to 2 microns, greater than or equal to 2.1 microns, greater than or equal to 2.2 microns, greater than or equal to 2.5 microns, greater than or equal to 2.75 microns, greater than or equal to 3 microns, greater than or equal to 5 microns, greater than or equal to 10 microns, greater than or equal to 20 microns, greater than or equal to 50 microns, greater than or equal to 75 microns, greater than or equal to 100 microns, greater than or equal to 200 microns, greater than or equal to 500 microns, greater than or equal to 750 microns, or greater than or equal to 1,000 microns. In some embodiments, an electrically insulating layer has a thickness of less than or equal to 2,000 microns, less than or equal to 1,000 microns, less than or equal to 750 microns, less than or equal to 500 microns, less than or equal to 200 microns, less than or equal to 100 microns, less than or equal to 75 microns, less than or equal to 50 microns, less than or equal to 20 microns, less than or equal to 10 microns, less than or equal to 5 microns, less than or equal to 3 microns, less than or equal to 2.75 microns, less than or equal to 2.5 microns, less than or equal to 2.2 microns, less than or equal to 2.1 microns, less than or equal to 2 microns, less than or equal to 1.9 microns, less than or equal to 1.8 microns, less than or equal to 1.7 microns, less than or equal to 1.6 microns, less than or equal to 1.5 microns, less than or equal to 1.4 microns, less than or equal to 1.3 microns, less than or equal to 1.2 microns, less than or equal to 1.1 microns, less than or equal to 1 micron, less than or equal to 0.75 microns, less than or equal to 0.5 microns, or less than or equal to 0.2 microns. Combinations of the above-referenced ranges are also possible (e.g., greater than or equal to 0.1 micron and less than or equal to 200 microns, greater than or equal to 0.2 microns and less than or equal to 200 microns, greater than or equal to 1 micron and less than or equal to 2 microns, or greater than or equal to 1.4 microns and less than or equal to 1.6 microns). Other ranges are also possible.

It should also be understood that the values listed above may independently describe the average thickness of an electrically insulating layer or the median height of the electrically insulating layer.

In some embodiments, an electrically insulating layer is positioned such that the leakage current between a pair of electrodes and/or between an electrode in a pair of electrodes and a reference electrode (e.g., a water gate electrode) is less than $3*10^{-11}$ A.

Electrically insulating layers may, when present, comprise a photoresist (e.g., an AZ series photoresist, an S1800 series photoresist, an SU8 photoresist, a Futurrex photoresist). The photoresists suitable for use in forming an electrically insulating layer may also be suitable for performing the photolithographic processes described elsewhere herein (e.g., those used to form electrodes, passivating layers, wire bonding compositions, etc. at desired positions). It is also possible for some photoresists suitable for use in an electrically insulating layer and/or for photolithography to be biocompatible (e.g., in some embodiments, antibodies, such as IgG, exposed thereto do not undergo excessive denaturation as determined by ELISA) and/or chemically inert (e.g., in some embodiments, a photoresist does not undergo appreciable changes in hydrophobicity as determined by a water contact angle measurement, diffraction of light, and/or thickness during further sensor fabrication steps and/or upon exposure to a fluid to be analyzed by the sensor). Advantageously, a suitable photoresist may be readily adherent to one or more other components of the sensor (e.g., a surface layer, a an electrode, a passivating layer) in the absence of an adhesion promoter (e.g., in the absence of hexamethyldisilane). Suitable adhesion may be adhesion such that the photoresist does not delaminate from the relevant component(s) during fabrication and/or use of the sensor.

As described above, in some embodiments, a sensor comprises a substrate. One or more other components of the sensor may be disposed thereon. Non-limiting examples of suitable substrates include substrates comprising silicon, silicon oxide, glass, quartz, and/or sapphire. In some embodiments, the substrate may be a wafer comprising and/or formed from one or more of the above-referenced materials. The substrate may have a resistivity that is relatively low. For instance, in some embodiments, a sensor is disposed on a substrate having a resistivity of less than 0.005 ohm-cm.

As also described above, in some embodiments, a surface layer may be disposed on a substrate. The surface layer may allow for the formation of fiducial alignment marks by etching away a portion thereof and/or may provide a suitable surface for the formation of further sensor components thereon.

The surface layers described herein may have a variety of suitable thicknesses. In some embodiments, a surface layer has a thickness of greater than or equal to 50 nm, greater than or equal to 75 nm, greater than or equal to 100 nm, greater than or equal to 150 nm, greater than or equal to 200 nm, greater than or equal to 250 nm, greater than or equal to 300 nm, greater than or equal to 350 nm, greater than or equal to 400 nm, greater than or equal to 500 nm, greater than or equal to 600 nm, greater than or equal to 700 nm, greater than or equal to 800 nm, greater than or equal to 900 nm, greater than or equal to 1 micron, greater than or equal to 1.25 microns, greater than or equal to 1.5 microns, or greater than or equal to 1.75 microns. In some embodiments, a surface layer has a thickness of less than or equal to 2 microns, less than or equal to 1.75 microns, less than or equal to 1.5 microns, less than or equal to 1.25 microns, less than or equal to 1 micron, less than or equal to 900 nm, less than or equal to 800 nm, less than or equal to 700 nm, less than or equal to 600 nm, less than or equal to 500 nm, less than or equal to 400 nm, less than or equal to 350 nm, less than or equal to 300 nm, less than or equal to 250 nm, less than or equal to 200 nm, less than or equal to 150 nm, less than or equal to 100 nm, or less than or equal to 75 nm. Combinations of the above-referenced ranges are also possible (e.g., greater than or equal to 50 nm and less than or equal to 2 microns, greater than or equal to 300 nm and less than or equal to 1 micron, or greater than or equal to 300 nm and less than or equal to 600 nm). Other ranges are also possible.

It should also be understood that the values listed above may independently describe the average thickness of a surface layer or the median thickness of the surface layer.

The surface layers described herein may have a variety of suitable compositions. By way of example, one or more of the following types of layers disposed on a substrate: a layer comprising an oxide (e.g., a layer comprising silicon dioxide, such as a layer comprising silicon dioxide formed by a wet thermal process and/or a silicon dioxide layer formed by a dry thermal process; a layer comprising aluminum oxide; a layer comprising hafnium oxide; a layer comprising germanium oxide) and/or a layer comprising a nitride (e.g., a layer comprising silicon nitride).

As described elsewhere herein, in some embodiments, a plurality of nanowires are deposited onto a substrate from a fluid. Further details of this process are described below.

Nanowires may be deposited from a variety of suitable fluids. In general, it may be advantageous for the components of the fluid other than the nanowires to be relatively non-toxic. It may also be advantageous for components of the fluid designed not to be incorporated into the sensor (e.g., components other than the nanowires and/or components to be included with the nanowires) to be relatively volatile at the temperature at which the nanowires are deposited therefrom. In some embodiments, a fluid comprises a liquid, such as an organic solvent and/or water. The organic solvent may be an alcohol (e.g., ethanol, isopropanol) and/or an alkane (e.g., hexane). In some embodiments, the fluid further comprises a surfactant, such as a non-ionic surfactant (e.g., Tween 20). One example of a suitable fluid is a fluid comprising 1 wt %/vol Tween 20 in deionized water.

Suitable liquids for depositing nanowires may have a relatively low boiling point. In some embodiments, the liquid has a boiling point of less than or equal to 120° C., less than or equal to 115° C., less than or equal to 110° C., less than or equal to 105° C., less than or equal to 100° C., less than or equal to 95° C., less than or equal to 90° C., less than or equal to 85° C., less than or equal to 80° C., less than or equal to 75° C., less than or equal to 70° C., less than or equal to 65° C., less than or equal to 60° C., or less than or equal to 55° C. In some embodiments, the liquid has a boiling point of greater than or equal to 50° C., greater than or equal to 55° C., greater than or equal to 60° C., greater than or equal to 65° C., greater than or equal to 70° C., greater than or equal to 75° C., greater than or equal to 80° C., greater than or equal to 85° C., greater than or equal to 90° C., greater than or equal to 95° C., greater than or equal to 100° C., greater than or equal to 105° C., greater than or equal to 110° C., or greater than or equal to 115° C. Combinations of the above-referenced ranges are also possible (e.g., less than or equal to 120° C. and greater than or equal to 50° C., or less than or equal to 80° C. and greater than or equal to 50° C.). Other ranges are also possible. The boiling point of a liquid may be determined by distillation.

In some embodiments, a liquid from which nanowires are deposited has an advantageous value of specific gravity. For instance, the specific gravity may be greater than or equal to 0.7 $g/cm^3$, greater than or equal to 0.75 $g/cm^3$, greater than or equal to 0.8 $g/cm^3$, greater than or equal to 0.85 $g/cm^3$, greater than or equal to 0.9 $g/cm^3$, greater than or equal to 0.95 $g/cm^3$, greater than or equal to 1 $g/cm^3$, or greater than or equal to 1.05 $g/cm^3$. In some embodiments, the specific gravity is less than or equal to 1.1 $g/cm^3$, less than or equal to 1.05 $g/cm^3$, less than or equal to 1 $g/cm^3$, less than or equal to 0.95 $g/cm^3$, less than or equal to 0.9 $g/cm^3$, less than or equal to 0.85 $g/cm^3$, less than or equal to 0.8 $g/cm^3$, or less than or equal to 0.75 $g/cm^3$. Combinations of the above-referenced ranges are also possible (e.g., greater than or equal to 0.75 $g/cm^3$ and less than or equal to 1.1 $g/cm^3$). Other ranges are also possible.

When a plurality of nanowires is deposited onto a substrate from a fluid, the nanowires may be present in the fluid in a variety of suitable manners. By way of example, the nanowires may be suspended in the fluid and/or may, together with the other components of the fluid (e.g., together with any water, organic solvents, and/or surfactants therein), form a colloid. The concentration of the nanowires in the fluid may generally be selected as desired. In some embodiments, a fluid comprises nanowires at a concentration such that the nanowires have an absorbance at 420 nm of greater than or equal to 0.45, greater than or equal to 0.46, greater than or equal to 0.47, greater than or equal to 0.48, greater than or equal to 0.49, greater than or equal to 0.5, greater than or equal to 0.51, greater than or equal to 0.52, greater than or equal to 0.53, or greater than or equal to 0.54. In some embodiments, a fluid comprises nanowires at a concentration such that the nanowires have an absorbance at 420 nm of less than or equal to 0.55, less than or equal to 0.54, less than or equal to 0.53, less than or equal to 0.52, less than or equal to 0.51, less than or equal to 0.5, less than or equal to 0.49, less than or equal to 0.48, less than or equal to 0.47, or less than or equal to 0.46. Combinations of the above-referenced ranges are also possible (e.g., greater than or equal to 0.45 and less than or equal to 0.55). Other ranges are also possible. The absorbance of the nanowires in the fluid may be determined with the use of a spectrophotometer.

Prior to depositing the fluid on a substrate, the fluid may undergo one or more processes to enhance the uniformity with which the nanowires are dispersed therein and/or to break up any clumps and/or aggregates of nanowires therein. This may be accomplished by, for instance, sonicating the fluid. The fluid may be sonicated for a variety of suitable amounts of time. In some embodiments, a fluid comprising nanowires is sonicated for greater than or equal to 1.5 minutes, greater than or equal to 1.75 minutes, greater than or equal to 2 minutes, greater than or equal to 2.25 minutes, greater than or equal to 2.5 minutes, greater than or equal to 2.75 minutes, greater than or equal to 3 minutes, greater than or equal to 3.5 minutes, greater than or equal to 4 minutes, or greater than or equal to 4.5 minutes. In some embodiments, a fluid comprising nanowires is sonicated for less than or equal to 5 minutes, less than or equal to 4.5 minutes, less than or equal to 4 minutes, less than or equal to 3.5 minutes, less than or equal to 3 minutes, less than or equal to 2.75 minutes, less than or equal to 2.5 minutes, less than or equal to 2.25 minutes, less than or equal to 2 minutes, or less than or equal to 1.75 minutes. Combinations of the above-referenced ranges are also possible (e.g., greater than or equal to 1.5 minutes and less than or equal to 5 minutes). Other ranges are also possible.

A fluid comprising nanowires may deposit nanowires therefrom from a quantity of fluid having a variety of suitable initial volumes. In some embodiments, the quantity of fluid has an initial volume of greater than or equal to 0.05 microliters, greater than or equal to 0.075 microliters, greater than or equal to 0.1 microliter, greater than or equal to 0.125 microliters, greater than or equal to 0.15 microliters, greater than or equal to 0.175 microliters, greater than or equal to 0.2 microliters, greater than or equal to 0.225 microliters, greater than or equal to 0.25 microliters, greater than or equal to 0.275 microliters, greater than or equal to 0.3 microliters, greater than or equal to 0.35 microliters, greater than or equal to 0.4 microliters, greater than or equal to 0.5 microliters, greater than or equal to 0.6 microliters, or greater than or equal to 0.8 microliters. In some embodiments, the quantity of fluid has an initial volume of less than or equal to 1 microliter, less than or equal to 0.8 microliters, less than or equal to 0.6 microliters, less than or equal to 0.5 microliters, less than or equal to 0.4 microliters, less than or equal to 0.35 microliters, less than or equal to 0.3 microliters, less than or equal to 0.275 microliters, less than or equal to 0.25 microliters, less than or equal to 0.225 microliters, less than or equal to 0.2 microliters, less than or equal to 0.175 microliters, less than or equal to 0.15 microliters, less than or equal to 0.125 microliters, less than or equal to 0.1 microliter, or less than or equal to 0.075 microliters. Combinations of the above-referenced ranges are also possible (e.g., greater than or equal to 0.05 microliters and less than or equal to 1 microliter, greater than or equal to 0.1 microliter and less than or equal to 1 microliter, greater than or equal to 0.1 microliter and less than or equal to 0.3 microliters, or greater than or equal to 0.2 microliters and less than or equal to 0.25 microliters). Other ranges are also possible.

As described elsewhere herein, a method may comprise expelling a fluid comprising a plurality of nanowires onto a substrate to form a quantity of the fluid disposed on the substrate, allowing at least a portion of the fluid to evaporate, and replenishing at least a portion of the evaporated fluid. As used herein, the initial volume of the quantity of fluid is the maximum volume of the quantity of fluid prior to any replenishment of fluid evaporated therefrom. In other words, it is the volume of the quantity of fluid after it has been fully formed by expulsion of the fluid onto the substrate and prior to any evaporation thereafter.

When a fluid comprising nanowires is allowed to evaporate from a surface, it may do so over a variety of suitable amounts of time. In some embodiments, a fluid comprising nanowires is allowed to evaporate from a surface over a period of time of greater than or equal to 0.05 seconds, greater than or equal to 0.075 seconds, greater than or equal to 0.1 second, greater than or equal to 0.125 seconds, greater than or equal to 0.15 seconds, greater than or equal to 0.175 seconds, greater than or equal to 0.2 seconds, greater than or equal to 0.225 seconds, greater than or equal to 0.25 seconds, greater than or equal to 0.275 seconds, greater than or equal to 0.3 seconds, greater than or equal to 0.325 seconds, greater than or equal to 0.35 seconds, greater than or equal to 0.375 seconds, greater than or equal to 0.4 seconds, greater than or equal to 0.45 seconds, greater than or equal to 0.5 seconds, greater than or equal to 0.55 seconds, greater than or equal to 0.6 seconds, greater than or equal to 0.8 seconds, greater than or equal to 1 second, greater than or equal to 1.5 seconds, greater than or equal to 2 seconds, greater than or equal to 2.5 seconds, greater than or equal to 3 seconds, or greater than or equal to 4 seconds. In some embodiments, a fluid comprising nanowires is allowed to evaporate from a surface over a period of time of less than or equal to 5 seconds, less than or equal to 4 seconds, less than or equal to 3 seconds, less than or equal to 2.5 seconds, less than or equal to 2 seconds, less than or equal to 1.5 seconds, less than or equal to 1 second, less than or equal to 0.8 seconds, less than or equal to 0.6 seconds, less than or equal to 0.55 seconds, less than or equal to 0.5 seconds, less than or equal to 0.45 seconds, less than or equal to 0.4 seconds, less than or equal to 0.375 seconds, less than or equal to 0.35 seconds, less than or equal to 0.325 seconds, less than or equal to 0.3 seconds, less than or equal to 0.275 seconds, less than or equal to 0.25 seconds, less than or equal to 0.225 seconds, less than or equal to 0.2 seconds, less than or equal to 0.175 seconds, less than or equal to 0.15 seconds, less than or equal to 0.125 seconds, less than or equal to 0.1 second, or less than or equal to 0.075 seconds. Combinations of the above-referenced ranges are also possible (e.g., greater than or equal to 0.05 seconds and less than or equal to 5 seconds, greater than or equal to 0.1 second and less than or equal to 0.5 seconds, or greater than or equal to 0.2 seconds and less than or equal to 0.3 seconds). Other ranges are also possible.

When evaporating from a substrate, the contact angle of a fluid comprising a plurality of nanowires may have a variety of suitable values. In some embodiments, the fluid has a contact angle of greater than or equal to 20°, greater than or equal to 25°, greater than or equal to 30°, greater than or equal to 35°, greater than or equal to 40°, greater than or equal to 45°, greater than or equal to 50°, greater than or equal to 55°, greater than or equal to 60°, greater than or equal to 65°, greater than or equal to 70°, greater than or equal to 75°, greater than or equal to 80°, or greater than or equal to 85°. In some embodiments, the fluid has a contact angle of less than or equal to 90°, less than or equal to 85°, less than or equal to 80°, less than or equal to 75°, less than or equal to 70°, less than or equal to 65°, less than or equal to 60°, less than or equal to 55°, less than or equal to 50°, less than or equal to 45°, less than or equal to 40°, less than or equal to 35°, less than or equal to 30°, or less than or equal to 25°. Combinations of the above-referenced ranges are also possible (e.g., greater than or equal to 20° and less than or equal to 90°). Other ranges are also possible. The contact angle may be measured using a goniometer.

It should be understood that the contact angle of a fluid comprising nanowires may vary as it evaporates. Accordingly, it should be understood that a fluid comprising nanowires may independently have a contact angle in one or more of the above ranges at different points in time during evaporation and/or may have contact angles in two or more different ranges at different points in time during evaporation. By way of the example, an evaporating fluid may have an initial contact angle in one or more of the above-referenced ranges (e.g., a contact angle at the point in time described above with respect to initial volume), a contact angle at one or more points in time during evaporation in one or more of the above-referenced ranges, a contact angle at one or more points in time during replenishment in one or more of the above-referenced ranges, and/or an average contact angle during evaporation and replenishment in one or more of the above-referenced ranges.

As also described elsewhere herein, a fluid comprising nanowires may be deposited onto a substrate from a nozzle. The nozzle may be positioned at a variety of suitable distances from the substrate during evaporation and/or replenishment of the fluid. In some embodiments, the nozzle is positioned at a distance of greater than or equal to 0.01 mm, greater than or equal to 0.015 mm, greater than or equal to 0.02 mm, greater than or equal to 0.025 mm, greater than or equal to 0.03 mm, greater than or equal to 0.035 mm, greater than or equal to 0.04 mm, greater than or equal to 0.045 mm, greater than or equal to 0.0475 mm, greater than or equal to 0.05 mm, greater than or equal to 0.0525 mm, greater than or equal to 0.055 mm, greater than or equal to 0.0575 mm, greater than or equal to 0.06 mm, greater than or equal to 0.0625 mm, greater than or equal to 0.065 mm, greater than or equal to 0.07 mm, greater than or equal to 0.08 mm, greater than or equal to 0.09 mm, greater than or equal to 0.1 mm, greater than or equal to 0.125 mm, greater than or equal to 0.15 mm, greater than or equal to 0.175 mm, greater than or equal to 0.2 mm, or greater than or equal to 0.25 mm from the substrate. In some embodiments, the nozzle is positioned at a distance of less than or equal to 0.3 mm, less than or equal to 0.25 mm, less than or equal to 0.2 mm, less than or equal to 0.175 mm, less than or equal to 0.15 mm, less than or equal to 0.125 mm, less than or equal to 0.1 mm, less than or equal to 0.09 mm, less than or equal to 0.08 mm, less than or equal to 0.07 mm, less than or equal to 0.065 mm, less than or equal to 0.0625 mm, less than or equal to 0.06 mm, less than or equal to 0.0575 mm, less than or equal to 0.055 mm, less than or equal to 0.0525 mm, less than or equal to 0.05 mm, less than or equal to 0.0475 mm, less than or equal to 0.045 mm, less than or equal to 0.04 mm, less than or equal to 0.035 mm, less than or equal to 0.03 mm, less than or equal to 0.025 mm, less than or equal to 0.02 mm, or less than or equal to 0.015 mm from the substrate. Combinations of the above-referenced ranges are also possible (e.g., greater than or equal to 0.01 mm and less than or equal to 0.3 mm, greater than or equal to 0.01 mm and less than or equal to 0.2 mm, greater than or equal to 0.03 mm and less than or equal to 0.1 mm, or greater than or equal to 0.05 mm and less than or equal to 0.06 mm). Other ranges are also possible.

When a fluid is deposited onto a substrate, the substrate may be held at a variety of suitable temperatures. In some embodiments, the substrate is held at a temperature that facilitates evaporation of the fluid (e.g., the substrate may be heated). The temperature of the substrate may be greater than or equal to 55° C., greater than or equal to 56° C., greater than or equal to 57° C., greater than or equal to 58° C., greater than or equal to 59° C., greater than or equal to 60° C., greater than or equal to 61° C., greater than or equal to 62° C., greater than or equal to 63° C., greater than or equal to 64° C., greater than or equal to 65° C., greater than or equal to 66° C., greater than or equal to 67° C., greater than or equal to 68° C., greater than or equal to 69° C., greater than or equal to 70° C., greater than or equal to 71° C., greater than or equal to 72° C., greater than or equal to 73° C., greater than or equal to 74° C., greater than or equal to 75° C., greater than or equal to 76° C., greater than or equal to 77° C., greater than or equal to 78° C., or greater than or equal to 79° C. The temperature of the substrate may be less than or equal to 80° C., less than or equal to 79° C., less than or equal to 78° C., less than or equal to 77° C., less than or equal to 76° C., less than or equal to 75° C., less than or equal to 74° C., less than or equal to 73° C., less than or equal to 72° C., less than or equal to 71° C., less than or equal to 70° C., less than or equal to 69° C., less than or equal to 68° C., less than or equal to 67° C., less than or equal to 66° C., less than or equal to 65° C., less than or equal to 64° C., less than or equal to 63° C., less than or equal to 62° C., less than or equal to 61° C., less than or equal to 60° C., less than or equal to 59° C., less than or equal to 58° C., less than or equal to 57° C., or less than or equal to 56° C. Combinations of the above-referenced ranges are also possible (e.g., greater than or equal to 55° C. and less than or equal to 80° C., greater than or equal to 60° C. and less than or equal to 70° C., or greater than or equal to 64° C. and less than or equal to 66° C.). Other ranges are also possible. The temperature of the substrate may be determined by a thermocouple positioned on the surface of the substrate on which the fluid is deposited.

As described elsewhere herein, in some embodiments, a sensor being fabricated is heated during fabrication to assist with the formation of ohmic contacts between the electrodes and the nanowires therein. Further details of this process are described below.

Some embodiments may comprise exposing a sensor being fabricated to a temperature of greater than or equal to 380° C., greater than or equal to 382.5° C., greater than or equal to 385° C., greater than or equal to 387.5° C., greater than or equal to 390° C., greater than or equal to 392.5° C., greater than or equal to 395° C., greater than or equal to 397.5° C., greater than or equal to 400° C., or greater than or equal to 402.5° C. Some embodiments may comprise exposing a sensor being fabricated to a temperature of less than or equal to 405° C., less than or equal to 402.5° C., less than or equal to 400° C., less than or equal to 397.5° C., less than or equal to 395° C., less than or equal to 392.5° C., less than or equal to 390° C., less than or equal to 387.5° C., less than or equal to 385° C., or less than or equal to 382.5° C. Combinations of the above-referenced ranges are also possible (e.g., greater than or equal to 380° C. and less than or equal to 400° C., or greater than or equal to 395° C. and less than or equal to 405° C.). Other ranges are also possible. The sensor may be exposed to a temperature in one or more of the above-referenced ranges by, for instance, a furnace, a rapid thermal annealer, and/or an oven.

A sensor being fabricated may be exposed to an elevated temperature to a variety of suitable times. In some embodiments, a sensor is exposed to a temperature in one or more of the above-referenced ranges for a period of time of greater than or equal to 1 minute, greater than or equal to 1.2 minutes, greater than or equal to 1.4 minutes, greater than or equal to 1.6 minutes, greater than or equal to 1.7 minutes, greater than or equal to 1.8 minutes, greater than or equal to 1.9 minutes, greater than or equal to 2 minutes, greater than or equal to 2.1 minutes, greater than or equal to 2.2 minutes, greater than or equal to 2.3 minutes, greater than or equal to 2.4 minutes, greater than or equal to 2.6 minutes, greater than or equal to 2.8 minutes, greater than or equal to 3 minutes, greater than or equal to 3.25 minutes, greater than or equal to 3.5 minutes, greater than or equal to 3.75 minutes, greater than or equal to 4 minutes, greater than or equal to 4.5 minutes, greater than or equal to 5 minutes, greater than or equal to 6 minutes, or greater than or equal to 8 minutes. In some embodiments, a sensor is exposed to a temperature in one or more of the above-referenced ranges for a period of time of less than or equal to 10 minutes, less than or equal to 8 minutes, less than or equal to 6 minutes, less than or equal to 5 minutes, less than or equal to 4.5 minutes, less than or equal to 4 minutes, less than or equal to 3.75 minutes, less than or equal to 3.5 minutes, less than or equal to 3.25 minutes, less than or equal to 3 minutes, less than or equal to 2.8 minutes, less than or equal to 2.6 minutes, less than or equal to 2.4 minutes, less than or equal to 2.3 minutes, less than or equal to 2.2 minutes, less than or equal to 2.1 minutes, less than or equal to 2 minutes, less than or equal to 1.9 minutes, less than or equal to 1.8 minutes, less than or equal to 1.7 minutes, less than or equal to 1.6 minutes, less than or equal to 1.4 minutes, or less than or equal to 1.2 minutes. Combinations of the above-referenced ranges are also possible (e.g., greater than or equal to 1 minute and less than or equal to 10 minutes, or greater than or equal to 1.9 minutes and less than or equal to 2.1 minutes). Other ranges are also possible.

It should be understood that the values in the preceding paragraph may refer to the amount of time that a sensor being fabricated is exposed to a single temperature in one or more of the preceding ranges and/or may refer to the amount of time that a sensor being fabricated is exposed to any temperature in one or more of the above-referenced ranges (e.g., the total amount of time that the sensor is exposed to any temperature of greater than or equal to 380° C. and less than or equal to 400° C.).

When a sensor being fabricated is exposed to an elevated temperature, it may also be exposed to an ambient environment that assists with the formation of ohmic contacts between the electrode material therein and the nanowires therein. By way of example, the sensor may be simultaneously exposed to an elevated temperature and a forming gas. The forming gas may comprise and/or consist of a mixture of hydrogen and nitrogen. Hydrogen may make up greater than or equal to 1 wt %, greater than or equal to 2 wt %, greater than or equal to 3 wt %, greater than or equal to 4 wt %, greater than or equal to 5 wt %, greater than or equal to 6 wt %, greater than or equal to 7 wt %, greater than or equal to 8 wt %, or greater than or equal to 9 wt % of the mixture. Hydrogen may make up less than or equal to 10 wt %, less than or equal to 9 wt %, less than or equal to 8 wt %, less than or equal to 7 wt %, less than or equal to 6 wt %, less than or equal to 5 wt %, less than or equal to 4 wt %, less than or equal to 3 wt %, or less than or equal to 2 wt % of the mixture. Combinations of the above-referenced ranges are also possible (e.g., greater than or equal to 1 wt % and less than or equal to 10 wt % hydrogen). Other ranges are also possible.

The presence of ohmic contacts may be determined by generating an IV curve according to the technique for generating an IV curve described above with respect to the on/off ratio. If the IV curve is linear and/or substantially linear, then ohmic contacts are considered to have been formed.

In some embodiments, a sensor as a whole may be configured to sense one or more analytes of interest in a particularly desirable manner. For instance, a sensor may respond to a relatively low level of analyte in a manner that is reproducible, predictable, and/or observable. In some embodiments, the concentration of an analyte in a fluid may be determined by the magnitude of a change in equivalent surface potential of a nanowire placing a pair of electrodes in electrical communication. The change in equivalent surface potential of the nanowire may be determined by a measuring a change in the current across the pair of electrodes and then dividing the measured change in current by the transconductance of the nanowire. The change in current across the pair of electrodes may be measured at a known applied voltage and with the use of a picoammeter. The transconductance of the nanowire may be determined by: (1) concurrently applying a 0.1 V potential across the pair of electrodes and varying the potential applied to a water gate electrode between −0.5 V and 0.5 V; and (2) plotting the measured current across the pair of electrodes as a function of the potential applied to the water gate electrode; and (3) identifying the maximum slope in this plot as the transconductance of the nanowire.

In some embodiments, a sensor exhibits a change in equivalent surface potential upon exposure to an analyte having an absolute value of greater than or equal to 0.005 V, greater than or equal to 0.006 V, greater than or equal to 0.007 V, greater than or equal to 0.008 V, greater than or equal to 0.009 V, greater than or equal to 0.01 V, greater than or equal to 0.015 V, greater than or equal to 0.02 V, greater than or equal to 0.025 V, greater than or equal to 0.03 V, greater than or equal to 0.04 V, greater than or equal to 0.05 V, greater than or equal to 0.06 V, or greater than or equal to 0.08 V. In some embodiments, a sensor exhibits a change in equivalent surface potential upon exposure to an analyte having an absolute value of less than or equal to 0.1 V, less than or equal to 0.08 V, less than or equal to 0.06 V, less than or equal to 0.05 V, less than or equal to 0.04 V, less than or equal to 0.03 V, less than or equal to 0.025 V, less than or equal to 0.02 V, less than or equal to 0.015 V, less than or equal to 0.01 V, less than or equal to 0.009 V, less than or equal to 0.008 V, less than or equal to 0.007 V, or less than or equal to 0.006 V. Combinations of the above-referenced ranges are also possible (e.g., greater than or equal to 0.005 V and less than or equal to 0.1 V). It should be understood that the ranges above may refer to positive changes in equivalent surface potential or negative changes in equivalent surface potential. Accordingly, further examples of suitable ranges include, for example, greater than or equal to −0.005 V and less than or equal to 0.005 V, greater than or equal to −0.01 V and less than or equal to 0.01 V, or greater than or equal to −0.1 V and less than or equal to 0.1 V. Other ranges are also possible.

As described elsewhere herein, the sensors described herein may be suitable for sensing a variety of analytes in a variety of fluids. In some embodiments, the fluid is a bodily fluid and/or comprises a bodily fluid. For instance, the fluid may comprise a bodily fluid (e.g., a solid bodily fluid, a viscous bodily fluid) that is resuspended in another fluid (e.g., a viral transport media, a buffered salt solution). The sensor may be suitable for sensing an analyte in a human bodily fluid of a human and/or in a non-human, animal bodily fluid. Non-limiting types of suitable bodily fluids include types of blood (e.g., venous whole blood, capillary whole blood), components of blood (e.g., plasma, serum), urine, saliva, tears, cerebro-spinal fluid, nasal secretions, and/or nasopharyngeal secretions. The bodily fluid may be obtained by, e.g., a finger stick. It is also possible for a bodily fluid to be obtained by collection using a swab.

In some embodiments, a sensor described herein may sense an analyte in a fluid via an electrostatic interaction. By way of example, a charged analyte may experience electrostatic attraction to a nanowire and/or a blocking layer disposed thereon. This electrostatic attraction may cause the analyte to deposit on the nanowire and/or blocking layer. In some embodiments, the analyte is a charged molecule, such as a charged biological polymer and/or a charged biological small molecule. Non-limiting examples of suitable analytes (e.g., charged analytes) include proteins (e.g., GFAP, UCH-L1, S100β, ICH, NFL-1), peptides, nucleic acids (e.g., DNA, RNA, PNA), lipids, carbohydrates, small molecules, and derivatives of the foregoing.

The sensors described herein may be suitable for detecting one or more characteristics of a patient based on the presence or absence of one or more analytes in a fluid obtained from the patient. Some methods may comprise employing the sensors described herein for this purpose. By way of example, a method may comprise exposing a sensor to a fluid. The sensor may then undergo a detectable change in one or more properties (e.g., equivalent surface potential), which may be indicative of one or more properties of the fluid (e.g., of the concentration and/or presence of an analyte therein). In some embodiments, the sensor may output a signal indicative of one or more properties of the fluid (e.g., it may output a detectable change in equivalent surface potential that is indicative of the concentration and/or presence of an analyte, such as a protein, in the fluid).

One example of a characteristic of a patient that may be detected is whether or not the patient has experienced traumatic brain injury (TBI). Without wishing to be bound by any particular theory, it is believed that TBI is a non-degenerative, non-congenital insult to the brain from an external mechanical force, which may possibly lead to permanent or temporary impairment of cognitive, physical, and/or psychosocial functions. It is also believed that TBI may cause a diminished or altered state of consciousness. A closed brain injury such as TBI may be caused by a rapid acceleration or deceleration in forward, backward, and/or rotational movement of the brain inside the skull that results in bruising and/or tearing of brain tissue and/or blood vessels. It is believed that the most common cause of closed brain injuries are car accidents, falls, and sports related injuries. It is also believed that a brain injury can also be inflicted by oneself or another (e.g., in the case of shaken baby syndrome). Early diagnosis of traumatic brain injury is believed to facilitate the early verification that no intracranial bleeding has occurred as a result of the injury. Patients who experience significant trauma to the head may be at risk of bleeding in or around the brain (e.g., of having an intracranial hemorrhage, IH). For instance, this may be a concern in patients who present to the Emergency Department (ED) after an accident, assault, or fall.

When the sensors described herein are employed to sense whether or not a patient has TBI, they may be configured to sense one or more biomarkers for TBI in a bodily fluid from the patient (e.g., in serum from the patient). Without wishing to be bound by any particular theory, it is believed that these include GFAP, UCH-L1, S100β, ICH, and NFL-1.

Example 1

This Example describes an exemplary process for forming an electrically insulating layer disposed a pair of electrodes. It is noted that a similar process may also be employed to form other layers from a photoresist (e.g., a passivating layer, a layer formed during one fabrication step to appropriately position one or more components thereof but removed from the sensor during a subsequent fabrication step).

First, the substrate and components disposed thereon are prepared for photoresist deposition. This is accomplished by rinsing the substrate and components disposed thereon with solvents, and then drying the substrate. Next, the substrate and components disposed thereon are heated to remove any residual water.

After cleaning, the photoresist is applied to the substrate and components disposed thereon and prepared for patterning. SU-8 TF 6000.5 (a negative photoresist) is applied to the substrate such that it covers approximately 50% of its diameter, after which the substrate is spun to distribute the photoresist across its surface. Next, the substrate and components disposed thereon are soft baked, and then allowed to cool.

Then, portions of the photoresist are patterned by a photolithography process. First, the portions desired to be retained are exposed to light at a wavelength that will cause the photoresist to undergo a chemical reaction. After exposure, the substrate and components disposed thereon are baked. During this period of time, the image of the pattern of portions of the photoresist exposed to the light may become visible. Then, the substrate and components disposed thereon are removed from the hot plate and allowed to cool.

After patterning, the portions of the photoresist so patterned are removed from the substrate. The substrate and components disposed thereon are immersed in SU-8 developer, during which gentle agitation is applied (e.g., by use of an orbital shaker). Then, the wafer and components disposed thereon are removed from the SU-8 developer, and sprayed and washed with fresh SU-8 developer. After this step, the substrate and components disposed thereon are rinsed with a solvent and then dried.

Next, photoresist residue exposed to light during the patterning process but not removed by the subsequent development process is removed by an oxygen plasma etching process. The wafer and components disposed thereon are exposed to an oxygen plasma.

Finally, the substrate and components disposed thereon (including the photoresist not exposed to light and still positioned on the substrate) are hard baked. The hard bake time may be adjusted upwards or downwards if peeling of the photoresist is observed.

Example 2

This Example describes an exemplary process for disposing a wire bonding composition on a pair of electrodes. It is noted that a similar process may also be employed to form other components with the assistance of photolithography (e.g., electrodes, a passivating layer).

First, the photoresist is applied to the substrate and components disposed thereon and prepared for patterning.

AZ-5214E-IR (a positive photoresist) is applied to the substrate such that it covers approximately 50% of the its diameter, after which the substrate is spun to distribute the photoresist across its surface. Next, the substrate and components disposed thereon are soft baked, and then allowed to cool.

Then, portions of the photoresist are patterned by a photolithography process. First, the portions desired to be removed are exposed to light at a wavelength that will cause the photoresist to undergo a chemical reaction.

After patterning, the portions of the photoresist so patterned are removed from the substrate. The substrate and components disposed thereon are immersed in a mixture of AZ 400K developer and deionized water. The immersion time should be selected to allow for removal of the photoresist exposed to the light. After this step, the substrate and components disposed thereon are rinsed with deionized water and then dried. Finally, the substrate and components disposed thereon are dried.

Next, the portions of the electrodes exposed by the removal of the photoresist are prepared for deposition of the wire bonding composition. The passivation layer is removed from the electrode surface by dipping the substrate and components disposed thereon in a solution having a 6:1 ratio of hydrofluoric acid to ammonium fluoride for 10 to 20 seconds. After removal of the substrate and components disposed thereon from the solution, the substrate and components disposed thereon are rinsed with deionized water, dried, and then heated to remove any residual water. Then, the substrate and components disposed thereon are transferred to a vacuum chamber.

Once in the vacuum chamber, the wire bonding composition is deposited onto the exposed electrode surface. Electron beam vacuum deposition is performed to first deposit a titanium layer having at thickness of 10 nm±1 nm and a gold layer having a thickness of 250 nm±25 nm. Portions of the titanium and gold layers not disposed directly on the electrode are then removed by placing the substrate and components disposed thereon in an acetone bath for 1 to 3 hours, and then rinsing with acetone.

Example 3

This Example describes the use of sensors comprising a pair of electrodes in electrical communication by a nanowire.

Figure 20:
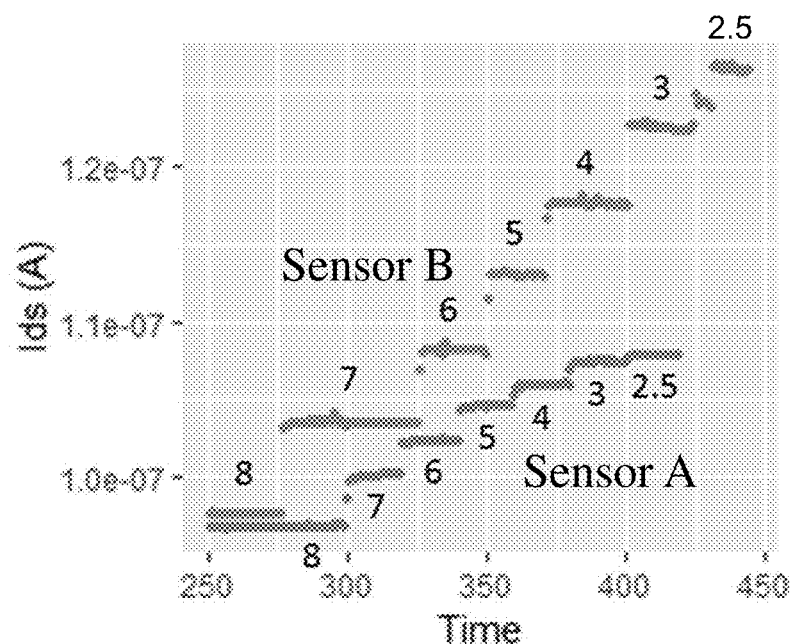
FIG. 20 is a plot showing current as a function of time, in accordance with some embodiments.
Figure 21:
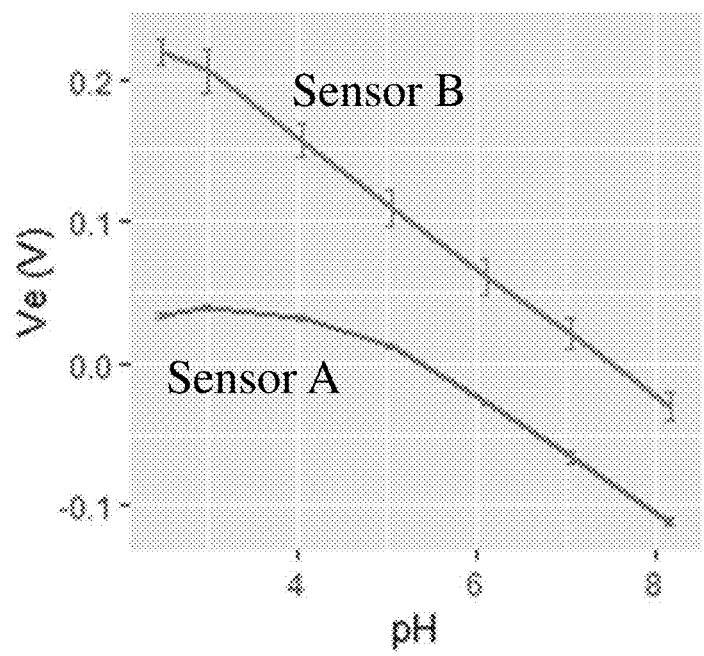
FIGS. 21-23 are plots showing equivalent surface potential as a function of time, in accordance with some embodiments.

Two sensors were formed: one sensor comprising silicon nanowires (Sensor A), and one sensor comprising silicon nanowires comprising (3-aminopropyl)triethoxysilane-functionalized surfaces (Sensor B). Each was exposed to a series of decreasing values of pH, during which the current across the pair of electrodes was measured. FIGS. 20-21 show the result of this experiment. From both FIGs. it is apparent that Sensor B displayed an increased sensitivity to changes in pH in comparison to Sensor A when the current through the nanowire was measured (as shown in FIG. 20) but that the two sensors showed similar variation in equivalent surface potential with pH (as shown in FIG. 21). It is believed that Sensor B exhibited a linear response to changes in pH over a wide range of pH values due to the presence of both —OH and —NH$_2$ groups on its surface, both of which can undergo protonation and deprotonation reactions as the pH is changed. It is believed that Sensor A exhibited a response to changes in pH similar to that of pure silicon oxide.

Figure 22:
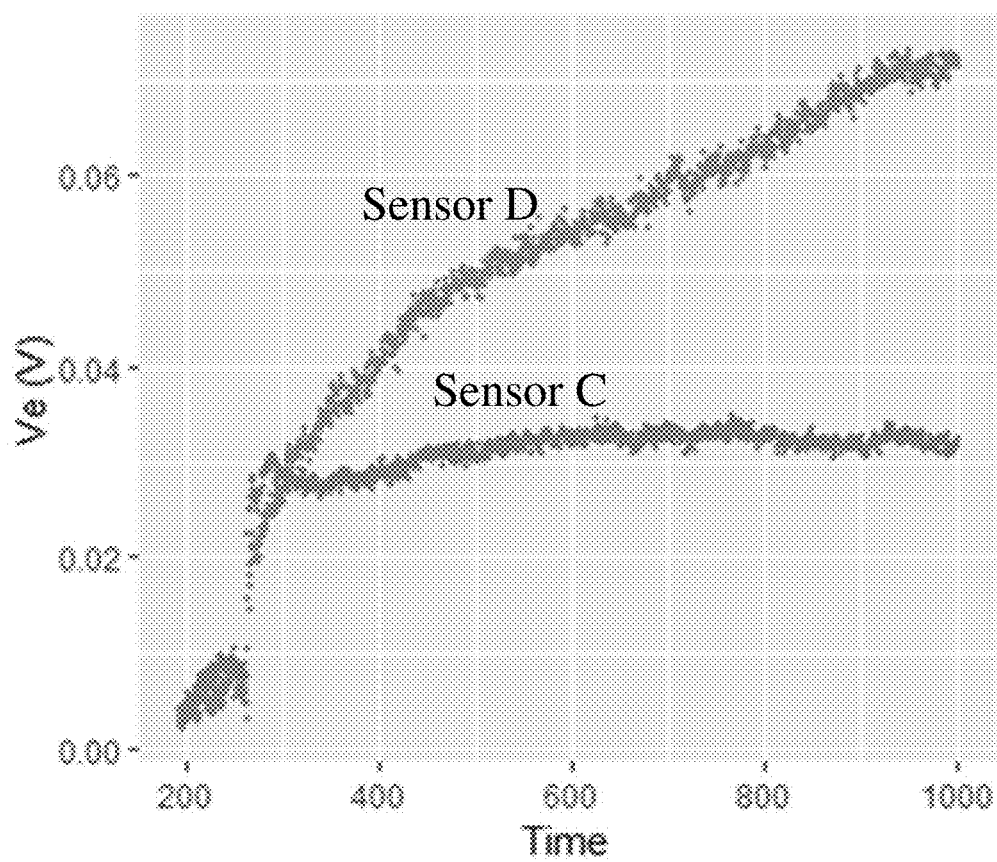

Two further sensors were formed: one including nanowires having anti-S100β antibody-functionalized surfaces of the nanowire (Sensor C) and one including nanowires having anti-DDK antibody-functionalized surfaces of the nanowire (Sensor D). Sensors C and D were first exposed to unmodified plasma and then exposed to plasma spiked with S100β at a level of 2.5 ng/mL. FIG. 22 shows the equivalent surface potential as a function of time for both sensors (the sensors were exposed to the S100β-spiked plasma at the time point of 260 seconds). As can be seen from FIG. 22, both Sensors C and D exhibited an increase in equivalent surface potential upon exposure to the spiked plasma. The equivalent surface potential for Sensor C remained relatively constant thereafter, while that of Sensor D continued to increase. It is believed that the initial increase in equivalent surface potential of Sensors C was due to the change in composition of the fluid to which it is was exposed, and that the lack of change in equivalent surface potential thereafter is indicative of a lack of specific binding. It is believed that the increase in equivalent surface potential with time for Sensor D is indicative of continuous specific binding of S1000 to the nanowire therein, and that the rate of change in equivalent surface potential is directly dependent on the binding constant of S1000 to the nanowire and the concentration of S1000 in the fluid to which Sensor D was exposed.

Example 4

This Example describes sensors comprising a pair of electrodes in electrical communication by a functionalized nanowire.

Figure 23:
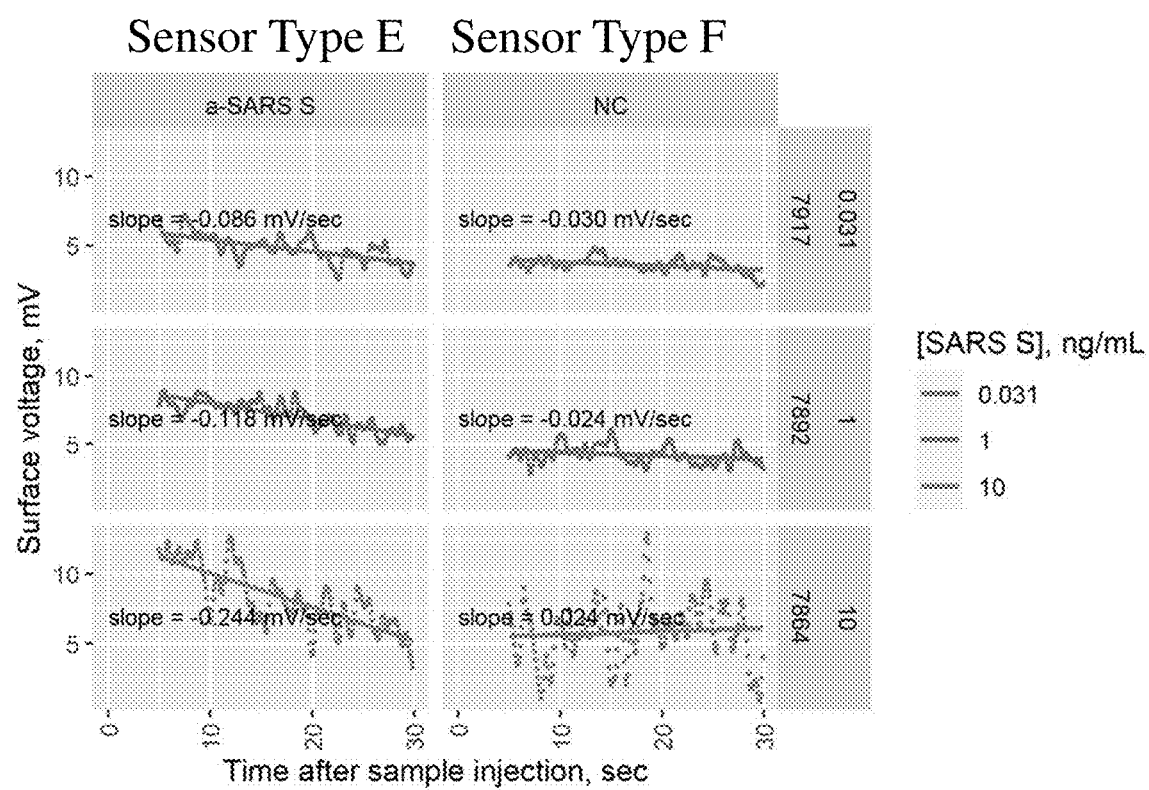

Two types of sensors were formed: a first type of sensor comprising silicon nanowires comprising surfaces functionalized with anti-SARS-CoV-2 spike protein antibodies (Sensor Type E), and a second sensor comprising silicon nanowires comprising surfaces functionalized with control antibodies (Sensor Type F). Sensors of each type were exposed to human saliva comprising SARS-CoV-2 spike protein at varying levels of concentration therein. FIG. 23 shows the equivalent surface potential of these sensors as a function of time. During the time scale over which the measurements shown in FIG. 23 were made, the change in this equivalent surface potential with time is believed to be proportional to the initial rate at which the SARS-CoV-2 spike protein bonds to the silicon nanowires. From FIG. 23, it is thus apparent that the change in equivalent surface potential with time varied with the concentration of the SARS-CoV-2 spike protein in the fluid to which the sensors were exposed for Sensor Type E, indicating that the rate of binding of the SARS-CoV-2 spike protein to the silicon nanowires depended on its concentration in the fluid to which the sensors were exposed. By contrast, the sensors of Sensor Type F exhibited a change in equivalent surface potential with time that was relatively independent of the concentration of SARS-CoV-2 spike protein in the fluid to which they were exposed, indicating that little or no binding of the SARS-CoV-2 spike protein to the silicon nanowires occurred. Accordingly, it is believed that sensors comprising surfaces functionalized with anti-SARS-CoV-2 spike protein antibodies can be employed to detect the presence of such antibodies in a fluid and/or to determine their concentration therein.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A sensor, comprising:
   a first electrode;
   a second electrode; and
   a plurality of nanowires, wherein:
      the first and second electrodes are disposed on the plurality of nanowires;
      the plurality of nanowires forms a circular structure;
      the sensor comprises a plurality of pairs of electrodes comprising greater than or equal to 5 pairs of electrodes;
      the plurality of pairs of electrodes comprises the first electrode and the second electrode; and
      the plurality of pairs of electrodes are equidistant from a center point.

2. A sensor as in claim 1, wherein the plurality of pairs of electrodes comprises fewer than or equal to 40 pairs of electrodes.

3. A sensor as in claim 1, the plurality of nanowires comprises nanowires having an average length of greater than or equal to 5 microns and less than or equal to 50 microns.

4. A sensor as in claim 1, wherein the plurality of nanowires comprises a nanowire having a charged surface.

5. A sensor as in claim 1, wherein the plurality of nanowires comprises a nanowire comprising a binding entity.

6. A sensor as in claim 5, wherein the binding entity is a binding entity for a biomarker for brain injury.

7. A sensor as in claim 5, wherein the binding entity is a binding entity for a small-molecule biomarker.

8. A sensor as in any claim 5, wherein the binding entity is a binding entity for lipids.

9. A sensor as in claim 5, wherein the binding entity is a binding entity for a viral protein.

10. A sensor as in claim 9, wherein the viral protein is a human viral protein, a non-human animal viral protein, and/or a plant viral protein.

11. A sensor as in claim 1, wherein the sensor comprises a blocking layer.

12. A sensor as in claim 11, wherein the blocking layer is disposed on the plurality of nanowires.

13. A sensor as in claim 11, wherein the blocking layer comprises a protein.

14. A sensor as in claim 11, wherein the blocking layer comprises a stabilizer which is removed upon contact with liquid.

15. A method comprising exposing the sensor of claim 1 to a bodily fluid.

16. A method as in claim 15, wherein the bodily fluid was collected using a swab.

17. A method as in claim 15, wherein the bodily fluid comprises a solid or viscous sample resuspended in another fluid.

18. A sensor as in claim 1, wherein the sensor is configured to output a signal indicative of a concentration of a protein or other biomarker in a fluid.

19. A sensor as in claim 1, wherein the pairs of electrodes in the plurality of pairs of electrodes are disposed on the circular structure.

20. A sensor as in claim 1, wherein the sensor comprises two or more groups of nanowires that are functionalized with different chemistries.

21. A sensor as in claim 1, wherein a nanowire in the plurality of nanowires comprises a nucleic acid, DNA, RNA or peptide-nucleic acid complimentary to the genetic sequence to be detected.

22. A sensor as in claim 1, wherein the nanowires in the plurality of nanowires have an electrical conductivity of greater than or equal to 0.333 S/cm.

23. A sensor as in claim 22, wherein the nanowires in the plurality of nanowires have an electrical conductivity of less than or equal to 50,000 S/cm.

24. A sensor as in claim 1, wherein the plurality of nanowires comprises at most 100,000 nanowires.

25. A sensor as in claim 1, wherein the nanowires in the plurality of nanowires are substantially tangential to the circular structure.

26. A sensor as in claim 1, wherein the first and second electrodes are placed in electrical communication to one another by exactly one nanowire.

* * * * *